US00RE45196E

(19) United States
(12) Reissued Patent
Tuck et al.

(10) Patent Number: US RE45,196 E
(45) Date of Reissued Patent: Oct. 14, 2014

(54) COMPOSITIONS COMPRISING STRUCTURALLY STABLE CONJUGATE MOLECULES

(75) Inventors: Stephen F. Tuck, Oakland, CA (US); Roberto Rodriguez, Ballwin, MO (US)

(73) Assignee: Dynavax Technologies Corporation, Berkeley, CA (US)

(21) Appl. No.: 13/475,928

(22) Filed: May 18, 2012 (Under 37 CFR 1.47)

Related U.S. Patent Documents

Reissue of:
(64) Patent No.: 7,718,622
Issued: May 18, 2010
Appl. No.: 11/367,661
Filed: Mar. 3, 2006

U.S. Applications:
(60) Provisional application No. 60/658,947, filed on Mar. 4, 2005.

(51) Int. Cl.

| | |
|---|---|
| ***A61K 48/00*** | (2006.01) |
| ***A61K 39/35*** | (2006.01) |
| ***A61K 39/36*** | (2006.01) |
| ***A61K 39/395*** | (2006.01) |
| ***A61K 39/00*** | (2006.01) |
| ***A61K 9/127*** | (2006.01) |
| ***C07H 21/04*** | (2006.01) |
| ***C07H 21/02*** | (2006.01) |

(52) U.S. Cl.
USPC ..... 435/43; 424/184.1; 424/130.1; 424/450; 424/185.1; 536/23.1; 536/24.2; 514/21.2

(58) Field of Classification Search
None
See application file for complete search history.

(56) References Cited

U.S. PATENT DOCUMENTS

| | | | |
|---|---|---|---|
| 4,705,684 | A | 11/1987 | Beachey |
| 5,679,647 | A | 10/1997 | Carson et al. |
| 5,804,566 | A | 9/1998 | Carson et al. |
| 5,830,877 | A | 11/1998 | Carson et al. |
| 5,843,943 | A | 12/1998 | Carson et al. |
| 5,849,719 | A | 12/1998 | Carson et al. |
| 5,874,408 | A | 2/1999 | Nayar |
| 5,917,021 | A | 6/1999 | Lee |
| 5,985,847 | A | 11/1999 | Carson et al. |
| 6,174,872 | B1 | 1/2001 | Carson et al. |
| 6,225,292 | B1 | 5/2001 | Raz et al. |
| 6,251,678 | B1 | 6/2001 | Volkin et al. |
| 6,270,757 | B1 | 8/2001 | Warne |
| 6,323,201 | B1 | 11/2001 | Carson et al. |
| 6,426,336 | B1 | 7/2002 | Carson et al. |
| 6,498,148 | B1 | 12/2002 | Raz |
| 6,514,948 | B1 | 2/2003 | Raz et al. |
| 6,534,062 | B2 | 3/2003 | Raz et al. |
| 6,552,006 | B2 | 4/2003 | Raz et al. |
| 6,562,798 | B1 | 5/2003 | Schwartz |
| 6,562,819 | B2 | 5/2003 | Carson et al. |
| 6,589,940 | B1 | 7/2003 | Raz et al. |
| 6,610,661 | B1 | 8/2003 | Carson et al. |
| 6,613,751 | B2 | 9/2003 | Raz et al. |
| 6,685,940 | B2 | 2/2004 | Andya et al. |
| 6,689,353 | B1 | 2/2004 | Wang et al. |
| 6,689,600 | B1 | 2/2004 | Wu et al. |
| 6,737,066 | B1 | 5/2004 | Moss |
| 6,797,276 | B1 | 9/2004 | Glenn et al. |
| 6,893,821 | B2 | 5/2005 | Raz et al. |
| 7,108,844 | B2 | 9/2006 | Carpentier |
| 7,129,222 | B2 | 10/2006 | Van Nest et al. |
| 7,157,437 | B2 | 1/2007 | Van Nest |
| 7,183,111 | B2 | 2/2007 | Van Nest et al. |
| 7,186,700 | B2 | 3/2007 | Standring et al. |
| 7,223,398 | B1 | 5/2007 | Tuck et al. |
| 7,250,403 | B2 | 7/2007 | Van Nest et al. |
| 7,255,868 | B2 | 8/2007 | Fearon et al. |
| 7,479,285 | B1 | 1/2009 | Van Nest et al. |
| 7,488,490 | B2 | 2/2009 | Davis et al. |
| 7,514,414 | B2 | 4/2009 | Klinman et al. |
| 7,517,861 | B2 | 4/2009 | Krieg et al. |
| 7,521,063 | B2 | 4/2009 | Klinman et al. |
| 7,524,828 | B2 | 4/2009 | Krieg et al. |
| 7,541,040 | B2 | 6/2009 | Puri et al. |
| 7,566,703 | B2 | 7/2009 | Krieg et al. |

(Continued)

FOREIGN PATENT DOCUMENTS

| | | | |
|---|---|---|---|
| JP | 2003-513680 | A | 4/2003 |
| JP | 2004-537535 | A | 12/2004 |

(Continued)

OTHER PUBLICATIONS

Beachey, E.H. et al. (1984). "Epitope-Specific Protective Immunogenicity of Chemically Synthesized 13-, 18-, and 23-Residue Peptide Fragments of Streptococcal M Protein," *Proc. Natl. Acad. Sci.* USA 81(7):2203-2207.

Carson, D.A. et al. (Nov. 17, 1997). "Oligonucleotide Adjuvants for T Helper 1 (Th1)-specific Vaccination," *J. Exp. Med.* 186(10):1621-1622.

Dale, J.B. et al. (1983). "Type-Specific Immunogenicity of a Chemically Synthesized Peptide Fragment of Type 5 Streptococcal M Protein," *J. Exp. Med.* 158(5):1727-1732.

De Martino, M. et al. (Aug. 1999). "Low IgG3 and High IgG4 Subclass Levels in Children with Advanced Human Immunodeficiency Virus-Type 1 Infection and Elevated IgE Levels," *Ann. Allergy Asthma Immunol.* 83(2):160-164.

(Continued)

*Primary Examiner* — Nita M Minnifield
(74) *Attorney, Agent, or Firm* — Morrison & Foerster LLP

(57) ABSTRACT

The present invention provides compositions comprising conjugate molecules that are structurally stable at a temperature of between about 2 degrees C. and 8 degrees C. In some examples, a conjugate molecule comprises an antigen, such as an allergen. In some examples, a conjugate molecule comprises the Ragweed antigen Amb a 1. The present invention provides methods for making and using such compositions. Provided herein are methods for modulating an immune response in an individual comprising administration of a composition comprising a structurally stable conjugate molecule as described herein.

38 Claims, 9 Drawing Sheets

(56) References Cited

U.S. PATENT DOCUMENTS

| | | | | |
|---|---|---|---|---|
| 7,569,553 | B2 | 8/2009 | Krieg | |
| 7,576,066 | B2 | 8/2009 | Krieg | |
| 7,585,847 | B2 | 9/2009 | Bratzler et al. | |
| 7,605,138 | B2 | 10/2009 | Krieg | |
| 7,615,227 | B2 | 11/2009 | Klinman et al. | |
| 7,615,539 | B2 | 11/2009 | Uhlmann et al. | |
| 7,884,083 | B2 | 2/2011 | Van Nest et al. | |
| 8,003,115 | B2 | 8/2011 | Fearon et al. | |
| 8,124,590 | B2 | 2/2012 | Van Nest et al. | |
| 8,372,413 | B2 | 2/2013 | Fearon et al. | |
| 8,597,665 | B2 * | 12/2013 | Fearon et al. | 424/278.1 |
| 8,669,237 | B2 * | 3/2014 | Van Nest et al. | 514/44 R |
| 2001/0046967 | A1 | 11/2001 | Van Nest | |
| 2002/0086839 | A1 | 7/2002 | Raz et al. | |
| 2003/0049266 | A1 | 3/2003 | Fearon et al. | |
| 2003/0133988 | A1 | 7/2003 | Fearon et al. | |
| 2003/0199466 | A1 | 10/2003 | Fearon et al. | |
| 2003/0216340 | A1 | 11/2003 | Van Nest et al. | |
| 2003/0225016 | A1 | 12/2003 | Fearon et al. | |
| 2004/0006034 | A1 | 1/2004 | Raz et al. | |
| 2004/0009942 | A1 | 1/2004 | Van Nest | |
| 2004/0092468 | A1 | 5/2004 | Schwartz | |
| 2004/0132677 | A1 | 7/2004 | Fearon et al. | |
| 2004/0136948 | A1 | 7/2004 | Fearon | |
| 2005/0059626 | A1 | 3/2005 | Van Nest et al. | |
| 2006/0013811 | A1 | 1/2006 | Dina | |
| 2006/0058254 | A1 | 3/2006 | Dina et al. | |
| 2006/0193869 | A1 | 8/2006 | Barrat et al. | |
| 2007/0027098 | A1 | 2/2007 | Raz et al. | |
| 2007/0036807 | A1 | 2/2007 | Tuck et al. | |
| 2007/0049550 | A1 | 3/2007 | Fearon et al. | |
| 2007/0060540 | A1 | 3/2007 | Van Nest | |
| 2007/0190073 | A1 | 8/2007 | Tuck et al. | |
| 2007/0238678 | A1 | 10/2007 | Barrat et al. | |
| 2007/0258994 | A1 | 11/2007 | Van Nest et al. | |
| 2008/0009459 | A1 | 1/2008 | Van Nest et al. | |
| 2008/0181909 | A1 | 7/2008 | Fearon et al. | |
| 2008/0207550 | A1 | 8/2008 | Fearon et al. | |
| 2009/0017075 | A1 | 1/2009 | Van Nest et al. | |
| 2009/0191188 | A1 | 7/2009 | Krieg et al. | |
| 2009/0202575 | A1 | 8/2009 | Krieg et al. | |
| 2011/0038896 | A1 | 2/2011 | Van Nest et al. | |
| 2011/0118341 | A1 * | 5/2011 | Hessel et al. | 514/44 R |
| 2012/0121622 | A1 * | 5/2012 | Van Nest et al. | 424/184.1 |
| 2012/0177701 | A1 * | 7/2012 | Ilyinskii et al. | 424/400 |

FOREIGN PATENT DOCUMENTS

| | | | |
|---|---|---|---|
| WO | WO-95/05853 | A1 | 3/1995 |
| WO | WO-97/28259 | A1 | 8/1997 |
| WO | WO-98/16247 | A1 | 4/1998 |
| WO | WO-98/52948 | A1 | 11/1998 |
| WO | WO-99/62923 | A2 | 12/1999 |
| WO | WO-99/62923 | A3 | 12/1999 |
| WO | WO-00/21556 | A1 | 4/2000 |
| WO | WO-00/69861 | A1 | 11/2000 |
| WO | WO-01/12223 | A2 | 2/2001 |
| WO | WO-01/12223 | A3 | 2/2001 |
| WO | WO-01/15726 | A2 | 3/2001 |
| WO | WO-01/15726 | A3 | 3/2001 |
| WO | WO-01/35991 | A2 | 5/2001 |
| WO | WO-01/35991 | A3 | 5/2001 |
| WO | WO-01/68077 | A2 | 9/2001 |
| WO | WO-01/68077 | A3 | 9/2001 |
| WO | WO-01/68117 | A2 | 9/2001 |
| WO | WO-01/68117 | A3 | 9/2001 |
| WO | WO-01/68144 | A2 | 9/2001 |
| WO | WO-01/68144 | A3 | 9/2001 |
| WO | WO-01/76642 | A1 | 10/2001 |
| WO | WO-03/000922 | A2 | 1/2003 |
| WO | WO-03/000922 | A3 | 1/2003 |
| WO | WO-03/106644 | A2 | 12/2003 |
| WO | WO-03/106644 | A3 | 12/2003 |
| WO | WO-2004/014322 | A2 | 2/2004 |
| WO | WO-2004/014322 | A3 | 2/2004 |
| WO | WO-2004/060396 | A2 | 7/2004 |
| WO | WO-2004/060396 | A3 | 7/2004 |
| WO | WO 2006/096497 | * | 9/2006 |
| WO | WO-2006/096497 | A2 | 9/2006 |
| WO | WO-2006/096497 | A3 | 9/2006 |

OTHER PUBLICATIONS

Duramad, O. et al. (Dec. 15, 2003). "IL-10 Regulates Plasmacytoid Dendritic Cell Response to CpG-Containing Immunostimulatory Sequences," *Blood* 102(13):4487-4492.

Ferreira, F. et al. (2004). "Customized Antigens for Desensitizing Allergic Patients," *Advances in Immunology* 84:79-129, Abstract Only.

Ferreira, F. et al. (2006). "Modified Recombinant Allergens for Safer Immunotherapy," *Inflammation & Allergy-Drug Targets* 5:5-14.

Fornadley, J. (Feb. 1998). "Allergy Immunotherapy," *Otolaryngologic Clinics of North America* 31(1):111-127.

Higgins, D. et al. (2006). "Modulation of Immunogenicity and Allergenicity by Controlling the Number of Immunostimulatory Oligonucleotides Linked to Amb a 1," *J. Allergy Clin. Immunol.* 118:504-510.

Hirose, I. et al. (2008). "Immunomodulatory Effects of CpG Oligodeoxynucleotides On House Dust Mite-Induced Airway Inflammation in Mice," *Int. Arch. Allergy Immunol.* 147(1):6-16.

Horner, A.A. et al. (2002). "Optimized Conjugation Ratios Lead to Allergen Immunostimulatory Oligodeoxynucleotide Conjugates with Retained Immunogenicity and Minimal Anaphylactogenicity," J. *Allergy Clin. Immunol.* 110:413-420.

International Search Report mailed Mar. 1, 2007, for PCT Application No. PCT/US2006/007571, filed Mar. 3, 2006, three pages.

Kreig, A.M. (Jun. 2001). "Now I Know My CpGs," *Trends in Microbiology* 9(6):249-252.

Lea, I.A. et al. (1996). "Cloning and Sequencing of cDNAs Encoding the Human Sperm Protein, Sp17," *Biochim. Biophys. Acta* 1307:263-266.

Liu, H.M. et al. (Sep. 1997). "CpG ODN is an Effective Adjuvant in Immunization with Tumor Antigen," *J. Invest. Medicine* 45(7):333A, Abstract Only.

Marshall, J.D. et al. (2001). "Immunostimulatory Sequence DNA Linked to the Amb a 1 Allergen Promotes $T_H1$ Cytokine Expression While Downregulating $T_H2$ Cytokine Expression in PBMCs From Human Patients With Ragweed Allergy," *J. Allergy Clin. Immunol.* 108:191-197.

Medicago AB (Date Unknown). "Smartbuffers. Phosphate Buffered Saline (PBS), pH 7.4 and 7.2," located at <www.medicaog.se>, 2 pages.

Rafnar, T. et al. (Jan. 15, 1991). "Cloning of *Amb a I* (Antigen E), the Major Allergen Family of Short Ragweed Pollen," *Journal of Biological Chemistry* 266 (2):1229-1236.

Raja, K. et al. (2007). "One-Pot Synthesis, Purification, and Formulation of Bionanoparticle-CpG Oligodeoxynucleotide Hepatitis B Surface Antigen Conjugate Vaccine via Tangential Flow Filtration," *Bioconjugate Chem.* 18:285-288.

Sambrook, J. et al. eds. (1989). "Table B.7," in *Molecular Cloning: A Laboratory Manual*, Second Edition, Cold Spring Harbor Laboratory Press: Cold Spring Harbor, NY, pp. B.12-B.13.

Simons, F.E.R. et al. (Jun. 2004). "Selective Immune Redirection in Humans with Ragweed Allergy by Injecting Amb a 1 Linked to Immunostimulatory DNA," *Journal of Allergy and Clinical Immunology* 113(6):1144-1151.

Sonehara, K. et al. (1996). "Hexamer Palindromic Oligonucleotides with 5' -CG- 3' Motif(s) Induce Production of Interferon," *Journal of Interferon and Cytokine Research* 16:799-803.

Uhlmann, E. (Mar. 2001). "Oligonucleotide technologies: synthesis, production, regulations and applications. Nov. 29-30, 2000, Hamburg, Germany," *Exp. Opin. Biol. Ther.* 1(2):319-328, Abstract Only.

U.S. Appl. No. 09/265,191, filed Mar. 10, 1999, for Carson et al.

Verthelyi, D. et al. (Oct. 2003). "Immunoregulatory Activity of CpG Oligonucleotides in Humans and Nonhuman Primates," *Clinical Immunology* 109(1):64-71.

(56) References Cited

OTHER PUBLICATIONS

Voet, D. et al. (1990). "Table 26-1: Names and Abbreviations of Nucleic Acid Bases, Nucleosides, and Nucleotides," *Biochemistry,* John Wiley & Sons, p. 742.
Widhe, M. et al. (1998). "IgG Subclasses in Lyme Borreliosis: A Study of Specific IgG Subclass Distribution in an Interferon-γ-Predominated Disease," *Scand. J. Immunol.* 47:575-581.
Written Opinion mailed Mar. 1, 2007, for PCT Application No. PCT/US2006/007571, filed Mar. 3, 2006, five pages.
Yamamoto, T. et al. (1994). "Ability of Oligonucleotides with Certain Palindromes to Induce Interferon Production and Augment Natural Killer Cell Activity is Associated with Their Base Length," *Antisense Research and Development* 4:119-122.
Hirose et al, Int. Arch. Allergy Immunol., 2008, 147:6-16.*
Raja et al, Bioconjugate Chem., 2007, 18:285-288.*
Horner et al, J. Allergy Clin. Immunol., 2002, 110:413-420.*
Ferreira et al, Advances in Immunology, 2004, vol. 84, pp. 79-129 abstract only.*
Uhlmann, Exp. Opin. Biol. Ther., 2001, 1/2:321-328.*
Ferreira et al, Inflammation & Allergy-Drug Targets, 2006, 5:5-14.*
Higgins et al, J. Allergy Clin. Immunol., 2006, 118:504-510.*
Marshall et al, J. Allergy Clin. Immunol., 2001, 108:191-197.*

* cited by examiner

COMPOSITIONS COMPRISING STRUCTURALLY STABLE CONJUGATE MOLECULES

Matter enclosed in heavy brackets [ ] appears in the original patent but forms no part of this reissue specification; matter printed in italics indicates the additions made by reissue.

CROSS-REFERENCE TO RELATED APPLICATIONS

This application claims the priority benefit of U.S. Provisional Patent Application 60/658,947, filed Mar. 4, 2005, the disclosure of which is hereby incorporated herein by reference in its entirety.

STATEMENT REGARDING FEDERALLY SPONSORED RESEARCH OR DEVELOPMENT

Not applicable.

[REFERENCE TO A COMPACT DISK APPENDIX]

*SUBMISSION OF SEQUENCE LISTING ON ASCII TEXT FILE*

[Not applicable.] *The content of the following submission on ASCII text file is incorporated herein by reference in its entirety: a computer readable form (CRF) of the Sequence Listing (file name: 377882003530SeqListing.txt, date recorded: May 16, 2012, size: 2 KB).*

BACKGROUND

Immune responses to resolve different pathologies, such as those seen in viral infections, bacterial infections, cancer and allergic reactions are important to the overall health of the host. Successful resolution of infections, cancer, or allergic reactions may depend on the type and magnitude of the immune response. Immunizations, whereby antigen is used to elicit further immune responses, may be helpful in successfully resolving the infections, cancers, and/or allergic reactions. Immunostimulatory polynucleotide-immunomodulatory molecule conjugate compositions are disclosed in WO 98/16247. Immunomodulatory compositions containing an immunostimulatory sequence linked to antigens are disclosed in WO 01/35991. Methods of modulating an immune response using immunostimulatory sequences are disclosed in WO 01/12223.

All publications, references, patent applications, patent publications and patents cited herein are hereby incorporated herein by reference in their entirety.

BRIEF SUMMARY

Provided herein are compositions comprising a structurally stable conjugate molecule, wherein the conjugate molecule comprises a conjugate partner and a polynucleotide comprising an immunostimulatory sequence (ISS) and wherein the composition further comprises a component capable of maintaining the pH of the composition in the range of about 6.0 to about 9.0. In some examples the conjugate partner is an antigen, such as for example, an allergen. In other examples, the allergen is selected from the group consisting of Crustacea allergens, insect allergens, mammalian allergens, mollusks allergens, plant allergens, and fungal allergens. In further examples, the allergen is the plant allergen Ragweed antigen Amb a 1. In some examples, a conjugate molecule is AIC, as described herein. In some examples, the composition comprises more than about 70% of said conjugate molecule in non-aggregate form at a temperature of between about 2 degrees C. and about 8 degrees C. as measured by Right Angle Light Scatter (RALS). In other examples, the composition comprises more than about 80%, more than about 90%, more than 95%, or more than about 97% of said conjugate molecule in non-aggregate form at a temperature of between about 2 degrees C. and about 8 degrees C. as measured by Right Angle Light Scatter (RALS). In other examples, a composition comprising a conjugate partner comprises a component capable of maintaining the pH selected from the group consisting of non-polar components and non-negatively charged components. In further examples, a component capable of maintaining the pH is Histidine. In some examples, the Histidine is present in the composition at a concentration of between about 1 mM and about 50 mM. In other examples, the Histidine is present in the composition at a concentration of between about 5 mM and about 20 mM. In yet other examples, the component capable of maintaining the pH is phosphate. In some examples, the phosphate is present in the composition at a concentration of between about 5 mM and about 50 mM and in other examples, is between about 20 mM and about 50 mM. In some examples, the composition has a pH in the range of about 6.0 to about 9.0. In some examples, the composition has a pH in the range of about 7.0 to about 8.0; and in other examples, in the range of about 7.5 to about 8.0. In some examples, a conjugate molecule comprises an ISS that comprises the hexamer motif AACGTT. In other examples, an ISS comprises the motif GACGCTCC; GACGTCCC; GACGTTCC; GACGCCCC; AGCGTTCC; AGCGCTCC; AGCGTCCC; AGCGCCCC; AACGTCCC; AACGCCCC; AACGTTCC; AACGCTCC; GGCGTTCC; GGCGCTCC; GGCGTCCC; GGCGCCCC; GACGCTCG; GACGTCCG; GACGCCCG; GACGTTCG; AGCGCTCG; AGCGTTCG; AGCGTCCG; AGCGCCCG; AACGTCCG; AACGCCCG; AACGTTCG; AACGCTCG; GGCGTTCG; GGCGCTCG; GGCGTCCG; GGCGCCCG; GACGCT; GACGTC; GACGTT; GACGCC; GACGCU; GACGUC; GACGUU; GACGUT; GACGTU; AGCGTT; AGCGCT; AGCGTC; AGCGCC; AGCGUU; AGCGCU; AGCGUC; AGCGUT; AGCGTU; AACGTC; AACGCC; AACGTT; AACGCT; AACGUC; AACGUU; AACGCU; AACGUT; AACGTU; GGCGTT; GGCGCT; GGCGTC; GGCGCC; GGCGUU; GGCGCU; GGCGUC; GGCGUT; or GGCGTU. In yet other examples, an ISS comprises the sequence

```
5'-TGACTGTGAACGTTCGAGATGA-3';          (SEQ ID NO: 1)

5'-TGACCGTGAACGTTCGAGATGA-3';          (SEQ ID NO: 2)

5'-TCATCTCGAACGTTCCACAGTCA-3';         (SEQ ID NO: 3)

5'-TGACTGTGAACGTTCCAGATGA-3';          (SEQ ID NO: 4)

5'-TCCATAACGTTCGCCTAACGTTCGTC-3';      (SEQ ID NO: 5)

5'-TGACTGTGAABGTTCCAGATGA-3';          (SEQ ID NO: 6)

5'-TGACTGTGAABGTTCGAGATGA-3';          (SEQ ID NO: 7)
or

5'-TGACTGTGAABGTTBGAGATGA-3',          (SEQ ID NO: 8)
```

or where B is 5-bromocytosine. In further examples, an ISS comprises 5'-TGACTGTGAACGTTCGAGATGA-3' (SEQ ID NO:1).

In some examples, the conjugate partner is an antigen and yet in other examples is an allergen. In yet other examples, the allergen is selected from the group consisting of Crustacea allergens, insect allergens, mammalian allergens, mollusks allergens, plant allergens, and fungal allergens. In further examples, the allergen is the plant allergen Ragweed antigen Amb a 1.

In some examples, a composition comprising a conjugate partner further comprises an amino acid selected from the group consisting of Histidine, Glycine, Isoleucine, Leucine, Proline and Alanine. In some examples, the amino acid is Glycine; in some examples, the Glycine is present in the composition at a concentration of between about 230 mM and about 285 mM. In further examples, a composition further comprises a carbohydrate selected from the group consisting of Lactose, Sucrose, Mannose, Maltose, Sorbitol, and Glucose. In some examples, the carbohydrate is Sucrose. In some examples, the Sucrose is present in the composition at a concentration of between about 1% and 10%. In other examples, the carbohydrate is Sorbitol. In some examples, the Sorbitol is present in the composition at a concentration of between about 3% and about 5%. In yet other examples, provided herein are compositions comprising a conjugate molecule; Histidine at a concentration in the range of about 1 mM to about 50 mM; and Glycine at a concentration in the range of about 50 mM to about 300 mM, wherein said composition has a pH in the range of about 6.0 to about 9.0. In other examples, provided herein are compositions comprising a conjugate molecule further comprising Sorbitol in the range of about 1 to 10% or Sucrose at a concentration of about 200 mM to about 250 mM. In some examples, a composition has a pH in the range of about 7.0 to about 8.0. In further examples, provided herein are compositions comprising a conjugate molecule, 5 mM Histidine and 285 mM Glycine at a pH range of between about 7.0 and about 8.0.

In other examples, provided herein are compositions comprising a conjugate partner, 20 mM Histidine and 270 mM Glycine at a pH range of between about 7.0 and about 8.0. In further examples, provided herein are compositions comprising 20 mM Histidine, 50 mM Glycine, and 3.8% Sorbitol at a pH range of between about 7.0 and about 8.0. In further examples, provided herein are compositions comprising 20 mM Histidine, 50 mM Glycine, and 210 mM Sucrose at a pH range of between about 7.0 and about 8.0. The present invention provides compositions in liquid form, lyophilized form, and a liquid form reconstituted from a lyophilized form.

The present invention also provides methods for making and using compositions described herein that comprise structurally stable conjugate molecules, such as for example, but not limited to AIC, and kits and articles of manufacture that comprise such compositions.

BRIEF DESCRIPTION OF THE DRAWINGS

FIG. 2A is 215 nm; FIG. 2B is 260 nm; FIG. 2C is 280 nm.

FIG. 4A shows the effect of pH on AIC: to SEC-HPLC (215 nm). FIG. 4B shows the effect of pH, time and temperature (40°) on AIC: $t_7$ SEC-HPLC (215 nm). FIG. 4C shows the effect of pH, time and temperature (30° C.) on AIC: $t_{14}$ SEC-HPLC (215 nm). Control is 10 mM Sodium Phosphate, 141.7 mM NaCl, pH 7.2.% MRc is % monomer recovery; % Tot Rc is % total recovery; and M Rec t0 is monomer recovery at time 0. (For FIG. 4A, the bars are from left to right % Non-aggregation, % MRc, and % Tot Rc for each of Ctl (control), PBS control and each pH value. For FIGS. 4B-4C, the bars are from left to right, % Non-aggregation, % MRc, % Tot Rc; and M Rec t0 for each of Ctl (control), PBS control and each pH value).

DETAILED DESCRIPTION OF THE INVENTION

Figure 1:
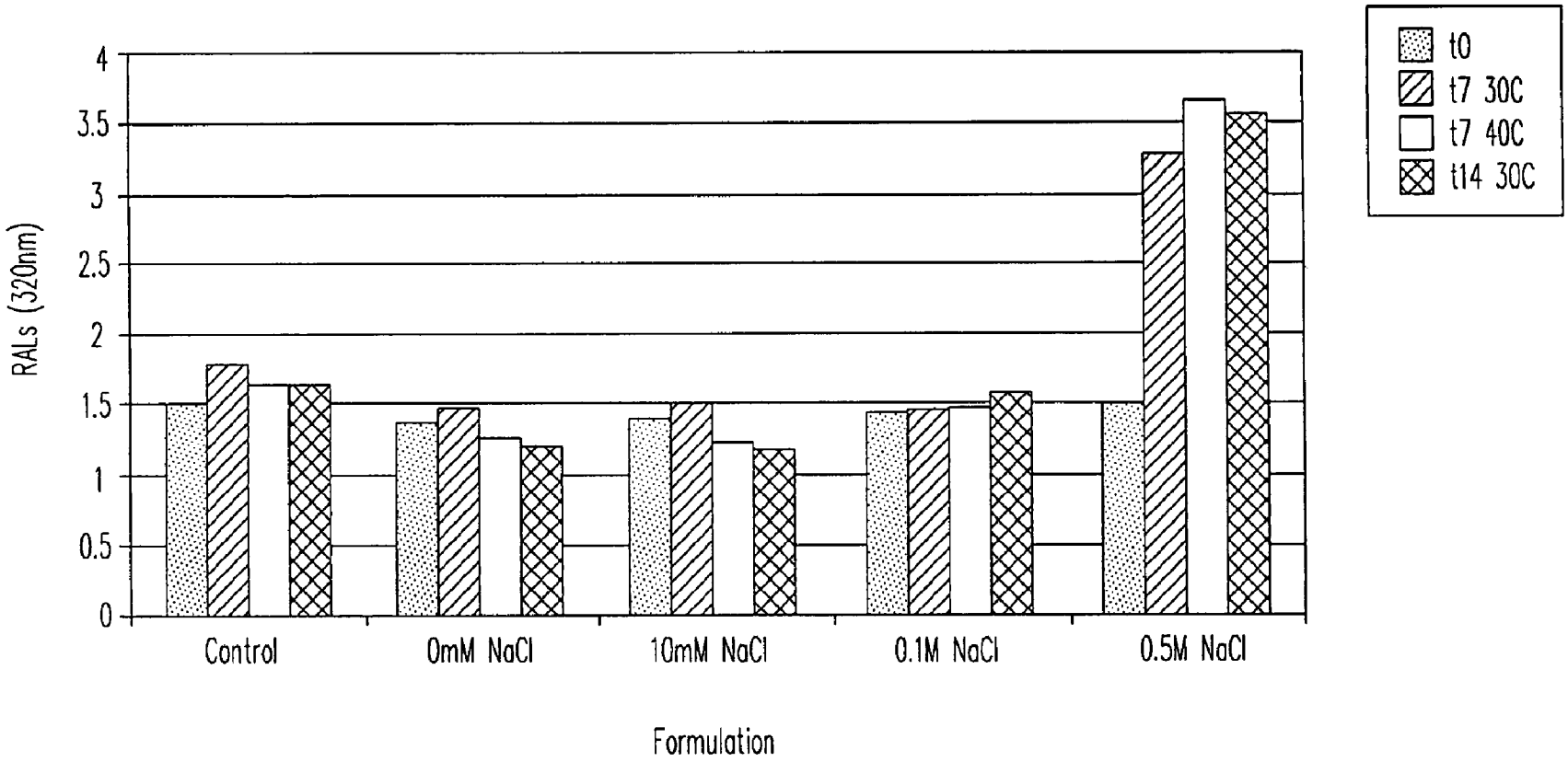
FIG. 1 shows the effect of ionic strength, time and temperature on AIC as determined by RALS as discussed in Example 5. Control is 10 mM Sodium Phosphate, 141.7 mM NaCl, pH 7.2. (The bars are from left to right, t0, t7 30C, t7 40C, t14 30C, for each of the control and NaCl concentrations).

Described herein are compositions comprising a conjugate molecule, wherein the conjugate molecule comprises a conjugate partner and a polynucleotide comprising an immunostimulatory sequence (ISS). The present invention is based, in part, upon the finding that the structural stability of a conjugate molecule within a composition is dependent upon temperature, salt and pH conditions. The present inventors have found that a conjugate molecule comprising an antigen undergoes aggregation with time when stored liquid at 2-8 degrees C. in compositions comprising sodium phosphate and sodium chloride. It was also found that low pH caused a conjugate molecule comprising an antigen to aggregate reversibly under conditions of low ionic strength. Provided herein are compositions developed to minimize or reduce aggregation of conjugate molecules and methods of making and using such compositions. Described herein are compositions comprising a conjugate molecule that is structurally stable at a temperature of between about 2 degrees C. to about 8 degrees C. In some examples, the conjugate molecule comprises an antigen, such as for example, an allergen. In some examples, the allergen is purified short ragweed antigen (Amb a 1). Accordingly, provided herein are compositions comprising a conjugate molecule that comprises Amb a 1 that is structurally stable at about 2 to about 8° C.

Described herein are compositions comprising a conjugate molecule and a component capable of maintaining the pH of the composition in the range of about 6.0 to about 9.0. In some examples, the composition comprises more than 70%, more than 80%, more than 90%, more than 95%, more than 97%, more than 98% or more than 99% of said conjugate molecule in non-aggregate form at a temperature of between about 2 degrees C. and about 8 degrees C. In some examples, the composition comprises more than 70%, more than 80%, more then 90%, more then 95% or more than 97% of said conjugate molecule in non-aggregate form, for a period of up to about 1 week, up to about 2 weeks, up to about 3 weeks, up to about 4 weeks, up to about 6 weeks, up to about 8 weeks, up to about 10 weeks, up to about 12 weeks, up to about 14 weeks, up to about 16 weeks, up to about 18 weeks, up to about 20 weeks, up to about 22 weeks, up to about 24 weeks, up to about 1 year or up to about 2 years. In some examples, aggregation is measured by Right Angle Light Scatter (RALS). In other examples, aggregation of a conjugate molecule in a composition is measured by intrinsic fluorescence (IF), extrinsic fluorescence (EF) and/or SEC-HPLC which may or may not be in combination with RALS. In some examples, the conjugate molecule comprises an antigen. Examples of antigens are known in the art and include but are not limited to peptides, lipids, polysaccharides, gangliosides, and glycoproteins. In some examples the antigen is an allergen. Examples of allergens are known in the art and described herein and include, but are not limited to, Crustacea allergens, insect allergens, mammalian allergens, mollusks allergens, plant allergens, and fungal allergens. In some examples, the allergen is a plant allergen, such as for example, Ragweed antigen. In some examples, the allergen is Amb a 1. Accordingly, provided herein are compositions comprising a conjugate molecule that comprises Amb a 1 that further comprises a component capable of maintaining the pH of the composition in the range of about 6.0 to about 9.0, wherein the composition comprises more than about 70%, more than about 80%, more than about 90%, more than about 95% or more than about 97% of said conjugate molecule in non-aggregate form at a temperature of between about 2 degrees C. and about 8 degrees C. In other examples, a composition comprising a conjugate molecule may further comprise one or more of 1) an amino acid, 2) a carbohydrate, 3) a surfactant, or 4) other suitable component as long as the composition comprises more than 70%, more than about 80%, more than about 90%, more than about 95% or more than about 97% of said conjugate molecule comprising Amb a 1 in non-aggregate form. In some examples, the composition is in liquid form. In other examples, the composition is lyophilized and in yet other examples, the composition is in liquid form that has been reconstituted from a lyophilized form.

Described herein are compositions comprising a conjugate molecule wherein less than about 30%, less than about 20%, less than about 10%, less than about 5% or less than about 3% of the conjugate molecule present in the composition is in aggregate form at a temperature between about 2 degrees C. and about 8 degrees C. In some examples, less than about 30%, less than about 20%, less than about 10%, less than about 5% or less than about 3% of the conjugate molecule present in the composition is in aggregate form at a temperature between about 2 degrees C. and about 8 degrees C. for a period of up to about 1 week, up to about 2 weeks, up to about 3 weeks, up to about 4 weeks, up to about 6 weeks, up to about 8 weeks, up to about 10 weeks, up to about 12 weeks, up to about 14 weeks, up to about 16 weeks, up to about 18 weeks, up to about 20 weeks, up to about 22 weeks, up to about 24 weeks, up to about 1 year or up to about 2 years. In some examples, aggregation of a conjugate molecule in a composition is measured by right angle light scatter (RALS). In some examples, the conjugate molecule comprises an antigen. Generally, the antigens are peptides, lipids (e.g., sterols excluding cholesterol, fatty acids, and phospholipids), polysaccharides, gangliosides and glycoproteins. In some examples, the antigens include, but are not limited to antigens from an infectious agent, including protozoan, bacterial, fungal (including unicellular and multicellular), and viral infectious agents. For example, antigens from parasitic organisms include schistosome egg antigens (e.g., Sm-p40) from Schistosome species (e.g., S. mansoni) and antigens from Toxoplasma species (e.g., T. gondii). See, for example, Stadecker et al. (1998) Parasite Immunol. 20:217-221; Subauste et al. (1993) Curr. Opin. Immunol. 5:532-527. In some examples, the antigen is an allergen. Examples of allergens are known in the art and described herein and include, but are not limited to, Crustacea allergens, insect allergens, mammalian allergens, mollusks allergens, plant allergens, and fungal allergens. In some examples, the allergen is a plant allergen, such as for example, Ragweed antigen. In some examples, the allergen is Amb a 1. Accordingly, provided herein are compositions comprising a conjugate molecule comprising Amb a1 wherein less than about 30%, less than about 20%, less than about 10%, less than about 5% or less than about 3% of the conjugate molecule present in the composition is in aggregate form at a temperature between about 2 degrees C. and about 8 degrees C.

Provided herein are methods for making and using compositions comprising a structurally stable conjugate molecule as described herein. Provided herein are methods for modulating the immune response of a mammalian host that comprise administration of a composition comprising a structurally stable conjugate molecule as described herein to a mammalian host; pharmaceutical compositions comprising a structurally stable conjugate molecule; kits comprising compositions comprising a structurally stable conjugate molecule; and articles of manufacture comprising a composition comprising a structurally stable conjugate molecule. In some examples, an article of manufacture comprises a composition comprising a conjugate molecule wherein the composition comprises greater than about 70%, greater than about 80%, greater than about 90%, greater than about 95% or greater than about 97% of the conjugate molecule in non-aggregate form at a temperature of between about 2 degrees C. and about 8 degrees C. In some examples, aggregation is measured by RALS. In other examples, an article of manufacture comprises a liquid composition comprising a conjugate molecule and in other examples an article of manufacture comprises a lyophilized composition comprising a conjugate molecule. In yet other examples, an article of manufacture comprises a reconstituted liquid composition (reconstituted from a lyophilized composition) comprising a structurally stable conjugate molecule.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning. A Laboratory Manual, second edition (Sambrook et al., 1989); Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); The Immunoassay Handbook (David Wild, ed., Stockton Press NY, 1994); and Methods of Immunological Analysis (R. Masseyeff, W. H. Albert, and N. A. Staines, eds., Weinheim: VCH Verlags gesellschaft mbH, 1993); and Gennaro, et al. 2000, Remington: the Science and Practice of Pharmacy, 20$^{th}$ Ed. Lipincott Williams and Wilkins: Baltimore, Md.

DEFINITIONS

As used herein, the singular form "a", "an", and "the" includes plural references unless indicated otherwise. For example, "an" ISS includes one or more ISS.

The term "immunostimulatory sequence" or "ISS" as used herein refers to polynucleotide sequences that effect a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, $CD4^+$ T lymphocytes, $CD8^+$ T lymphocytes, B lymphocytes, and the like. Preferably, the ISS sequences preferentially activate a Th1-type response. A polynucleotide for use in the invention contains at least one ISS. As used herein, "ISS" is also a shorthand term for an ISS-containing polynucleotide.

A "conjugate molecule" as used herein refers to a molecule or complex that comprises an ISS (that is, an ISS-containing polynucleotide) and a conjugate partner. In some examples, the ISS and conjugate partner are linked directly or indirectly. Such conjugate linkages include covalent and/or non-covalent linkages. Conjugate partners include but are not limited to antigens. A "population of conjugate molecules" is a group of ISS-conjugate partners (i.e., ISS directly or indirectly linked, or attached, to conjugate partner). For purposes of this invention, it is understood that such populations do not necessarily have, and may or may not have, a constant number of ISS attached to each conjugate partner. Typically, a given population will have a distribution of molecular weights (based on varying extent of conjugation within a given population) and thus an average number of ISS conjugated to the conjugate partner. It is understood that any of the populations of conjugate molecules described herein may contain molecules of free conjugate partners (i.e., conjugate partner not linked to ISS) and/or free ISS (i.e., ISS not linked to conjugate partner), due to, for example, incomplete conjugation and/or purification. For purposes of this invention, the populations described herein contain conjugate molecules, but need not exclusively contain conjugate molecules. As used herein, an "AIC" conjugate molecule refers to the Ragweed allergen, Amb a 1, conjugated to an ISS.

Structural stability of a conjugate molecule within a composition refers to a composition in which the conjugate molecule essentially retains it physical stability and integrity. Physical stability of a conjugate molecule within a composition is measured by the amount, that is, percentage (%), of aggregation of the conjugate molecule in the composition. Generally, increased % of aggregation of conjugate molecules within a composition is correlated with decreased structurally stability of conjugate molecules within a composition. Structural stability of a conjugate molecule within a compositions does not require that there is 0% aggregation of conjugate molecules within the composition, or 0% aggregation of free, that is, non-conjugated, conjugate partners, if present in the composition, or 0% aggregation of free, that is, non-conjugated ISS, if present in the composition. A composition comprising a conjugate molecule that is structurally stable refers to a composition wherein greater than about 70%, greater than about 80%, greater than about 90%, greater than about 95% or greater than about 97% of the conjugate molecule is present in non-aggregate form in the composition. As used herein, the phrase "non-aggregate form" with respect to a conjugate molecule includes but is not limited to the conjugate molecule in monomer form. Generally, increased % of monomers of conjugate molecules within a composition is correlated with increased structurally stability of the conjugate molecules within a composition. Accordingly, a composition comprising a conjugate molecule that is structurally stable refers to, that is includes, a composition wherein at least about 70%, at least about 80%, at least about 90%, at least 95% and at least about 97% of the conjugate molecule is present in the composition in monomer form at a temperature between about 2 degrees C. and about 8 degrees C. A composition comprising a conjugate molecule that is structurally stable refers to, that is includes, a composition wherein less than about 30%, less than about 20%, less than about 10%, less than about 5% or less than about 3% of the conjugate molecule is present as an aggregate in the composition. Various methods for measuring structural stability are available in the art and are disclosed herein and include but are not limited to Right Angle Light Scatter (RALS), either alone or in combination with other methods known in the art and described herein, including but not limited to IF, EF and SEC-HPLC. In some examples, % aggregation of a conjugate molecule within a composition is measured by RALS. A composition comprising a conjugate molecule that is "destabilized" is one that has greater than about 30%, greater than about 40%, greater than about 50%, greater than about 60%, greater than about 70%, greater than about 80%, greater than about 90% or greater than about 95% of the conjugate molecule in the composition present in aggregate form.

An "average" of a given parameter (such as number of ISS-containing polynucleotides or mass) in a given population means the total of that parameter for the entire population divided by the number of members of the population. For example, the average number of ISS-containing polynucleotides attached to conjugate partner refers to the average number of ISS-containing polynucleotides per conjugate partner in a population of conjugate partner molecules (i.e., total number of ISS-containing polynucleotides divided by total number of conjugate partners). As described below, this number is usually derived from weight determinations of polynucleotide to conjugate partner, as measured, for example, by spectroscopy.

A "median" number or weight for a given population refers to a number or weight at which half the population is above, and half the population is below. For example, a median number of ISS-containing polynucleotides per conjugate partner means that half the conjugate partners in the population have a lower number of ISS-containing polynucleotides per conjugate partner, and half have a higher number.

As used interchangeably herein, the terms "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments. Oligonucleotides are polymers of nucleosides joined, generally, through phosphoester linkages. A nucleoside consists of a purine (adenine or guanine or derivative thereof) or pyrimidine (thymine, cytosine or uracil, or derivative thereof) base bonded to a sugar. The four nucleoside units (or bases) in DNA are called deoxyadenosine, deoxyguanosine, deoxythymidine, and deoxycytidine. A nucleotide is a phosphate ester of a nucleoside.

The term "immunomodulatory" or "modulating an immune response" as used herein includes immunostimulatory as well as immunosuppressive effects. Immunostimulatory effects include, but are not limited to, those that directly or indirectly enhance cellular or humoral immune responses. Examples of immunostimulatory effects include, but are not limited to, increased antigen-specific antibody production; activation or proliferation of a lymphocyte population such as NK cells, $CD4^+$ T lymphocytes, $CD8^+$ T lymphocytes, macrophages and the like; increased synthesis of immunostimulatory cytokines including, but not limited to, IL-1, IL-2, IL-4, IL-5, IL-6, IL-10, IL-12, IFN-α, IFN-β, IFN-γ, TNF-α and the like Immunosuppressive effects include those that directly or indirectly decrease cellular or humoral immune responses. Examples of immunosuppressive effects include, but are not limited to, a reduction in antigen-specific antibody production such as reduced IgE production; activation of lymphocyte or other cell populations that have immunosuppressive activities such as those that result in immune tolerance; and increased synthesis of cytokines that have suppressive effects toward certain cellular functions. One example of this is IFN-γ, which appears to block IL-4 induced class switch to IgE and IgG1, thereby reducing the levels of these antibody subclasses.

"Extent of conjugation" means the average degree of conjugation in a given population. As described herein, extent of conjugation may be characterized by any of a number of structural and/or functional parameters, either alone or in any combination.

The term "antigen" means a substance that is recognized and bound specifically by an antibody or by a T cell antigen receptor. Antigens can include peptides, proteins, glycoproteins, polysaccharides, complex carbohydrates, sugars, gangliosides, lipids and phospholipids; portions thereof and combinations thereof. The antigens can be those found in nature or can be synthetic. Antigens suitable for administration with ISS include any molecule capable of eliciting a B cell or T cell antigen-specific response. Preferably, antigens elicit an antibody response specific for the antigen. Haptens are included within the scope of "antigen." A hapten is a low molecular weight compound that is not immunogenic by itself but is rendered immunogenic when conjugated with an immunogenic molecule containing antigenic determinants. Small molecules may need to be haptenized in order to be rendered antigenic. Preferably, in some examples, antigens of the present invention include peptides, lipids (e.g. sterols, fatty acids, and phospholipids), polysaccharides such as those used in Hemophilus influenza vaccines, gangliosides and glycoproteins.

"Adjuvant" refers to a substance which, when added to an immunogenic agent such as antigen, nonspecifically enhances or potentiates an immune response to the agent in the recipient host upon exposure to the mixture.

The term "peptide" are polypeptides that are of sufficient length and composition to effect a biological response, e.g. antibody production or cytokine activity whether or not the peptide is a hapten. Typically, the peptides are of at least six amino acid residues in length. The term "peptide" further includes modified amino acids (whether or not naturally or non-naturally occurring), such modifications including, but not limited to, phosphorylation, glycosylation, pegylation, lipidization and methylation.

"Antigenic peptides" can include purified native peptides, synthetic peptides, recombinant proteins, crude protein extracts, attenuated or inactivated viruses, cells, micro-organisms, or fragments of such peptides. An "antigenic peptide" or "antigen polypeptide" accordingly means all or a portion of a polypeptide which exhibits one or more antigenic properties. Thus, for example, an "Amb a 1 antigenic polypeptide" or "Amb a 1 polypeptide antigen" is an amino acid sequence from Amb a 1, whether the entire sequence, a portion of the sequence, and/or a modification of the sequence, which exhibits an antigenic property (i.e., binds specifically to an antibody or a T cell receptor).

A "delivery molecule" or "delivery vehicle" is a chemical moiety which facilitates, permits, and/or enhances delivery of an ISS and/or antigen to a particular site and/or with respect to particular timing. A delivery vehicle may or may not additionally stimulate an immune response.

An "allergic response to antigen" means an immune response generally characterized by the generation of eosinophils and/or antigen-specific IgE and their resultant effects. As is well-known in the art, IgE binds to IgE receptors on mast cells and basophils. Upon later exposure to the antigen recognized by the IgE, the antigen cross-links the IgE on the mast cells and basophils causing degranulation of these cells, including, but not limited, to histamine release. It is understood and intended that the terms "allergic response to antigen", "allergy", and "allergic condition" are equally appropriate for application of some of the methods of the invention. Further, it is understood and intended that the methods of the invention include those that are equally appropriate for prevention of an allergic response as well as treating a pre-existing allergic condition.

As used herein, the term "allergen" means an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule. A number of isolated allergens are known in the art. These include, but are not limited to, those provided herein.

The term "desensitization" refers to the process of the administration of increasing doses of an allergen to which the subject has demonstrated sensitivity. Examples of allergen doses used for desensitization are known in the art, see, for example, Fornadley (1998) Otolaryngol. Clin. North Am. 31:111-127.

"Antigen-specific immunotherapy" refers to any form of immunotherapy which involves antigen and generates an antigen-specific modulation of the immune response. In the allergy context, antigen-specific immunotherapy includes, but is not limited to, desensitization therapy.

An "individual" is a vertebrate, preferably a mammal, more preferably a human. Mammals include, but are not limited to, humans, primates, farm animals, sport animals, rodents and pets.

An "effective amount" or a "sufficient amount" of a substance is that amount sufficient to effect beneficial or desired results, including clinical results, and, as such, an "effective amount" depends upon the context in which it is being applied. In the context of administering a composition that modulates an immune response to an antigen, an effective amount of a composition comprising an ISS-conjugate partner (that is, an ISS and conjugate partner) is an amount sufficient to achieve such a modulation as compared to the immune response obtained when the antigen is administered alone. An effective amount can be administered in one or more administrations.

The term "co-administration" as used herein refers to the administration of at least two different substances sufficiently close in time to modulate an immune response. Preferably, co-administration refers to simultaneous administration of at least two different substances.

"Stimulation" of an immune response, such as Th1 response, means an increase in the response, which can arise from eliciting and/or enhancement of a response.

An "allergy-related disorder" means a disorder resulting from the effects of an antigen-specific IgE immune response. Such effects can include, but are not limited to, hypotension and shock. Anaphylaxis is an example of an allergy-related disorder during which histamine released into the circulation causes vasodilation as well as increased permeability of the capillaries with resultant marked loss of plasma from the circulation. Anaphylaxis can occur systemically, with the associated effects experienced over the entire body, and it can occur locally, with the reaction limited to a specific target tissue or organ.

An "IgE associated disorder" is a physiological condition which is characterized, in part, by elevated IgE levels, which may or may not be persistent. IgE associated disorders include, but are not limited to, allergy and allergic reactions, allergy-related disorders (described below), asthma, rhinitis, conjunctivitis, urticaria, shock, hymenoptera sting allergies, and drug allergies, and parasite infections. The term also includes related manifestations of these disorders. Generally, IgE in such disorders is antigen-specific.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder. Especially in the allergy context, as is well understood by those skilled in the art, palliation may occur upon modulation of the immune response against an allergen(s). Further, palliation does not necessarily occur by administration of one dose, but often occurs upon administration of a series of doses. Thus, an amount sufficient to palliate a response or disorder may be administered in one or more administrations.

An "antibody titer", or "amount of antibody", which is "elicited" by an ISS-conjugate partner or ISS-antigen refers to the amount of a given antibody measured at a time point after administration of conjugate or antigen.

A "Th1-associated antibody" is an antibody whose production and/or increase is associated with a Th1 immune response. For example, IgG2a is a Th1-associated antibody in mouse. For purposes of this invention, measurement of a Th1-associated antibody can be a measurement of one or more such antibodies. For example, in human, measurement of a Th1-associated antibody could entail measurement of IgG1 and/or IgG3.

A "Th2-associated antibody" is an antibody whose production and/or increase is associated with a Th2 immune response. For example, IgG1 is a Th2-associated antibody in mouse. For purposes of this invention, measurement of a Th2-associated antibody can be measurement of one or more such antibodies. For example, in human, measurement of a Th2-associated antibody could entail measurement of IgG2 and/or IgG4.

To "suppress" or "inhibit" a function or activity, such as cytokine production, antibody production, or histamine release, is to reduce the function or activity when compared to otherwise same conditions except for a condition or parameter of interest, or alternatively, as compared to another condition. For example, a conjugate molecule population which suppresses histamine release reduces histamine release as compared to, for example, histamine release induced by antigen alone. As another example, a conjugate molecule population which suppresses antibody production reduces extent and/or levels of antibody as compared to, for example, extent and/or levels of antibody produced by antigen alone.

Compositions Comprising Conjugate Molecules

The present invention relates, in part, to compositions comprising a conjugate molecule, wherein the conjugate molecule comprises a conjugate partner and a polynucleotide comprising an immunostimulatory sequence (ISS) and, in part, to methods of making and using such compositions. The present invention also relates, in part, to compositions comprising structurally stable conjugate molecules and methods of making and using such compositions. ISS and conjugate partners encompassed within the present invention are described herein. As will be appreciated by one of skill in the art, conjugate molecules encompassed within the present invention may have differing and distinct biological properties, based on the conjugate partner, the type and number of ISS present in the conjugate molecule and the average extent of conjugation between the ISS and conjugate partner. In some examples, a conjugate partner is a protein, such as an antigen or an allergen. In some examples, the conjugate partner comprises the allergen, Amb a 1. In other examples, the ISS can be a polynucleotide of any length greater than 6 bases or base pairs and in some examples comprises the sequence 5'-cytosine (C), guanine-3' (G), and in other examples comprises the sequence 5'-purine, purine, C, G, pyrimidine, pyrimidine-3' (such as 5'-AACGTT-3'), and in other examples is greater than 15 bases or base pairs, and in other examples is greater than 20 bases or base pairs in length. In some examples, an ISS comprises the sequence 5'-purine, purine, C, G, pyrimidine, pyrimidine, C, G-3'; or the sequence 5'-purine, purine, C, G, pyrimidine, pyrimidine, C, C-3'; or the sequence 5'-T, C, G-3'. In some examples, the ISS comprises 5-TGACTGTGAACGTTCGAGATGA-3' (SEQ ID NO:1').

In some examples, the conjugate molecule comprises Amb a 1 conjugated to an ISS comprising 5'-TGACTGTGAACGTTCGAGATGA-3' (SEQ ID NO:1). Such compositions find use, for example, in therapeutic and diagnostic methods where maintaining the structural stability of conjugate molecules is critical. Conjugate molecules containing an immunostimulatory sequence (ISS) linked to an antigen are disclosed in PCT publication WO 01/35991, WO 98/16247 and WO 01/12223, the disclosures of which are specifically incorporated herein in their entirety by reference.

The inventors discovered that the structural stability of a conjugate molecule within a composition is dependent upon temperature, salt and pH conditions. It was found that a conjugate molecule comprising an allergen was destabilized in a liquid composition at temperatures above 0 degrees C. or higher by the presence of sodium phosphate, sodium chloride, negatively charged components and/or polar components in a composition. It was found that low pH caused a conjugate molecule comprising an allergen to aggregate reversibly under conditions of low ionic strength.

Without being bound by theory, it is believed that due to the negative charge of the conjugate molecule, by virtue of the presence of an ISS, compositions comprising non-negatively charged components or components having a neutral charge or non-polar components are desired to maintain the structural stability of the conjugate molecule present in the composition. It has been found that the addition of components having a negative charge, such as sodium chloride, will cause the conjugate molecules comprising an ISS to aggregate, thereby becoming destabilized. It has been found that the presence of nucleophiles, such as azides, or even low sodium chloride in a composition comprising a conjugate molecule will destabilize the conjugate molecule.

The structural stability of a conjugate molecule comprising an allergen within various compositions was characterized as described herein. Experiments were designed to elucidate possible structural changes in conjugate molecules within compositions as a function of pH, temperature, time and composition conditions, such as ionic strength, and presence of surfactants. As described herein, an illustrative example of a conjugate molecule comprising a purified short ragweed antigen, AMB a 1, covalently linked to an ISS (referred to herein as Amb a 1-ISS Oligonucleotide Conjugate or "AIC") within a concentration range of about 0.1 μg to 200 μg was dialyzed into compositions containing varying ionic strengths and varying pH conditions and then analyzed by using intrinsic fluorescence (IF); extrinsic fluorescence (EF); and right angle light scatter (RALS) while subjecting the conjugate molecule to temperature variations. IF, EF, and RALS are described herein in the Examples. The conjugate molecule was subjected to shear stress and analyzed by RALS and size exclusion chromatograph HPLC (SEC-HPLC). The same methods, that is, IF, EF, RALS, and SEC-HPLC, were used in parallel to examine freeze-thaw sensitivity of a composition comprising AIC in the presence of sodium phosphate and sodium chloride (referred to herein in the Examples as PBS).

The results of the experiments designed to elucidate structural changes in AIC within compositions are described herein, including in the Examples and in Tables 10, 11 and 12. Table 10 shows the results of analysis of various components for maintaining pH conditions. Accordingly, in some examples, components for maintaining pH conditions of a composition comprising a conjugate molecule include Histidine at pH 7.5, Histidine at pH 8.0, Phosphate at pH 7.5, Phosphate at pH 8.0, Phosphate at pH 7.0, Histidine at pH 7.0 or Histidine at pH 6.5. As described herein, for combination studies, that is combinations of components in a composition comprising a conjugate molecule, compositions were prepared that comprised Histidine. Table 11 shows the results of analysis of various amino acids. Accordingly, in some examples, amino acids for use in a composition comprising a conjugate molecule include Histidine, Glycine, Isoleucine, Leucine, Proline, or Alanine. For combination studies, that is combinations of components in a composition comprising a conjugate molecule, compositions were prepared that comprised Glycine. Table 12 shows the results of analysis of various carbohydrates. Accordingly, in some examples, a composition comprising a conjugate molecule includes a carbohydrate, such as Lactose, Sucrose, Mannose or Maltose. Example 6 describes results of combination studies.

Provided herein are compositions comprising a structurally stable conjugate molecule at a temperature of between about 2 degrees C. and about 8 degrees C. In some examples, the composition is in liquid form and in other examples is in a lyophilized form. Provided herein are compositions comprising a structurally stable conjugate molecule and a component capable of maintaining the pH of the composition in the range of about 6.0 to about 9.0. In some examples, the component is capable of maintaining the pH in the range of about 7.0 to about 8.0, and in other examples, in the range of about 7.5 to about 7.8, and in other examples, at a pH of about 7.5. In some examples, the component capable of maintaining the pH in the range of about 6.0 to about 9.0 has a neutral charge or basic charge. In some examples, the component capable of maintaining the pH in the range of about 6.0 to about 9.0 is non-polar. In some examples, a component capable of maintaining the pH of the composition in the range of about 6.0 to about 9.0 is selected from the group consisting of Histidine or Phosphate. In some examples, the component capable of maintaining the pH is present in the composition in an amount sufficient to retain more than 70%, more than 80%, more then 90%, more then 95% or more than 97% of said conjugate molecule in non-aggregate form at a temperature of between about 2 degrees C. and about 8 degrees C. Aggregation of conjugate molecules can be measured by methods disclosed herein, such as by Right Angle Light Scatter (RALS), and by methods known in the art.

In other examples, a composition comprising a conjugate molecule may further comprise one or more of 1) an amino acid, 2) a carbohydrate, 3) a surfactant, and 4) other suitable pharmaceutically acceptable carriers as long as the composition comprises more than 70%, more than 80%, more then 90%, more then 95% or more than 97% of said conjugate molecule in non-aggregate or monomer form. In some examples, the amino acid is selected from the group consisting of Histidine, Glycine, Isoleucine, Leucine, Proline and Alanine. In some examples, the amino acid is Histidine or Glycine. In some examples, the carbohydrate is selected from the group consisting of Lactose, Sucrose, Mannose, Maltose, Sorbitol and Glucose. In some examples, the carbohydrate is Sorbitol or Sucrose. Provided herein are compositions comprising a structurally stable conjugate molecule and a component capable of maintaining the pH of the composition in the range of about 6.0 to about 9.0. Provided herein are compositions comprising a structurally stable conjugate molecule, a component capable of maintaining the pH of the composition in the range of about 6.0 to about 9.0, and an amino acid. Provided herein are compositions comprising a structurally stable conjugate molecule, a component capable of maintaining the pH of the composition in the range of about 6.0 to about 9.0, and a carbohydrate. Provided herein are compositions comprising a structurally stable conjugate molecule, a component capable of maintaining the pH of the composition in the range of about 6.0 to about 9.0, an amino acid and a carbohydrate. In some examples, a composition comprising a structurally stable conjugate molecule further comprises a surfactant. In some examples, the composition is in liquid form and in other examples is in lyophilized form. The present invention encompasses compositions comprising conjugate molecules reconstituted in liquid form from a lyophilized form.

As described herein, an assessment of various compositions in liquid form comprising AIC as described herein at concentrations including about 30 ug/ml and about 60 ug/ml, and comprising an average of about 4.0 moles of ISS per mole of Amb 1 a (average molecular weight of about 65kDA) identified compositions that maintain structural stability of the AIC at a temperature of between about 2 degrees C. and 8 degrees C. In some examples, the structural stability was maintained for at least 6 months. These compositions comprising AIC include, but are not limited to compositions comprising Histidine in the range of about 1 mM to about 50 mM; compositions comprising Histidine in the range of about 1 mM to about 50 mM and Glycine in the range of about 50 mM to about 300 mM; compositions comprising Histidine in the range of about 1 mM to about 50 mM and Sorbitol in the range of about 1% to about 5% of the composition; compositions comprising Histidine in the range of about 1 mM to about 50 mM, Glycine in the range of about 50 mM to about 300 mM, and Sorbitol in the range of about 1% to about 5% of the composition, all of which compositions have a pH in the range of about 7.0 to about 8.0. Provided herein are compositions comprising AIC (which may be low (L), medium(M) or high(H), as described herein) wherein the AIC within the composition is structurally stable at a temperature of between about 2 degrees C. and 8 degrees C. which include, but are not limited to:

- 5 mM Histidine, 285 mM Glycine at a pH range of between about 7.0 and about 8.0 or at about pH 7.5;
- 20 mM Histidine, 270 mM Glycine at a pH range of between about 7.0 and about 8.0 or at about pH 7.5;
- 20 mM Histidine, 50 mM Glycine, 3.8% Sorbitol at a pH range of between about 7.0 and about 8.0 or at about pH 7.5; and
- 20 mM Histidine, 50 mM Glycine, 210 mM Sucrose at a pH range of between about 7.0 and about 8.0 or at about pH 7.5.

Based on experimental results disclosed herein, additional compositions of AIC that are predicted to be structurally stable are shown below.

| Composition No. (Comp. #) | Conjugate Molecule | Component to Maintain pH; pH conditions | Amino Acid Component | Carbohydrate | State of Composition/ Temp. |
|---|---|---|---|---|---|
| 1. | AIC in a Conc. range of about 0.1 μg to about 200 μg. | Histidine Conc. about 5 mm to about 20 mm pH between about 6.5 to about 8.0 pH at about 7.5 pH at about 8.0 | | | Liquid/about 2° C. to about 8° C. |
| 2. | AIC as in comp. 1 | Histidine as in comp. 1 | Glycine Conc. about 50 mm to about 300 mm | | Same as comp. 1 |
| 3. | AIC as in comp. 1 | Histidine as in comp. 1 | Glycine as in comp. 2 | Sorbitol at about 1% to about 10% | Same as comp. 1 |
| 4. | AIC as in comp. 1 | Histidine as in comp. 1 | Glycine as in comp. 2 | Sorbitol as in comp. 3 | Lyophilized/ about 2° C. to about 8° C. lyophilized/at or less than 0° C. |
| 5. | AIC as in comp. 1 | Histidine as in comp. 1 | Glycine as in comp. 2 | Sucrose at about 200 mm-to about 250 mm | Same as comp. 1 |
| 6. | AIC as in comp. 1 | Histidine as in comp. 1 | Glycine as in comp. 2 | Sucrose as in comp. 5 | Lyophilized/ about 2° C. to about 8° C. lyophilized/at or less than 0° C. |
| 7. | AIC as in comp. 1 | Histidine as in comp. 1 | Isoleucine, Leucine, Proline or Alanine at a conc. of between about 50 mm to about 300 mm | | Same as comp. 1 |
| 8. | AIC as in comp. 1 | Histidine as in comp. 1 | Amino acids as in comp. 7 | Sorbitol as in comp. 3 or sucrose as in comp. 5. | Lyophilized/ about 2° C. to about 8° C. lyophilized/at or less than 0° C. liquid/about 2° C. to about 8° C. |

IF, EF and RALS in conjunction with analytical HPLC methods, such as, Size Exclusion (SEC-HPLC) and SDS-PAGE, for example, can be designed to profile the behavior of any conjugate molecule within a composition as a function of pH, temperature and time as well as solution conditions (i.e. ionic strength, surfactants, etc.) to determine conditions for structural stability of a conjugate molecule within a composition.

Conjugate Partners

Conjugate partners encompassed within the present invention include but are not limited to antigens, such as peptides, proteins, glycoproteins, polysaccharides, complex carbohydrates, sugars, gangliosides, lipids and phospholipids; portions thereof and combinations thereof. In some examples, the antigen can be from an infectious agent, including protozoan, bacterial, fungal (including unicellular and multicellular), and viral infectious agents. For example, antigens from parasitic organisms include schistosome egg antigens (e.g., Sm-p40) from Schistosome species (e.g., S. mansoni) and antigens from Toxoplasma species (e.g., T. gondii). See, for example, Stadecker et al. (1998) Parasite Immunol. 20:217-221; Subauste et al. (1993) Curr. Opin. Immunol. 5:532-527. Antigens may be isolated from their source using purification techniques known in the art or, more conveniently, may be produced using recombinant methods. Antigenic peptides can include purified native peptides, synthetic peptides, recombinant proteins, crude protein extracts, attenuated or inactivated viruses, cells, micro-organisms, or fragments of such peptides. Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) Hoppe Seylers Z. Physiol. Chem. 362:833-839. Proteolytic enzymes can also be utilized to couple amino acids to produce peptides. Alternatively, the peptide can be obtained by using the biochemical machinery of a cell, or by isolation from a biological source. Recombinant DNA techniques can be employed for the production of peptides. Peptides can also be isolated using standard techniques such as affinity chromatography. Generally, the antigens are peptides, lipids (e.g., sterols excluding cholesterol, fatty acids, and phospholipids), polysaccharides, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available. Antigens derived from infectious agents may be obtained using methods known in the art, for example, from native viral or bacterial extracts, from cells infected with the infectious agent, from purified polypeptides, from recombinantly produced polypeptides and/or as synthetic peptides.

In some examples, the antigen is an allergen. Examples of recombinant allergens are provided in Table 1 and include but are not limited to Crustacea allergens, insect allergens, mammalian allergens, mollusks allergens, plant allergens, and fungal allergens. In some examples, the allergen is a plant allergen. In other examples, the allergen is the ragweed antigen Amb a 1. Preparation of many allergens is well-known in the art, including, but not limited to, preparation of ragweed pollen allergen Antigen E (Amb aI) (Rafnar et al. (1991) J. Biol. Chem. 266:1229-1236), major dust mite allergens DerpI and Der PII (Chua et al. (1988) J. Exp. Med. 167:175-182; Chua et al. (1990) Int. Arch. Allergy Appl. Immunol. 91:124-129), white birch pollen Bet vl (Breiteneder et al. (1989) EMBO J. 8:1935-1938), domestic cat allergen Fel d I (Rogers et al. (1993) Mol. Immunol. 30:559-568), and protein antigens from tree pollen (Elsayed et al. (1991) Scand. J. Clin. Lab. Invest. Suppl. 204:17-31). As indicated, allergens from trees are known, including allergens from birch, juniper and Japanese cedar. Preparation of protein antigens from grass pollen for in vivo administration has been reported. Malley (1989) J. Reprod. Immunol. 16:173-186. As Table 1 indicates, in some examples, the allergen is a food allergen such as peanut allergen, for example Ara h I, and in some examples, the allergen is a grass allergen such as a rye allergen, for example Lol p I. Table 1 shows a list of allergens encompassed within the present invention.

TABLE 1

RECOMBINANT ALLERGENS

| Group | Allergen | Reference |
|---|---|---|
| ANIMALS: CRUSTACEA | | |
| Shrimp/lobster | tropomyosin | Leung et al. J. Allergy Clin. Immunol., 1996, 98: 954-961 |
| | Pan s I | Leung et al. Mol. Mar. Biol. Biotechnol., 1998, 7: 12-20 |
| INSECTS | | |
| Ant | Sol i 2 (venom) | Schmidt et al. J Allergy Clin Immunol., 1996, 98: 82-8 |
| Bee | phospholipase A2 (PLA) | Muller et al. J Allergy Clin Immunol, 1995, 96: 395-402<br>Forster et al. J Allergy Clin Immunol, 1995, 95: 1229-35<br>Muller et al. Clin Exp Allergy, 1997, 27: 915-20 |
| | Hyaluronidase (Hya) | Soldatova et al. J Allergy Clin Immunol, 1998, 101: 691-8 |
| Cockroach | Bla g Bd9OK | Helm et al. J Allergy Clin Immunol, 1996, 98: 172-80 |
| | Bla g 4 (a calycin) | Vailes et al. J Allergy Clin Immunol, 1998, 101: 274-80 |
| | glutathione 5-transferase | Arruda et al. J Biol Chem, 1997, 272: 20907-12 |
| | Per a 3 | Wu et al. Mol Immunol, 1997, 34: 1-8 |
| Dust mite | Der p 2 (major allergen) | Lynch et al. J Allergy Clin Immunol, 1998, 101: 562-4<br>Hakkaart et al. Clin Exp Allergy, 1998, 28: 169-74<br>Hakkaart et al. Clin Exp Allergy, 1998, 28: 45-52<br>Hakkaart et al. Int Arch Allergy Immunol, 1998, 115 (2): 150-6<br>Mueller et al. J Biol Chem, 1997, 272: 26893-8 |
| | Der p 2 variant | Smith et al. J Allergy Clin Immunol, 1998, 101: 423-5 |
| | Der f 2 | Yasue et al. Clin Exp Immunol, 1998, 113: 1-9<br>Yasue et al. Cell Immunol, 1997, 181: 30-7 |
| | Der p 10 | Asturias et al. Biochim Biophys Acta, 1998, 1397: 27-30 |
| | Tyr p 2 | Eriksson et al. Eur J Biochem, 1998 |
| Hornet | Antigen 5 aka Dol m V (venom) | Tomalski et al. Arch Insect Biochem Physiol, 1993, 22: 303-13 |
| Mosquito | Aed a I (salivary apyrase) | Xu et al. Int Arch Allergy Immunol, 1998, 115: 245-51 |
| Yellow jacket | antigen 5, hyaluronidase, and phospholipase (venom) | King et al. J Allergy Clin Immunol, 1996, 98: 588-600 |
| MAMMALS | | |
| Cat | Fel d I | Slunt et al. J Allergy Clin Immunol, 1995, 95: 1221-8<br>Hoffmann et al. J Allergy Clin Immunol, 1997, 99: 227-32<br>Hedlin Curr Opin Pediatr, 1995, 7: 676-82 |
| Cow | Bos d 2 (dander; a lipocalin) | Zeiler et al. J Allergy Clin Immunol, 1997, 100: 721-7<br>Rautiainen et al. Biochem Bioph. Res Comm., 1998, 247: 746-50 |
| | β-lactoglobulin (BLG, major cow milk allergen) | Chatel et al. Mol Immunol, 1996, 33: 1113-8<br>Lehrer et al. Crit Rev Food Sci Nutr, 1996, 36: 553-64 |
| Dog | Can f I and Can f 2, salivary lipocalins | Konieczny et al. Immunology, 1997, 92: 577-86<br>Spitzauer et al. J Allergy Clin Immunol, 1994, 93: 614-27<br>Vrtala et al. J Immunol, 1998, 160: 6137-44 |
| Horse | Equ c1 (major allergen, a lipocalin) | Gregoire et al. J Biol Chem, 1996, 271: 32951-9 |
| Mouse | mouse urinary protein (MUP) | Konieczny et al. Immunology, 1997, 92: 577-86 |
| OTHER MAMMALIAN ALLERGENS | | |
| Insulin | | Ganz et al. J Allergy Clin Immunol, 1990, 86: 45-51<br>Grammer et al. J Lab Clin Med, 1987, 109: 141-6<br>Gonzalo et al. Allergy, 1998, 53: 106-7 |
| Interferons | interferon alpha 2c | Detmar et al. Contact Dermatis, 1989, 20: 149-50 |
| MOLLUSCS | topomyosin | Leung et al. J Allergy Clin Immunol, 1996, 98: 954-61 |
| PLANT ALLERGENS: | | |
| Barley | Hor v 9 | Astwood et al. Adv Exp Med Biol, 1996, 409: 269-77 |

TABLE 1-continued

| RECOMBINANT ALLERGENS | | |
|---|---|---|
| Group | Allergen | Reference |
| Birch | pollen allergen, Bet v 4 | Twardosz et al. Biochem Bioph. Res Comm., 1997, 239: 197 |
| | rBet v 1 Bet v 2: (profilin) | Pauli et al. J Allergy Clin Immunol, 1996, 97: 1100-9<br>van Neerven et al. Clin Exp Allergy, 1998, 28: 423-33<br>Jahn-Schmid et al. Immunotechnology, 1996, 2: 103-13<br>Breitwieser et al. Biotechniques, 1996, 21: 918-25<br>Fuchs et al. J Allergy Clin Immunol, 1997, 100: 356-64 |
| Brazil nut | globulin | Bartolome et al. Allergol Immunopathol, 1997, 25: 135-44 |
| Cherry | Pru a I (major allergen) | Scheurer et al. Mol Immunol, 1997, 34: 619-29 |
| Corn | Zml3 (pollen) | Heiss et al. FEBS Lett, 1996, 381: 217-21<br>Lehrer et al. Int Arch Allergy Immunol, 1997, 113: 122-4 |
| Grass | Phl p 1, Phl p 2, Phl p 5 (timothy grass pollen) | Bufe et al. Am J Respir Crit Care Med, 1998, 157: 1269-76<br>Vrtala et al. J Immunol Jun 15, 1998, 160: 6137-44<br>Niederberger et al. J Allergy Clin Immun., 1998, 101: 258-64 |
| | Hol 1 5 velvet grass pollen | Schramm et al. Eur J Biochem, 1998, 252: 200-6 |
| | Bluegrass allergen | Zhang et al. J Immunol, 1993, 151: 791-9 |
| | Cyn d 7 Bermuda grass | Smith et al. Int Arch Allergy Immunol, 1997, 114: 265-71 |
| | Cyn d 12 (a profilin) | Asturias et al. Clin Exp Allergy, 1997, 27: 1307-13<br>Fuchs et al. J Allergy Clin Immunol, 1997, 100: 356-64 |
| Juniper | Jun o 2 (pollen) | Tinghino et al. J Allergy Clin Immunol, 1998, 101: 772-7 |
| Latex | Hey b 7 | Sowka et al. Eur J Biochem, 1998, 255: 213-9<br>Fuchs et al. J Allergy Clin Immunol, 1997, 100:3 56-64 |
| Mercurialis | Mer a I (profilin) | Vallverdu et al. J Allergy Clin Immunol, 1998, 101:3 63-70 |
| Mustard (Yellow) | Sin a I (seed) | Gonzalez de la Pena et al. Biochem Bioph. Res Comm., 1993, 190: 648-53 |
| Oilseed rape | Bra r I pollen allergen | Smith et al. Int Arch Allergy Immunol, 1997, 114: 265-71 |
| Peanut | Ara h I | Stanley et al. Adv Exp Med Biol, 1996, 409: 213-6<br>Burks et al. J Clin Invest, 1995, 96: 1715-21<br>Burks et al. Int Arch Allergy Immunol, 1995, 107: 248-50 |
| Poa pratensis | Poa p9 | Parronchi et al. Eur J Immunol, 1996, 26: 697-703<br>Astwood et al. Adv Exp Med Biol, 1996, 409: 269-77 |
| Ragweed | Amb a I | Sun et al. Biotechnology Aug, 1995, 13: 779-86<br>Hirschwehr et al. J Allergy Clin Immunol, 1998, 101: 196-206<br>Casale et al. J Allergy Clin Immunol, 1997, 100: 110-21 |
| Rye | Lol p I | Tamborini et al. Eur J Biochem, 1997, 249: 886-94 |
| Walnut | Jug r I | Teuber et al. J Allergy Clin Immun., 1998, 101: 807-14 |
| Wheat | allergen | Fuchs et al. J Allergy Clin Immunol, 1997, 100: 356-64<br>Donovan et al. Electrophoresis, 1993, 14: 917-22 |

TABLE 1-continued

| RECOMBINANT ALLERGENS | | |
|---|---|---|
| Group | Allergen | Reference |
| FUNGI: | | |
| Aspergillus | Asp f 1, Asp f 2, Asp f3, Asp f 4, rAsp f 6 | Crameri et al. Mycoses, 1998, 41 Suppl 1:56-60<br>Hemmann et al. Eur J Immunol, 1998, 28: 1155-60<br>Banerjee et al. J Allergy Clin Immunol, 1997, 99: 821-7<br>Crameri Int Arch Allergy Immunol, 1998, 115: 99-114<br>Crameri et al. Adv Exp Med Biol, 1996, 409: 111-6<br>Moser et al. J Allergy Clin Immunol, 1994, 93: 1-11 |
| | Manganese superoxide dismutase (MNSOD) | Mayer et al. Int Arch Allergy Immunol, 1997, 113: 213-5 |
| Blomia | allergen | Caraballo et al. Adv Exp Med Biol, 1996, 409: 81-3 |
| Penicillinium | allergen | Shen et al. Clin Exp Allergy, 1997, 27: 682-90 |
| Psilocybe | Psi c 2 | Horner et al. Int Arch Allergy Immunol, 1995, 107: 298-300 |

In some examples, the antigen is from an infectious agent, including protozoan, bacterial, fungal (including unicellular and multicellular), and viral infectious agents. Examples of suitable viral antigens are described herein and are known in the art. Bacteria include Hemophilus influenza, Mycobacterium tuberculosis and Bordetella pertussis. Protozoan infectious agents include malarial plasmodia, Leishmania species, Trypanosoma species and Schistosoma species. Fungi include Candida albicans.

In some examples, the antigen is a viral antigen. Viral polypeptide antigens include, but are not limited to, core proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein. References discussing influenza vaccination include Scherle and Gerhard (1988) Proc. Natl. Acad. Sci. USA 85:4446-4450; Scherle and Gerhard (1986) J. Exp. Med. 164:1114-1128; Granoff et al. (1993) Vaccine 11:S46-51; Kodihalli et al. (1997) J. Virol. 71:3391-3396; Ahmeida et al. (1993) Vaccine 11:1302-1309; Chen et al. (1999) Vaccine 17:653-659; Govorkova and Smirnov (1997) Acta Virol. (1997) 41:251-257; Koide et al. (1995) Vaccine 13:3-5; Mbawuike et al. (1994) Vaccine 12:1340-1348; Tamura et al. (1994) Vaccine 12:310-316; Tamura et al. (1992) Eur. J. Immunol. 22:477-481; Hirabayashi et al. (1990) Vaccine 8:595-599. Other examples of antigen polypeptides are group- or sub-group specific antigens, which are known for a number of infectious agents, including, but not limited to, adenovirus, herpes simplex virus, papilloma virus, respiratory syncytial virus and poxviruses.

Many antigenic peptides and proteins are known, and available in the art; others can be identified using conventional techniques. For immunization against tumor formation, immunomodulatory peptides can include tumor cells (live or irradiated), tumor cell extracts, or protein subunits of tumor antigens such as Her-2/neu, Mart1, carcinoembryonic antigen (CEA), gangliosides, human milk fat globule (HMFG), mucin (MUC1), MAGE antigens, BAGE antigens, GAGE antigens, gp100, prostate specific antigen (PSA), and tyrosinase. Vaccines for immuno-based contraception can be formed by including sperm proteins administered with ISS. Lea et al. (1996) Biochim. Biophys. Acta 1307:263.

Attenuated and inactivated viruses are suitable for use herein as the antigen. Preparation of these viruses is well-known in the art and many are commercially available (see, e.g., Physicians' Desk Reference (1998) 52nd edition, Medical Economics Company, Inc.). For example, polio virus is available as IPOL® (Poliovirus Vaccine Inactivated, Pasteur Merieux Connaught) and ORIMUNE® (Oral Poliovirus Vaccine, Lederle Laboratories), hepatitis A virus as VAQTA® Hepatitis A Vaccine, Inactivated, Merck), measles virus as ATTENUVAX® (Measles Virus Vaccine Live, Merck), mumps virus as MUMPSVAX® (Mumps Virus Vaccine Live, Merck) and rubella virus as MERUVAX®II (Rubella Virus Vaccine Live, Merck). Additionally, attenuated and inactivated viruses such as HIV-1, HIV-2, herpes simplex virus, hepatitis B virus, rotavirus, human and non-human papillomavirus and slow brain viruses can provide peptide antigens.

In some examples, the antigen comprises a viral vector, such as vaccinia, adenovirus, and canary pox.

Antigens may be isolated from their source using purification techniques known in the art or, more conveniently, may be produced using recombinant methods.

Antigenic peptides can include purified native peptides, synthetic peptides, recombinant proteins, crude protein extracts, attenuated or inactivated viruses, cells, micro-organisms, or fragments of such peptides. Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) Hoppe Seylers Z. Physiol. Chem. 362: 833-839. Proteolytic enzymes can also be utilized to couple amino acids to produce peptides. Kullmann (1987) Enzymatic Peptide Synthesis, CRC Press, Inc. Alternatively, the peptide can be obtained by using the biochemical machinery of a cell, or by isolation from a biological source. Recombinant DNA techniques can be employed for the production of peptides. Hames et al. (1987) Transcription and Translation. A Practical Approach, IRL Press. Peptides can also be isolated using standard techniques such as affinity chromatography.

In some examples, the antigens are peptides, lipids (e.g., sterols, fatty acids, and phospholipids), polysaccharides such as those used in H. influenza vaccines, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

Examples of viral antigens useful in the subject compositions and methods using the compositions include, but are not limited to, HIV antigens. Such antigens include, but are not limited to, those antigens derived from HIV envelope glycoproteins including, but not limited to, gp 160, gp 120 and gp41. Numerous sequences for HIV genes and antigens are known. For example, the Los Alamos National Laboratory HIV Sequence Database collects, curates and annotates HIV nucleotide and amino acid sequences. This database is accessible via the internet and in a yearly publication, see Human Retroviruses and AIDS Compendium (for example, 1998 edition).

Antigens derived from infectious agents may be obtained using methods known in the art, for example, from native viral or bacterial extracts, from cells infected with the infectious agent, from purified polypeptides, from recombinantly produced polypeptides and/or as synthetic peptides.

ISS

In accordance with the present invention, the conjugate molecule contains at least one ISS, and can contain multiple ISSs. The ISSs can be adjacent within the polynucleotide, or they can be separated by additional nucleotide bases within the polynucleotide.

ISS have been described in the art and may be readily identified using standard assays which indicate various aspects of the immune response, such as cytokine secretion, antibody production, NK cell activation and T cell proliferation. See, e.g., WO 97/28259; WO 98/16247; WO 99/11275; Krieg et al. (1995) Nature 374:546-549; Yamamoto et al. (1992a); Ballas et al. (1996); Klinman et al. (1997); Sato et al. (1996); Pisetsky (1996a); Shimada et al. (1986) Jpn. J. Cancer Res. 77:808-816; Cowdery et al. (1996) J. Immunol. 156: 4570-4575; Roman et al. (1997); and Lipford et al. (1997a).

The ISS can be of any length greater than 6 bases or base pairs and generally comprises the sequence 5'-cytosine, guanine-3', more particularly comprises the sequence 5'-purine, purine, C, G, pyrimidine, pyrimidine-3' (such as 5'-AACGTT-3'), preferably, in some examples, greater than 15 bases or base pairs, more preferably, in some examples, greater than 20 bases or base pairs in length. An ISS may also comprise the sequence 5'-purine, purine, C, G, pyrimidine, pyrimidine, C, G-3'. An ISS may also comprise the sequence 5'-purine, purine, C, G, pyrimidine, pyrimidine, C, C-3'. As indicated in polynucleotide sequences below, an ISS may also comprise the sequence 5'-T, C, G-3'.

In some examples, the ISS comprises any of the following sequences:

GACGCTCC;

GACGTCCC;

GACGTTCC;

GACGCCCC;

AGCGTTCC;

AGCGCTCC;

AGCGTCCC;

AGCGCCCC;

AACGTCCC;

AACGCCCC;

AACGTTCC;

AACGCTCC;

GGCGTTCC;

GGCGCTCC;

GGCGTCCC;

GGCGCCCC;

GACGCTCG;

GACGTCCG;

GACGCCCG;

GACGTTCG;

AGCGCTCG;

AGCGTTCG;

AGCGTCCG;

AGCGCCCG;

AACGTCCG;

AACGCCCG;

AACGTTCG;

AACGCTCG;

GGCGTTCG;

GGCGCTCG;

GGCGTCCG;

GGCGCCCG.

In some examples, the ISS comprises any of the following sequences:

GACGCT;

GACGTC;

GACGTT;

GACGCC;

GACGCU;

GACGUC;

GACGUU;

GACGUT;

GACGTU;

AGCGTT;

AGCGCT;

AGCGTC;

AGCGCC;

AGCGUU;

AGCGCU;

AGCGUC;

AGCGUT;

AGCGTU;

AACGTC;

AACGCC;

AACGTT;

AACGCT;

AACGUC;

AACGUU;

AACGCU;

AACGUT;

AACGTU;

GGCGTT;

GGCGCT;

GGCGTC;

GGCGCC;

GGCGUU;

GGCGCU;

GGCGUC;

GGCGUT;

GGCGTU.

In some examples, the immunomodulatory polynucleotide comprises the sequence 5'-TGACTGTGAACGTTC-GAGATGA-3' (SEQ ID NO: 1). In other examples, the ISS comprises any of the sequences:

5'-TGACCGTGAACGTTCGAGATGA-3'; (SEQ ID NO: 2)

5'-TCATCTCGAACGTTCCACAGTCA-3'; (SEQ ID NO: 3)

5'-TGACTGTGAACGTTCCAGATGA-3'; (SEQ ID NO: 4)

5'-TCCATAACGTTCGCCTAACGTTCGTC-3'; (SEQ ID NO: 5)

5'-TGACTGTGAABGTTCCAGATGA-3', (SEQ ID NO: 6)

where B is 5-bromocytosine; 5'-TGACTGTGAABGTTC-GAGATGA-3' (SEQ ID NO:7), where B is 5-bromocytosine and 5'-TGACTGTGAABGTTBGAGATGA-3' (SEQ ID NO:8), where B is 5-bromocytosine.

An ISS and/or ISS-containing polynucleotide may contain modifications. Modifications of ISS include any known in the art, but are not limited to, modifications of the 3'OH or 5'OH group, modifications of the nucleotide base, modifications of the sugar component, and modifications of the phosphate group. Various such modifications are described below.

An ISS may be single stranded or double stranded DNA, as well as single or double-stranded RNA or other modified polynucleotides. An ISS may or may not include one or more palindromic regions, which may be present in the hexameric motif described above or may extend beyond the motif. An ISS may comprise additional flanking sequences, some of which are described herein. An ISS may contain naturally-occurring or modified, non-naturally occurring bases, and may contain modified sugar, phosphate, and/or termini. For example, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. In some examples, oligonucleotides of the present invention comprise phosphorothioate backbones. Sugar modifications known in the field, such as 2'-alkoxy-RNA analogs, 2'-amino-RNA analogs and 2'-alkoxy- or amino-RNA/DNA chimeras and others described herein, may also be made and combined with any phosphate modification. Examples of base modifications include, but are not limited to, addition of an electron-withdrawing moiety to C-5 and/or C-6 of a cytosine of the ISS (e.g., 5-bromocytosine, 5-chlorocytosine, 5-fluorocytosine, 5-iodocytosine).

The ISS can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an oligonucleotide to a nuclease, as exemplified in U.S. Pat. No. 4,650,675.

The ISS can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular ISS can be isolated, synthesized through recombinant methods, or chemically synthesized. Where the circular ISS is obtained through isolation or through recombinant methods, the ISS will in some examples be a plasmid. The chemical synthesis of smaller circular oligonucleotides can be performed using any method described in the literature. See, for instance, Gao et al. (1995) Nucleic Acids Res. 23:2025-2029; and Wang et al. (1994) Nucleic Acids Res. 22:2326-2333.

The techniques for making oligonucleotides and modified oligonucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in Protocols for Oliognucleotides and Analogs, Synthesis and Properties (Agrawal, ed.) Humana Press, Totowa, N.J.; Warner et al. (1984) DNA 3:401 and U.S. Pat. No. 4,458,066.

The ISS can also contain phosphate-modified oligonucleotides. Synthesis of polynucleotides containing modified phosphate linkages or non-phosphate linkages is also know in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, NY. The phosphorous derivative (or modified phosphate group) which can be attached to the sugar or sugar analog moiety in the oligonucleotides of the present invention can be a monophosphate, diphosphate, triphosphate, alkylphosphonate, phosphorothioate, phosphorodithioate or the like. The preparation of the above-noted phosphate analogs, and their incorporation into nucleotides, modified nucleotides and oligonucleotides, per se, is also known and need not be described here in detail. Peyrottes et al. (1996) Nucleic Acids Res. 24:1841-1848; Chaturvedi et al. (1996) Nucleic Acids Res. 24:2318-2323; and Schultz et al. (1996) Nucleic Acids Res. 24:2966-2973. For example, synthesis of phosphorothioate oligonucleotides is similar to that described above for naturally occurring oligonucleotides except that the oxidation step is replaced by a sulfurization step (Zon (1993) "Oliognucleoside Phosphorothioates" in Protocols for Oliognucleotides and Analogs, Synthesis and Properties (Agrawal, ed.) Humana Press, pp. 165-190). Similarly the synthesis of other phosphate analogs, such as phosphotriester (Miller et al. (1971) JACS 93:6657-6665), non-bridging phosphoramidates (Jager et al. (1988) Biochem. 27:7247-7246), N3' to P5' phosphoramidiates (Nelson et al. (1997) JOC 62:7278-7287) and phosphorodithioates (U.S. Pat. No. 5,453,496) has also been described. Other non-phosphorous based modified oligonucleotides can also be used (Stirchak et al. (1989) Nucleic Acids Res. 17:6129-6141). Oligonucleotides with phosphorothioate backbones can be more immunogenic than those with phosphodiester backbones and appear to be more resistant to degradation after injection into the host. Braun et al. (1988) J. Immunol. 141: 2084-2089; and Latimer et al. (1995) Mol. Immunol. 32:1057-1064.

ISS-containing polynucleotides used in the invention can comprise ribonucleotides (containing ribose as the only or principal sugar component), deoxyribonucleotides (containing deoxyribose as the principal sugar component), or, as is known in the art, modified sugars or sugar analogs can be incorporated in the ISS. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the ISS, the sugar moiety is in some examples the furanoside of ribose, deoxyribose, arabinose or 2'-0-alkylribose, and the sugar can be attached to the respective heterocyclic bases either in $\alpha$ or $\beta$ anomeric configuration. Sugar modifications include, but are not limited to, 2'-alkoxy-RNA analogs, 2'-amino-RNA analogs and 2'-alkoxy- or amino-RNA/DNA chimeras. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of an ISS.

The heterocyclic bases, or nucleic acid bases, which are incorporated in the ISS can be the naturally-occurring principal purine and pyrimidine bases, (namely uracil or thymine, cytosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the ISS can include one or several heterocyclic bases other than the principal five base components of naturally-occurring nucleic acids. In some examples, however, the heterocyclic base in the ISS includes, but is not limited to, uracil-5-yl, cytosin-5-yl, adenin-7-yl, adenin-8-yl, guanin-7-yl, guanin-8-yl, 4-aminopyrrolo [2.3-d]pyrimidin-5-yl, 2-amino-4-oxopyrolo [2,3-d]pyrimid 2-amino-4-oxopyrrolo [2.3-d]pyrimidin-3-yl groups, where the purines are attached to the sugar moiety of the ISS via the 9-position, the pyrimidines via the 1-position, the pyrrolopyrimidines via the 7-position and the pyrazolopyrimidines via the 1-position.

The ISS may comprise at least one modified base as described, for example, in the commonly owned U.S. Pat. No. 6,562,798 (U.S. Ser. No. 324,191) and international application WO 99/62923. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the ISS. In some examples, the electron-withdrawing moiety is a halogen. Such modified cytosines can include, but are not limited to, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, uracil, and any other pyrimidine analog or modified pyrimidine.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

In some examples, an ISS-containing polynucleotide is less than about any of the following lengths (in bases or base pairs): 10,000; 5,000; 2500; 2000; 1500; 1250; 1000; 750; 500; 300; 250; 200; 175; 150; 125; 100; 75; 50; 25; 10. In some examples, an ISS-containing polynucleotide is greater than about any of the following lengths (in bases or base pairs): 6; 7; 8; 10; 15; 20; 25; 30; 40; 50; 60; 75; 100; 125; 150; 175; 200; 250; 300; 350; 400; 500; 750; 1000; 2000; 5000; 7500; 10000; 20000; 50000. In some examples, an ISS-containing polynucleotide is greater than about 6 bases or base pairs in length and less than about 200 bases or base pairs in length.

Conjugate Molecule Populations with Varying Structural and Immunomodulatory Properties Generally, the classes, or populations, of conjugate molecules of the invention and described herein may be distinguished and/or defined by any of a number of structural and/or functional properties, including:

(a) average number of ISS-containing polynucleotides attached or linked to antigen;

(b) median number of ISS-containing polynucleotides attached or linked to antigen;

(c) ratio of average mass of ISS-containing polynucleotide to average mass of antigen;

(d) ratio of median mass of ISS-containing polynucleotide to median mass of antigen;

(e) ratio of (i) concentration of ISS-antigen conjugate required for inhibition of binding of antigen-specific antibody to antigen to (ii) concentration of antigen required for the same extent of inhibition of antigen-specific antibody to antigen (as discussed below, these ratios are usually, but need not be, calculated at 50% inhibition);

(f) for antigens which are allergens, the ratio of (i) concentration of ISS-antigen conjugate required for histamine release from basophils from an antigen-sensitized individual to (ii) concentration of antigen required for the same extent of histamine release from basophils from an antigen-sensitized individual (as discussed below, these ratios may be, but need not be, calculated at about 40% histamine release);

(g) ratio of (i) the sum of Th1-associated antibodies and Th2-associated antibodies elicited by ISS-antigen conjugate to (ii) the sum of Th1-associated antibodies and Th2-associated antibodies elicited by antigen;

(h) ratio of (i) Th1-associated antibodies elicited by ISS-antigen conjugate to (ii) ratio of Th2-associated antibodies elicited by ISS-antigen conjugate;

(i) different cytokine production profiles when compared to antigen alone;

(j) extent of suppression of antigen-specific antibody production.

All of these classes and examples described herein may be described and/or defined by one, more than one, and/or any combination of the properties listed above. Accordingly, the invention provides compositions comprising populations of structurally stable conjugate molecules, said conjugate molecules comprising an antigen and one or more polynucleotides comprising an immunostimulatory sequence (ISS), wherein said populations comprises any one or more of the properties described herein, either alone or in any combination. The properties (including ratios) may be measured using standard techniques in the art and described herein, and it is understood that any of these properties may be measured in a variety of systems, including in vivo systems such as vertebrates and mammals, including, for example, mouse and/or human.

In accordance with the above, for example, and based on observations pertaining to a conjugate of Amb a 1 and an ISS-containing 22-mer polynucleotide (5'-TGACTGTGAACGTTCGAGATGA-3', SEQ ID NO:1), the "H" class is defined by any of the following properties, either alone or in any combination:

(a) an average of at least about 5.5, and in some examples 6, ISS-containing polynucleotides per antigen molecule;

(b) ratio of (i) average mass of ISS-containing polynucleotide to (ii) average mass of antigen is (i) about or alternatively at least about 35, 40 or 45 to (ii) about 40;

(c) ratio of (i) concentration of ISS-antigen conjugate required for 50% inhibition of binding of antigen-specific antibody to antigen to (ii) concentration of antigen required for 50% inhibition of binding of antigen-specific antibody to antigen is about 3.5 to about 6.0 or more (including, but not limited to, 7.0, 8.0, 9.0, 10.0, 15, 20, 25, 30, 35, 40, 45, 50 or more) or alternatively is at least about any of the following: 3.5, 4.0, 4.5, 5.0, 5.5, 6.0, 6.5, 7.0, 8.0, 9.0, 10, 15, 20, 25 (if expressed as a range, the upper limit may be any number, including those listed);

(d) for examples in which the antigen is an allergen, the ratio of (i) concentration of ISS-antigen conjugate required for 40% histamine release from basophils from an antigen-sensitized individual to (ii) concentration of antigen required for 40% histamine release from basophils from an antigen-sensitized individual is greater than about 300, greater than about 500, greater than about 750, greater than about 1000, greater than about 1250, greater than about 1400, greater than about 1500 (with an upper limit being any number, including, but not limited to, 750, 1000, 1250, 1500, 1750, 2000, 2250, 2500, 2750, 3000, 3500, 4000, 4500, 5000, 5500, 6000);

(e) ratio of (i) titers of total Th1- and T2-associated antibodies elicited by ISS-antigen conjugate (in terms of antibodies elicited per unit mass of conjugate administered) to (ii) total Th1- and Th2-associated antibodies elicited by antigen (in terms of unit mass of antigen administered) is about or alternatively is less than about any of the following: 10, 7, 5, 4, 3.5, 3.0; 2.5, 2.0, 1.5, 1.0, 0.75, 0.5, 0.4, 0.3, 0.2, 0.1.

(f) ratio of (i) titers of total Th1- and Th2-associated antibodies elicited by ISS-antigen conjugate (in terms of antibodies elicited per unit mass of conjugate administered) to (ii) total Th1- and Th2-associated antibodies elicited by antigen (in terms of 10 times the unit mass of antigen administered compared to amount conjugate administered) is about or alternatively is less than about any of the following: 1.0, 0.7, 0.6, 0.5, 0.4, 0.35; 0.3; 0.25, 0.2, 0.15, 0.11, 0.075, 0.05, 0.04, 0.03, 0.02, 0.01.

(g) ratio of (i) titer of Th1-associated antibodies elicited by ISS-antigen conjugate (in terms of antibodies elicited per unit mass of conjugate administered) to (ii) titer of Th1-associated antibodies elicited by antigen (in terms of unit mass of antigen administered compared to amount conjugate administered) is about or alternatively is less than about any of the following: 60, 55, 50, 45, 40, 35, 30, 25, 20, 15, 10, 5;

(h) ratio of (i) titer of Th1-associated antibodies elicited by ISS-antigen conjugate (in terms of antibodies elicited per unit mass of conjugate administered) to (ii) titer of Th2-associated antibodies elicited by conjugate about or alternatively is greater than about any of the following: 4.0, 4.5, 5.0, 5.5, 6.0, 6.5, 7.0, 7.5, 8.0, 8.5, 9.0, 9.5, 10. If expressed as a range, the upper limit may be any number, including those listed, as well as others, such as 15, 20, 25, 30, 40, 50, 60, 75, 80, 90, 100;

(i) suppression of antigen-specific antibody production (including production of Th1-associated and/or Th2-associated antibodies) as compared to administration of the same amount of unlinked ISS-containing polynucleotide and antigen or compared to administration of the same amount of antigen alone.

The "M" class is defined by any of the following properties, either alone or in any combination:

(a) an average of from about 3 to about 5 ISS-containing polynucleotides per antigen molecule;

(b) ratio of (i) average mass of ISS-containing polynucleotide to (ii) average mass of antigen is (i) about 20, about 25, or about 30 to (ii) about 40;

(c) ratio of (i) concentration of ISS-antigen conjugate required for 50% inhibition of binding of antigen-specific antibody to antigen to (ii) concentration of antigen required for 50% inhibition of antigen-specific antibody to antigen is about 2.5 to about 3.0 or alternatively about 3.25;

(d) for examples in which the antigen is an allergen, the ratio of (i) concentration of ISS-antigen conjugate required for 40% histamine release from basophils from an antigen-sensitized individual to (ii) concentration of antigen required for 40% histamine release from basophils from an antigen-sensitized individual is about 100 to about 200, or, alternatively, about 100, or alternatively, about between about 75 to about 250.

(e) ratio of (i) titers of total Th1- and Th2-associated antibodies elicited by ISS-antigen conjugate (in terms of antibodies elicited per unit mass of conjugate administered) to (ii) total Th1- and Th2-associated antibodies elicited by antigen (in terms of unit mass of conjugate administered) is about 13 or alternatively is between about 10 or about 12 to about 100 (or, in some examples, about 12 to about 50);

(f) ratio of titers of total Th1- and Th2-associated antibodies elicited by ISS-antigen conjugate (in terms of antibodies elicited per unit mass of conjugate administered) to total Th1- and Th2-associated antibodies elicited by antigen (in terms of 10 times the unit mass of conjugate administered compared to amount conjugate administered) is about 1.3 or alternatively is between about 1.0 or about 1.20 to about 10 (or, in some examples, about 1.2 to about 5.0);

(g) ratio of (i) titer of Th1-associated antibodies elicited by ISS-antigen conjugate (in terms of antibodies elicited per unit mass of conjugate administered) to (ii) titer of Th1-associated antibodies elicited by antigen (in terms of unit mass of antigen administered compared to amount conjugate administered) is between about 70 to about 500;

(h) ratio of (i) titer of Th1-associated antibodies elicited by ISS-antigen conjugate (in terms of antibodies elicited per unit mass of conjugate administered) to (ii) titer of Th2-associated antibodies elicited by conjugate is about two to about 4.

The "L" class is defined by any of the following properties, either alone or in any combination:

(a) an average of less than about 3 ISS-containing polynucleotides per antigen molecule;

(b) ratio of (i) average mass of ISS-containing polynucleotide to (ii) average mass of antigen is (i) about 15 or alternatively less than about 15 (in some examples, about 10 or alternatively less than about 10) to (ii) about 40;

(c) ratio of (i) concentration of ISS-antigen conjugate required for 50% inhibition of binding of antigen-specific antibody to antigen to (ii) concentration of antigen required for 50% inhibition of antigen-specific antibody to antigen is less than about 2.0, or alternatively is about 2.0;

(d) for examples in which the antigen is an allergen, the ratio of (i) concentration of ISS-antigen conjugate required for 40% histamine release from basophils from an antigen-sensitized individual to (ii) concentration of antigen required for 40% histamine release from basophils from an antigen-sensitized individual is less than about 75, or, alternatively, about 75 (in other examples, less than about 60 or alternatively about 60) to about 200, or, alternatively, to about 100;

(e) ratio of (i) titers of total Th1- and Th2-associated antibodies elicited by ISS-antigen conjugate (in terms of antibodies elicited per unit mass of conjugate administered) to (ii) total Th1- and Th2-associated antibodies elicited by antigen (in terms of unit mass of conjugate administered) is about 150, or alternatively, greater than about any of the following: 100, 150, 200, 250, 300, 350, 400, 450, 500, 550, 600, 650, 700, 750, 800. If expressed as a range, the upper limit may be any number, including the numbers listed.

(f) ratio of (i) titers of total Th1- and Th2-associated antibodies elicited by ISS-antigen conjugate (in terms of antibodies elicited per unit mass of conjugate administered) to (ii) total Th1- and Th2-associated antibodies elicited by antigen (in terms of 10 times the unit mass of conjugate administered compared to amount conjugate administered) is about or alternatively is greater than about any of the following: 10, 12, 15, 20, 25, 30, 35, 40, 45, 50, 55, 60, 65, 70, 75, 80;

(g) ratio of (i) titer of Th1-associated antibodies elicited by ISS-antigen conjugate (in terms of antibodies elicited per unit mass of conjugate administered) to (ii) titer of Th1-associated antibodies elicited by antigen is about 500 or more, including, but not limited to, about 500 or more, about 600 or more, about 700 or more, about 800 or more, about 900 or more, about 1000 or more. If expressed as a range, the upper limit may be any number, including, but not limited to, 600, 700, 800, 900, 1000, 1250, 1500, 1750, 2000, 2500, 3000, 3500, 400, 4500, 5000;

(h) ratio of (i) titer of Th1-associated antibodies elicited by ISS-antigen conjugate (in terms of antibodies elicited per unit mass of conjugate administered) to (ii) titer of Th2-associated antibodies elicited by conjugate is about or alternatively is less than about any of the following: 2.0, 1.5, 1.25.

As is clear from the description herein, it is understood that any of a number of populations of conjugate molecules could be produced, and that the classifications of "L", "M", and "H" are several examples of classes of conjugate molecule populations. The ability to vary and control the extent of conjugation and thus control the type of modulation of the immune response extends to other populations in addition to those exemplified herein. Given the readily measurable structural and functional characteristics, it is well within the skill of the art to develop any of a number of populations. Accordingly, the invention also includes conjugate populations characterized by any of the following (either alone or in any combination):

(a) ratio of (i) concentration of ISS-antigen conjugate required for 50% inhibition of binding of antigen-specific antibody to antigen to (ii) concentration of antigen required for 50% inhibition of antigen-specific antibody to antigen is any of more than about 1.5, 2.0, 2.25, 3.0, 3.25, 3.5, 3.75, 4.0, 4.25, 4.50, 4.75, 5.0, 5.25, 5.5, 5.75, 6.0, 6.5, 7.0, 7.5, 8.0, 8.5, 9.0, 9.5, 10.0. If expressed as a range, the upper limit may be any number, including those listed (for example, the conjugate population may be more than about 2.0, more than about 2.0 and less than about 5.5, more than about 2.0 and less than about 20.0).

(b) ratio of (i) concentration of ISS-antigen conjugate required for 50% inhibition of binding of antigen-specific antibody to antigen to (ii) concentration of antigen required for 50% inhibition of antigen-specific antibody to antigen is any of less than about 1.5, 2.0, 2.25, 3.0, 3.25, 3.5, 3.75, 4.0, 4.25, 4.50, 4.75, 5.0, 5.25, 5.5, 5.75, 6.0, 6.5, 7.0, 7.5, 8.0, 8.5, 9.0, 9.5, 10.0. If expressed as a range, the lower limit may be any number listed as well as zero (for example, the conjugate population may be less than about 5.0, or alternatively less than about 5.0 and more than about 2.0).

(c) in instances where the antigen is an allergen, the ratio of (i) concentration of ISS-antigen conjugate required for 40% histamine release from basophils from an antigen-sensitized individual to (ii) concentration of antigen required for 40% histamine release from basophils from an antigen-sensitized individual is at least about any of the following: 2, 5, 10, 15, 20, 25, 30, 35, 40, 45, 50, 60, 75, 80, 90, 95, 100, 120, 130, 140, 150, 175, 200, 225, 250, 275, 300, 350, 400, 450, 500, 550, 600, 650, 700, 750, 800, 850, 900, 950, 1000, 1100, 1200, 1500, 1750, 2000, 2250, 2500, 2750, 3000, 3250, 3500, 3750, 4000, 4250, 4500, 4750, 5000. If expressed as a range, the upper limit may be any number, including those listed. Alternatively, this ratio may be less than about any of the following: 2, 5, 10, 15, 20, 25, 30, 35, 40, 45, 50, 60, 75, 80, 90, 95, 100, 120, 130, 140, 150, 175, 200, 225, 250, 275, 300, 350, 400, 450, 500, 550, 600, 650, 700, 750, 800, 850, 900, 950, 1000, 1100, 1200, 1500, 1750, 2000, 2250, 2500, 2750, 3000, 3250, 3500, 3750, 4000, 4250, 4500, 4750, 5000. If expressed as a range, the lower limit may be any number listed as well as zero.

(d) ratio of antibody titer (more particularly, IgG titer, such as the sum of Th1- and Th2-associated IgG titer) elicited per unit mass of ISS-antigen conjugate to antibody titer (more particularly, IgG titer, such as the sum of Th1- and Th2-associated IgG titer) elicited per unit mass of antigen as at least more than about any of the following: 0.1, 0.2, 0.3, 0.4, 0.5, 0.75, 1, 2, 5, 10, 15, 25, 50, 75, 100, 125, 150, 175, 200, 250, 300, 350, 400, 450, 500, 550, 600, 650, 700, 750, 800, 850, 900, 1000, 1250, 1500, 2000, 2250, 2500, 2750, 3000. If expressed as a range, the upper limit may be any number, including those listed. Alternatively, the ratio may be less than about any of the following: 0.1, 0.2, 0.3, 0.4, 0.5, 0.75, 1, 1.5, 2, 2.5, 3, 4, 5, 6, 7, 8, 9, 10, 15, 25, 50, 75, 100, 125, 150, 175, 200, 250, 300, 350, 400, 450, 500, 550, 600, 650, 700, 750, 800, 850, 900, 1000, 1250, 1500, 2000, 2250, 2500, 2750, 3000. If expressed as a range, the lower limit may be zero or any of the numbers listed.

(e) ratio of Th1-associated antibody titer elicited by conjugate to Th2-associated antibody titer elicited by conjugate (per unit mass) as less than about any of the following: 20, 15, 12, 10, 7, 5, 4.5, 4.25, 4.0, 3.75, 3.5, 3.25, 3.0, 2.5, 2.0, 1.5, 1.25, 1.0, 0.5. If expressed as a range, the lower limit may be any number listed, including zero. Alternatively, this ratio may be greater than any of the following: 0.5, 0.75, 1.0, 1.25, 1.5, 2.0, 2.5, 3.0, 3.25, 3.5, 4.0, 4.5, 5.0. If expressed as a range, the upper limit may be any number, including those listed.

(f) ratio of Th1-associated antibody titer elicited by conjugate to Th1-associated antibody titer elicited by antigen (per unit mass) is less than about any of the following: 5000, 4500, 4000, 3500, 3000, 2500, 2000, 1500, 1000, 900, 800, 700, 600, 500, 400, 300, 200, 150, 100, 50, 75, 60, 50, 40, 45, 30, 35, 25, 20, 14, 10, 5. If expressed as a range, the lower limit may be any number listed, including zero. Alternatively, this ratio may be more than about any of the following: 10, 20, 50, 60, 75, 100, 150, 200, 250, 300, 350, 400, 450, 500, 750, 800, 1000, 1250, 1500, 1750, 2000, 2250, 2500, 3000, 3500, 4000, 4500, 5000. If expressed as a range, the upper limit may be any number, including those listed.

The extent of conjugation can be controlled in a number of ways, all of which use chemical techniques well known in the art, which are also described herein. One way to control extent of conjugation is to vary the equivalents of ISS in relation to linkage sites on antigen. That is, a constant amount or number of linkage sites is reacted with a particular amount of ISS. For the ISS-Amb a I conjugate molecules exemplified herein, for example, based on maleimide-activated Amb a 1, reaction with 4 molar equivalents of 5' thio ISS, 7 molar equivalents of 5' thio ISS, and 17 molar equivalents of 5' thio ISS with 1 molar equivalent of Amb a 1 gave rise to "L", "M", and "H" populations, respectively. Another way of controlling extent of conjugation is to saturate the reaction with ISS and vary the amount of available linkage sites on antigen. The linkage sites could be controlled by, for example, choosing a certain linkage moiety that gave the desired number of linkage sites (for example, choosing to link via a carbohydrate as opposed to via amino groups), or alternatively, by controlling a linkage activating reaction such that the desired average number of linkage sites are activated.

Generally, a given antigen has a maximum number of potential linkage sites, depending on the nature of the antigen-ISS linkage. The extent of conjugation can be controlled by the number of these linkage sites which are used to link an ISS. Accordingly, the invention also includes examples in which the average percentage of total number of linkage sites attached to an ISS-containing polynucleotide is at least about any of the following: 5%, 10%, 20%, 30%, 33%, 40%, 45%, 50%, 55%, 60%, 65%, 70%, 75%, 80%, 82%, 85%, 88%, 90%, 92%, 95%, 97%, 98%. Alternatively, the invention also includes examples in which the average percentage of total number of linkage sites attached to an ISS-containing polynucleotides is less than about any of the following: 10%, 20%, 30%, 33%, 40%, 45%, 50%, 55%, 60%, 65%, 70%, 75%, 80%, 82%, 85%, 88%, 90%, 92%, 95%, 97%, 98%. The total number of linkage sites is determined by the mode of attachment. For example, if an antigen is linked to ISS-containing polynucleotide via a free amino group (such as in lysine), the total number of linkage sites is the number of lysines. If antigen is linked via a sulfhydryl group (such as via cysteine), then the total number of linkage sites is the total number of free sulfhydryl groups. If antigen is linked via a carbohydrate moiety, then the total number of linkage sites is the total number of carbohydrate moieties. With respect to any of these examples, the average percentage of linkage sites attached to ISS-containing polynucleotide may be accompanied by any of the immunomodulatory characteristics listed above, alone or in combination.

Characterization of Classes of ISS-Antigen Conjugate Molecule

Conjugate molecule populations may be identified and/or characterized by any of a number of ways, including those listed above. For example, in terms of structure, the extent of conjugation may be described by: (a) average or, alternatively median number of ISS to antigen molecules; (b) ratio of ISS to total linkage sites in antigen; (c) ratio of mass (whether average or median) of ISS to mass (whether average or median) of antigen; (d) ratio of ISS to T-cell epitopes in antigen; (e) ratio of ISS to B cell epitopes in antigen. In terms of function, which includes, but is not limited to, immune modulation, conjugate molecule populations of the invention may be characterized in terms of (a) degree of antigen-specific antibody response, such as IgG response; (b) ratio of Th1-associated antibodies to Th2-associated antibodies; (c) degree of suppression of histamine release; (d) degree of competition with antigen-specific antibody for binding to antigen; (e) degree of suppression of Th2-associated immune response; (f) secretion of Th1-associated cytokines, such as interferon; (g) secretion of Th2-associated cytokines, such as IL-4 and/or IL-5.

Structural Characterization

The extent of ISS-antigen conjugation may be determined using any number of protein and nucleic acid measurement methods known in the art. For example, antigen and/or protein-specific detection techniques (for example, antigen-specific antibodies and/or Coomassie Blue stain) and nucleic acid-specific detection techniques (for example, hybridization with detectably-labeled DNA probes) may be used to analyze conjugation reaction products. With the use of appropriate quantitation standards, the amount of polynucleotide to antigen may be determined.

The amount of oligonucleotide bound to a polypeptide may also be determined by the measurement of size or molecular weight of the conjugate molecule. Conjugate molecule size may be determined using methods known in the art including, but not limited to, sodium dodecylsulfate polyacrylamide electrophoresis (SDS-PAGE) analysis and size-exclusion chromatography (SEC).

The ISS-antigen conjugate molecules may be analyzed using a combination of size determination and/or separation techniques and nucleic acid and protein determination techniques. For example, after fractionation of conjugate molecule reaction products using SEC, the protein and nucleic acid content of each fraction may be determined by the absorbance of the fraction at 280 nm and 260 nm, respectively. In this way, the results of both the size of the conjugate molecule and the nucleic acid and protein detection analysis may be combined to characterize the structure of the conjugate molecule. The ratio of the amount of polynucleotide to the amount of protein in each conjugate molecule fraction indicates the average number of ISS molecules per antigen molecule.

Functional Characterization

Various methods known in the art may be used to determine antigen-specificity and antibody class and/or subclass of the antibodies generated in response to administration of ISS-antigen conjugate molecules. For example, standard ELISA format assays may be used to detect and measure the amount, specificity and/or type of antibody produced in response to various ISS-antigen conjugate molecules. In such assays, for example, antigen is attached to a substrate and incubated with serum from a ISS-antigen conjugate molecule treated individual. The amount of antigen-specific antibody attached to the substrate-bound antigen is then determined using antibody-specific reagents, such as antibodies specific for IgG1, IgG2, IgG3, IgG4, IgE, etc.

Methods known in the art may be used to determine a concentration of ISS-antigen conjugate molecule required for inhibition of binding of antigen-specific antibodies to antigen, such as competitive ELISA assays as described herein.

Methods known in the art may be used to measure the amount of histamine release from basophils from an antigen-sensitized individual in response to ISS-antigen conjugate molecule. For example, as described herein, the amount of histamine released into the cell culture supernatant may be determined after leukocytes from blood of allergic individuals are treated with varying concentrations and/or preparations of ISS-allergen conjugate molecules.

Methods known in the art may be used to determine the cytokine production profiles generated in response to administration of ISS-antigen conjugate molecules. For example, the supernatants of cells treated with ISS-conjugate molecules in vitro are analyzed for the presence of cytokines. The types and amounts of cytokines produced by lymphocytes exposed to ISS-antigen conjugate molecules may be measured using standard ELISA format assays. A cytokine profile produced in response to an ISS-antigen conjugate molecule may also be determined using standard cytokine bioassays including, but not limited to, those in which cell survival is dependent on the presence of a particular cytokine (for example, IL-2) and those in which a particular cytokine (for example, interferon) inhibits viral replication.

A class of conjugate molecule may also be characterized by the extent of antigen-specific antibody suppression after administration or relative to administration of antigen alone. For example, levels of serum antibodies may be determined before and after administration of the ISS-antigen conjugate molecule and/or antigen alone. The antibody levels at various time points may then be compared to determine the extent of antibody suppression.

A class of conjugate molecule may also be characterized by the extent of antibody response, and in some examples, an antigen-specific antibody response, especially an IgG response. As noted above, a class may be characterized by a ratio of (i) IgG antibodies produced in response to conjugate molecule to (ii) IgG antibodies produced in response to antigen alone. For these characterizations and examples, the ratio may be (i) the sum of Th1-associated antibodies and Th2-associated antibodies elicited by ISS-antigen conjugate molecule to (ii) the sum of Th1-associated antibodies and Th2-associated antibodies elicited antigen;

(ii) (i) a Th1-associated antibody (or antibodies) elicited by ISS-antigen conjugate molecule to (ii) Th1-associated antibodies elicited by antigen;

(iii)(i) a Th2-associated antibody (or antibodies) elicited by ISS-antigen conjugate molecule to (ii) Th2-associated antibodies elicited by antigen.

A Th1-associated antibody is an antibody associated with a Th1 response. In mice, for example, IgG2a is associated with a Th1 response. In humans, IgG1 and/or IgG3 antibodies appear to be associated with a Th1 response. See, e.g., Widhe et al. (1998) Scand. J. Immunol. 47:575-581 and de Martino et al. (1999) Ann. Allergy Asthma Immunol. 83:160-164. Similarly, a Th2-associated antibody is an antibody associated with a Th2 response. In mice, IgG1 is associated with a Th2 response. In humans, IgG2 and/or IgG4 appear to be associated with a Th2 response (Widhe et al. (1998) and de Martino et al. (1999)). In both humans and mice, IgE is associated with a Th2 response. It is understood that, for these characterizations and examples, any one or more type of antibody may be evaluated, as long as the same antibody or antibody production level is compared to that elicited by antigen alone.

One way to calculate this ratio is in terms of amount of antibody (or antibodies) of interest produced per unit mass of conjugate molecule versus amount of same antibody (or antibodies) produced per unit mass of antigen. The unit mass of the conjugate molecule may be in terms of mass of antigen component of conjugate molecule, polynucleotide component of conjugate molecule, and/or mass of conjugate molecule. For example, if a conjugate molecule has a total molecular weight of 100, with the antigen component accounting for 80 and the ISS component accounting for 20, the unit mass for purposes of calculating and comparing levels of antibody production may be any of 100, 80, or 20. The Examples provide calculations in which the mass of the antigen component of the conjugate molecule (Amb a 1) serves as the basis for calculating and comparing levels of antigen production compared to antigen alone.

Further, in calculating the ratio of antibody produced by conjugate molecule versus antibody produced by antigen, mass of conjugate molecule to mass of antigen may or may not be 1:1. For example, in some examples, antibody produced by unit mass of conjugate molecule is compared to antibody produced by any of 2, 3, 4, 5, 6, 7, 8, 10, 15, 20, 25, 30, 40 times the mass of antigen. For example, in the case of Amb a 1, antibody produced by 1 μg of conjugate molecule (as measured by the amount of antigen; thus 1 μg of antigen in the conjugate molecule) is compared to antibody produced by 10 μg of Amb a 1.

ISS-Antigen Conjugation

In some examples of compositions described herein, the ISS-containing polynucleotide is conjugated with the antigen. The ISS portion can be coupled with the antigen portion of a conjugate molecule in a variety of ways, including covalent and/or non-covalent interactions.

The link between the portions can be made at the 3' or 5' end of the ISS, or at a suitably modified base at an internal position in the ISS. If the antigen is a peptide and contains a suitable reactive group (e.g., an N-hydroxysuccinimide ester) it can be reacted directly with the $N^4$ amino group of cytosine residues. Depending on the number and location of cytosine residues in the ISS, specific coupling at one or more residues can be achieved.

Alternatively, modified oligonucleosides, such as are known in the art, can be incorporated at either terminus, or at internal positions in the ISS. These can contain blocked functional groups which, when deblocked, are reactive with a variety of functional groups which can be present on, or attached to, the antigen of interest.

Where the antigen is a peptide, this portion of the conjugate molecule can be attached to the 3'-end of the ISS through solid support chemistry. For example, the ISS portion can be added to a polypeptide portion that has been pre-synthesized on a support. Haralambidis et al. (1990a) Nucleic Acids Res. 18:493-499; and Haralambidis et al. (1990b) Nucleic Acids Res. 18:501-505. Alternatively, the ISS can be synthesized such that it is connected to a solid support through a cleavable linker extending from the 3'-end. Upon chemical cleavage of the ISS from the support, a terminal thiol group is left at the 3'-end of the oligonucleotide (Zuckermann et al. (1987) Nucleic Acids Res. 15:5305-5321; and Corey et al. (1987) Science 238:1401-1403) or a terminal amino group is left at the 3'-end of the oligonucleotide (Nelson et al. (1989) Nucleic Acids Res. 17:1781-1794). Conjugation of the amino-modified ISS to amino groups of the peptide can be performed as described in Benoit et al. (1987) Neuromethods 6:43-72. Conjugation of the thiol-modified ISS to carboxyl groups of the peptide can be performed as described in Sinha et al. (1991), pp. 185-210, Oligonucleotide Analogues: A Practical Approach, IRL Press. Coupling of an oligonucleotide carrying an appended maleimide to the thiol side chain of a cysteine residue of a peptide has also been described. Tung et al. (1991) Bioconjug. Chem. 2:464-465.

The peptide portion of the conjugate molecule can be attached to the 5'-end of the ISS through an amine, thiol, or carboxyl group that has been incorporated into the oligonucleotide during its synthesis. In some examples, while the oligonucleotide is fixed to the solid support, a linking group comprising a protected amine, thiol, or carboxyl at one end, and a phosphoramidite at the other, is covalently attached to the 5'-hydroxyl. Agrawal et al. (1986) Nucleic Acids Res. 14:6227-6245; Connolly (1985) Nucleic Acids Res. 13:4485-4502; Kremsky et al. (1987) Nucleic Acids Res. 15:2891-2909; Connolly (1987) Nucleic Acids Res. 15:3131-3139; Bischoff et al. (1987) Anal. Biochem. 164:336-344; Blanks et al. (1988) Nucleic Acids Res. 16:10283-10299; and U.S. Pat. Nos. 4,849,513, 5,015,733, 5,118,800, and 5,118,802. Subsequent to deprotection, the amine, thiol, and carboxyl functionalities can be used to covalently attach the oligonucleotide to a peptide. Benoit et al. (1987); and Sinha et al. (1991).

An ISS-antigen conjugate molecule can also be formed through non-covalent interactions, such as ionic bonds, hydrophobic interactions, hydrogen bonds and/or van der Waals attractions.

Non-covalently linked conjugate molecules can include a non-covalent interaction such as a biotin-streptavidin complex. A biotinyl group can be attached, for example, to a modified base of an ISS. Roget et al. (1989) Nucleic Acids Res. 17:7643-7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving an ISS and residues within the antigen, such as charged amino acids, or through the use of a linker portion comprising charged residues that can interact with both the oligonucleotide and the antigen. For example, non-covalent conjugation can occur between a generally negatively-charged ISS and positively-charged amino acid residues of a peptide, e.g., polylysine, polyarginine and polyhistidine residues.

Non-covalent conjugation between ISS and antigens can occur through DNA binding motifs of molecules that interact with DNA as their natural ligands. For example, such DNA binding motifs can be found in transcription factors and anti-DNA antibodies.

The linkage of the ISS to a lipid can be formed using standard methods. These methods include, but are not limited to, the synthesis of oligonucleotide-phospholipid conjugate molecules (Yanagawa et al. (1988) Nucleic Acids Symp. Ser 19:189-192), oligonucleotide-fatty acid conjugate molecules (Grabarek et al. (1990) Anal. Biochem. 185:131-135; and Staros et al. (1986) Anal. Biochem. 156:220-222), and oligonucleotide-sterol conjugate molecules. Boujrad et al. (1993) Proc. Natl. Acad. Sci. USA 90:5728-5731.

The linkage of the oligonucleotide to an oligosaccharide can be formed using standard known methods. These methods include, but are not limited to, the synthesis of oligonucleotide-oligosaccharide conjugate molecules, wherein the oligosaccharide is a moiety of an immunoglobulin. O'Shannessy et al. (1985) J. Applied Biochem. 7:347-355.

The linkage of a circular ISS to a peptide or antigen can be formed in several ways. Where the circular ISS is synthesized using recombinant or chemical methods, a modified nucleoside is suitable. Ruth (1991), pp. 255-282, in Oligonucleotides and Analogues: A Practical Approach, IRL Press. Standard linking technology can then be used to connect the circular ISS to the antigen or other peptide. Goodchild (1990) Bioconjug. Chem. 1:165. Where the circular ISS is isolated, or synthesized using recombinant or chemical methods, the linkage can be formed by chemically activating, or photoactivating, a reactive group (e.g. carbene, radical) that has been incorporated into the antigen or other peptide.

Additional methods for the attachment of peptides and other molecules to oligonucleotides can be found in U.S. Pat. No. 5,391,723; Kessler (1992) "Nonradioactive labeling methods for nucleic acids" in Kricka (ed.) Nonisotopic DNA Probe Techniques, Academic Press; and Geoghegan et al. (1992) Bioconjug. Chem. 3:138-146.

Kits Comprising a Conjugate Molecule

The present invention also provides kits comprising a composition comprising a structurally stable conjugate molecule and any one or more additional components as described herein, including but not limited to a component capable of maintaining the pH of the composition in the range of about 6.0 to about 9.0; an amino acid, a carbohydrate, a surfactant, and/or other pharmaceutically acceptable carrier. A kit may comprise an article of manufacture containing such compositions, wherein the composition may be in liquid or lyophilized form. In some examples, an article of manufacture comprises a composition comprising a conjugate molecule wherein the composition comprises greater than about 70%, greater than about 80%, greater than about 90%, greater than about 95% or greater than about 97% of the conjugate molecule in non-aggregate form at a temperature of between about 2 degrees C. and about 8 degrees C. In some examples, wherein the article of manufacture comprises a composition comprising an allergen, a kit may comprise at least 2, at least 3, at least 4, at least 5 or at least 6 articles of manufacture comprising said composition. In some examples, the allergen is Amb a 1. In some examples, aggregation is measured by RALS. In other examples, an article of manufacture comprises a liquid composition comprising a conjugate molecule and in other examples a lyophilized composition comprising a conjugate molecule. In yet other examples, an article of manufacture comprises a reconstituted liquid composition (that is, reconstituted from a lyophilized composition) comprising a conjugate partner. The kits of the invention may optionally contain instructions for their use (for example, instructions for any of the methods described herein) and/or any other suitable components.

Methods of Using and Making Compositions Comprising Conjugate Molecules

The invention also includes methods of making and using a composition comprising a structurally stable conjugate molecule. Compositions comprising a structurally stable conjugate molecule as described herein are especially useful for administering to an individual in need of immune modulation (in the context of, for example, infectious disease, cancer, and/or allergy). Accordingly, the present invention provides pharmaceutical compositions comprising a structurally stable conjugate molecule. Methods generally comprise administration of a composition comprising a structurally stable conjugate molecule or conjugate molecule population as described herein to an individual in an amount sufficient to modulate an immune response in the individual. In some examples, methods of modulating an immune response comprise administering a composition comprising a conjugate molecule such that the desired modulation of the immune response is achieved. Assessment of immune responses have been described above. In some examples, a kit comprises an article of manufacture comprising a composition comprising structurally stable AIC in a range of about 0.1 μg to about 200 μg. In other examples, a composition comprises AIC in a range of at least about 10 μg, 20 μg, 30 μg, 40 μg, 50 μg, 60 μg, 70 μg, 80 μg, 90 μg or 100 μg and up to about 110 μg, 120 μg, 130 μg, 140 μg, 150 μg, 160 μg, 170 μg, 180 μg, 190 μg or 200 μg. In some examples, a composition comprises AIC in a range of between about 30 μg and about 60 μg.

Provided herein are methods for modulating an immune response in an individual comprising the step of administered to the individual a composition comprising a structurally stable conjugate molecule. In some examples, the conjugate molecule comprises an allergen, and in other examples, the conjugate molecule comprises Amb a 1. In yet other examples, the conjugate molecule is AIC. In some examples, the composition comprises AIC and a component capable of maintaining the pH of the composition in the range of about 6.0 to about 9.0 and additionally may contain any one or more of the following; 1) an amino acid; 2) a carbohydrate; 3) a surfactant, or 4) other pharmaceutically acceptable carrier as long as the AIC is structurally stable within the composition.

In some examples, the invention provides methods of modulating an immune response in an individual which comprise administering a composition comprising any of the conjugate molecules or conjugate molecule populations described herein to the individual in an amount sufficient to modulate the immune response. Generally, the individual is in need of, or will be in need of, such modulation, due, for example, for a disease condition or being at risk of developing a disease condition. Examples of disease conditions include, but are not limited to, allergy, cancer, infectious diseases (such as viral or bacterial infection). In some examples, the disease condition is an allergy.

In some examples, the immune modulation comprises stimulating a (i.e., one or more) Th1-associated cytokine, such as interferon-γ. In some examples, the immune modulation comprises suppressing production of a (i.e., one or more) Th2-associated cytokine, such as IL-4 and/or IL-5. Measuring these parameters uses methods standard in the art and has been discussed above.

In some examples, one (or more) Th1-associated cytokines is produced, while antigen-specific antibody production is suppressed. Measuring these parameters uses methods standard in the art and has been discussed above.

In one example, the immune modulation comprises stimulating a (i.e., one or more) Th1-associated cytokine, such as interferon-γ, and suppressing production of antigen-specific antibodies. Degrees of suppression of antigen-specific antibody production for various conjugate molecule populations, including Th1-associated antibody production and combination of Th1- and Th2-associated antibody production, have been described above and apply to these methods.

In some examples, the immune modulation comprises suppression of histamine release. Degrees of suppression of histamine release for various conjugate molecule populations have been described above and apply to these methods.

In some examples, methods of suppressing antibody formation, preferably antigen-specific antibody formation, in an individual, while stimulating production of a Th1-associated cytokine comprise administering a composition comprising a population ISS-antigen conjugate molecules of the H class to the individual whereby antibody formation is suppressed while a Th1-associated cytokine is stimulated. Measuring these parameters uses methods standard in the art and has been discussed above.

In some examples, the invention provides methods of treating an allergic condition in an individual which comprise administering any of the compositions comprising a structurally stable conjugate molecule or conjugate molecule population as described herein in which the antigen is an allergen in an amount sufficient to ameliorate or palliate the allergic condition, generally by modulating the immune response to the antigen. Palliation can be determined by, for example, alleviation of one or more symptoms associated with allergy.

The invention also provides methods of reducing allergenicity of an antigen, particularly an allergen, comprising administering a composition comprising a structurally stable conjugate molecule as described herein to an individual in need, such that allergenicity is reduced. In some examples, the conjugate molecule is AIC.

Generally, the route(s) of administration of compositions comprising structurally stable conjugate molecules useful in a particular application are apparent to one of skill in the art. Routes of administration include, but are not limited to, intravascular, arterial or venous; subcutaneous; intraperitoneal; intraorganal; intramuscular; oral; transmucosal; epidermal; parenteral; and gastrointestinal or the like. For in vitro or ex vivo administration, the compounds may be provided in the medium of the cells and/or organ, as a single bolus, by repetitive addition, by continual infusion, or the like.

For administration, the compositions may conveniently be presented in unit dosage form and may be prepared by any methods well known in the art of pharmacy. Such methods include the step of bringing into association a conjugate molecule or conjugate molecule population with components as described herein. To determine the optimum concentration of conjugate molecule for any application, conventional techniques may be employed. Compositions may include aqueous and non-aqueous isotonic sterile injection solutions which may contain bacteriostats and solutes which render the composition isotonic with the blood of the intended recipient as long as the conjugate molecule remains structurally stable within the composition. If a composition comprising a structurally stable conjugate molecules is provided as an aerosol, propellant(s) known in the art may be added to a liquid composition.

The above-mentioned compositions and methods of administration are meant to describe but not limit the methods and compositions of the present invention. The methods of producing various compositions and devices are within the ability of one skilled in the art and are not described in detail here.

The invention also provides methods of making compositions comprising structurally stable conjugate molecules comprising any of the techniques and/or steps described herein. Accordingly, provided herein are methods for preparing a composition comprising a structurally stable conjugate molecule comprising combining a conjugate molecule with a component capable of maintaining the pH in the range of about 6.0 to about 9.0. Such components are described herein In some examples, the method of preparing a composition comprising a structurally stable conjugate molecule further comprises the step of combining the conjugate molecule with any one or more of 1) an amino acid as described herein; 2) a carbohydrate as described herein; 3) a surfactant; and 4) a pharmaceutically acceptable carrier in any order, as long as the conjugate molecule remains structurally stable. The present invention also provides methods of preparing a lyophilized composition comprising the step of lyophilizing a liquid composition comprising a structurally stable conjugate molecule. The present invention also provides methods of preparing a reconstituted composition comprising reconstituting a lyophilized composition.

The following Examples are provided to illustrate but not limit the present invention. Various modifications of the invention in addition to those described herein will become apparent to those skilled in the art from the foregoing description and accompanying figures. Such modifications are intended to fall within the scope of the appended claims.

EXAMPLES

Example 1

Preparation of AIC-L, AIC-M, or AIC-H

The Amb a 1-ISS Oligonucleotide Conjugate (AIC) is a protein-oligonucleotide conjugate prepared by covalently linking the purified short ragweed antigen Amb a 1 to a phosphorothioate immunostimulatory (ISS) oligonucleotide. The Amb a 1 is isolated from the pollen at 2-8° C. by extraction and ammonium sulfate precipitation. The crude extract is processed at ambient temperature through two chromatography steps. Amb a 1 is purified by DEAE Sepharose Fast Flow anion exchange chromatography followed by Butyl Sepharose Fast Flow hydrophobic interaction chromatography.

Crosslinking is via the heterobifunctional linker sulfosuccinimidyl-4-(N-maleimidomethyl)cyclohexane-1-carboxylate (sSMCC). The sSMCC creates stable amide and thioether bonds between the ISS oligonucleotide and the Amb a 1. AIC has an average of approximately 4.0 moles of ISS oligonucleotide per mole of Amb a 1 and has an average molecular weight of approximately 65 kDa. The Amb a 1 antigen (molecular weight of approximately 37,800 Da) is purified from defatted short ragweed pollen (Ambrosia artemisiifolia) using standard chemical and chromatographic techniques. After purification, free Amb a 1 sulfhydryls are blocked with N-ethylmaleimide (NEM). The blocked protein is then activated with s-SMCC. At pH 7.2 the Amb a 1 amino groups react exclusively with the succinimidyl ester of sSMCC to form stable amide bonds, creating maleimide activated Amb a 1. Concurrent to the Amb a 1 activation reaction, the 5'Disulfide ISS oligonucleotide is reduced with tris-(2-carboxyethyl)phosphine hydrochloride (TCEP) to yield 5' Thio ISS oligonucleotide. The activated Amb a 1 maleimide group reacts with the sulfhydryl of the 5' Thio ISS oligonucleotide to form a stable thioether bond, covalently linking the Amb a 1 to the ISS and creating AIC. AIC is purified by Superdex HR 200 Gel Filtration chromatograph. The 5'Disulfide ISS oligonucleotide, which contains the immunostimulatory hexamer motif 5'-AACGTT, has the sequence 5'-Disulfide-TGACTGTGAACGTTCGAGATGA-3' (SEQ ID NO:1). The theoretical molecular weight is approximately 7500 Da.

AIC-L, AIC-M, and AIC-H are covalent conjugate molecules of the ragweed allergen Amb a 1 and the ISS-containing polynucleotide 5'-TGACTGTGAACGTTCGAGATGA-3' (SEQ ID NO: 1). All three classes of conjugate molecule are prepared from the same ISS-containing polynucleotide and employing the same heterobifunctional linker. The number of oligonucleotides conjugated to the Amb a 1 can distinguish the classes. The amount of oligonucleotide bound to Amb a 1 can be determined by the measurement of size or the molecular weight of the conjugate molecules. AIC-L contains an average of 2-3 oligonucleotides per Amb a 1 molecule, AIC-M an average of 3.5 to 4.5, and AIC-H contains an average of >5.5. These three classes of AIC have different biological properties as described.

Preparation and Isolation of 5'thio ISS Oligonucleotide

The 5'disulfide ISS oligonucleotide was synthesized as a phosphorothioate on a controlled pore glass support (CPG) using an automated synthesizer. The required sequence was assembled using the standard β-cyanoethylphosphoramidite 'DMT off' approach of detritylation, coupling, oxidation, and capping. The HSP process produces lyophilized 5'-Disulfide ISS oligonucleotide as a bulk pharmaceutical that is released by HSP.

Triscarboxyethylphosphine (TCEP) was allowed to reach ambient temperature and dissolved in 10 mM $NaPO_4$/141 mM NaCl/pH 7.2. The 5' disulfide ISS oligonucleotide was allowed to reach ambient temperature, dissolved in the same buffer, and treated with the TCEP solution for 2 hours at 40° C. This material was carried on directly to the isolation step.

Two pre-packed desalting columns were connected in series and equilibrated with 10 mM $NaPO_4$/141 mM NaCl/pH 7.2 buffer. The 5'disulfide ISS oligonucleotide reduction mixture was loaded onto the column and the 5'thio ISS oligonucleotide was eluted isocratically.

Preparation and Isolation of Maleimide-Activated Amb a 1

N-ethyl maleimide (NEM) was allowed to reach ambient temperature and dissolved with stirring in dimethyl sulfoxide (DMSO). Amb a 1 was thawed and treated with the NEM solution for 2 hours at 20° C. Sulfosuccinimidyl-4-(N-maleimidomethyl) cyclohexane-1-carboxylate (sSMCC) was allowed to reach ambient temperature and dissolved in DMSO. The NEM blocked Amb a 1 was treated with the sSMCC solution for 2.5 hours at 20° C. This material was carried on directly to the isolation step. Two pre-packed desalting columns were connected in series and equilibrated with 10 mM $NaPO_4$/141 mM NaCl/pH 7.2 buffer. The Amb a 1 activation mixture was loaded onto the column and the maleimide activated Amb a 1 was eluted isocratically.

Preparation and Isolation of AIC-L, AIC-M, or AIC-H

The crude AIC-L conjugate molecule was prepared by incubation of a mixture of 4 molar equivalents of 5' thio ISS oligonucleotide and 1 molar equivalent the maleimide activated Amb a 1 for 3 hours at 20° C. Crude AIC-M and AIC-H were prepared in a similar manner but by addition of 7 and 17 molar equivalents of 5' thio ISS oligonucleotide, respectively. A pre-packed gel filtration column was equilibrated with 10 mM $NaPO_4$/141 mM NaCl/pH 7.2 buffer and the crude AIC-L, AIC-M, or AIC-H were loaded onto the column. The AIC was eluted isocratically with 10 mM $NaPO_4$/141 mM NaCl/pH 7.2 buffer.

Example 2

Stability Profiling of Compositions Comprising AIC

Experiments were designed to determine possible structural changes in the conjugate molecule AIC (ratio of 3 to 5 ISS per Amb a 1) within compositions as a function of pH, temperature, time and composition conditions, such as, for example, ionic strength and the presence of surfactants. Studies were undertaken at temperatures between about 2 to about 8° C. (real time stability) and at elevated temperatures (accelerated stability). Experiments were designed to compare structural stability of AIC in a composition containing 10 mM sodium phosphate, 141 mM sodium chloride pH 7.2 (PBS) stored frozen at ←60° C. to the structural stability of AIC in a composition containing 20 mM histidine, 50 mM glycine, 210 mM sucrose, pH 7.5 (HGS) stored liquid at 2-8° C. The PBS and HGS containing compositions were analyzed using full release testing and additional characterisation using in vitro histamine release testing. At least six months of real-time stability was demonstrated for AIC stored at 2-8° C. in the HGS formulation. For AIC in PBS, the AIC was prepared by dilution of AIC into a 10 mM sodium phosphate, 141 mM sodium chloride pH 7.2 (PBS) composition followed by a sterile filtration and was stored frozen at ←60° C. Real-time stability studies on the AIC in PBS demonstrated at least 24 months stability when stored at ←60° C. The ←60° C. storage temperature was chosen because accelerated stability studies revealed that AIC drug product underwent aggregation with time when stored liquid at 2-8° C. in PBS. This aggragation resulted in an approximately 30% decrease in AIC monomer content in 12 months as evaluted by a Size Exclusion Chromatography (SEC) method. Up to 33% aggregate resulted in no decrease in potency as determined by the generation of murine IgG2a antibodies (described herein). Results using the SEC method for characterizing AIC in PBS stored at both ←60° C. and 2-8° C. are shown in Tables 2 and 3 below.

TABLE 2

Stability of AIC 30 μg/ml in 10 mM sodium phosphate, 141 mM sodium chloride pH 7.2 at <−60° C. and 2-8° C.

| | Percent AIC monomer by SEC | |
|---|---|---|
| Storage Months | 2-8° C. | <−60° C. |
| 0 | 95 | 95 |
| 1 | 91 | 97 |
| 2 | 88 | 93 |
| 3 | 84 | 93 |
| 6 | 82 | 96 |
| 9 | 79 | 96 |
| 12 | 67 | 93 |
| 18 | 70 | 94 |
| 24 | 71 | 97 |

TABLE 3

Stability of AIC 60 μg/ml in 10 mM sodium phosphate, 141 mM sodium chloride pH 7.2 at <−60° C. and 2-8° C.

| | Percent AIC main peak purity by SEC | |
|---|---|---|
| Storage Months | 2-8° C. | <−60° C. |
| 0 | 94 | 94 |
| 1 | 88 | 95 |
| 2 | 87 | 96 |
| 3 | 85 | 97 |
| 6 | 44 | 95 |
| 9 | 68 | 94 |
| 12 | 64 | 94 |
| 18 | 67 | 95 |
| 24 | 65 | 95 |

Stability profiling on liquid compositions comprising AIC revealed that negatively charged components destabilized AIC resulting in a presumed conformational change and aggregation. The sodium phosphate and sodium chloride of the PBS formulation both contributed to the aggregation of AIC. Additional stability profiling resulted in the development of an AIC composition containing 20 mM histidine, 50 mM glycine, 210 mM sucrose, pH 7.5 (HGS) that was structurally stable as a liquid at 2-8° C. Accelerated studies on AIC in HGS showed minimal loss of AIC monomer at 20-22° C. when compared to the AIC in PBS composition. Results using the SEC method for AIC stored at both 20-22° C. and 2-8° C. are shown in Table 4 and 5 shown below.

TABLE 4

Stability of AIC 30 μg/ml of AIC in 20 mM histidine, 50 mM glycine, 210 mM sucrose, pH 7.5 at 20-22° C. and 2-8° C.

| | Percent AIC main peak purity by SEC | |
|---|---|---|
| Storage Months | 2-8° C. | 20-22° C. |
| 0 | 97 | 97 |
| 1 | 95 | 92 |
| 3 | 97 | 90 |
| 6 | 93 | 93 |

TABLE 5

Stability of AIC 30 μg/ml in 10 mM sodium phosphate, 141 mM sodium chloride pH 7.2 at 20-22° C. and 2-8° C.

| | Percent AIC main peak purity by SEC | |
|---|---|---|
| Storage Months | 2-8° C. | 20-22° C. |
| 0 | 98 | 98 |
| 1 | 95 | 52 |
| 3 | 89 | 25 |
| 6 | 77 | 11 |

Real-time stability studies of the AIC in HGS stored at 2-8° C. have demonstrated at least 2 months stability with no significant aggregate formation. Results using the SEC method for AIC stored at 2-8° C. and accelerated at 23-27° C. are shown in Tables 6 and 7 below.

TABLE 6

Stability of AIC 30 μg/ml of AIC in 20 mM histidine, 50 mM glycine, 210 mM sucrose, pH 7.5 at 23-27° C. and 2-8° C.

| | Percent AIC main peak purity by SEC | |
|---|---|---|
| Storage Months | 2-8° C. | 23-27° C. |
| 0 | 95 | 95 |
| 1 | 93 | 91 |
| 2 | 93 | 87 |

TABLE 7

Stability of AIC 60 μg/ml of AIC in 20 mM histidine, 50 mM glycine, 210 mM sucrose, pH 7.5 at 23-27° C. and 2-8° C.

| | Percent AIC main peak purity by SEC | |
|---|---|---|
| Storage Months | 2-8° C. | 23-27° C. |
| 0 | 95 | 95 |
| 1 | 93 | 91 |
| 2 | 93 | 88 |

Example 3

Activity of AIC in PBS or HGS: Murine IgG2a Activity

Murine IgG2a Activity

The biological activity of AIC was determined by the ability to generate an Amb a 1 specific IgG2a response in BALB/c mice. Twelve-week-old female BALB/c mice from Jackson Labs were immunized intradermally in the tail twice at two-week intervals with 1 μg doses of AIC (10 mice/group). Amb a 1 specific IgG2a titers were determined by ELISA from serum collected two weeks post 2nd immunization. Nunc Maxisorp 96-well plates were coated with 1 μg/ml Amb a 1 in phosphate buffer overnight at 4° C., washed, and blocked. Serum dilutions were loaded on plates and incubated at 4° C. overnight. Amb a 1 IgG2a antibodies were detected with a biotinylated goat anti-mouse IgG2a conjugate molecule. After treatment with a streptavidin—HRP conjugate molecule plates were developed with 3,3',5,5' tetramethylbenzidine. $A_{450}$ was determined on an ELISA plate reader. Titers were calculated as the reciprocal of the serum dilution that gives an $A_{450}$ of 0.5. The IgG2a Activity (titer) for AIC 30 μg/ml in 10 mm sodium phosphate, 141 mM NaCl, pH 7.2=112,356 and the IgG2a Activity (titer) for AIC 30 μg/ml in 20 mm Histidine, 50 mm Glycine, 210 mm Sucrose (HGS), pH7.5=69,705. The IgG2a Activity (titer) for AIC 60 μg/ml in 10 mm sodium phosphate, 141 mM NaCl, pH 7.2=64,422 and the IgG2a Activity (titer) for AIC 60 μg/ml in HGS=58,057.

Example 4

Allergenicity of AIC in PBS or HGS: Histamine Release

In addition to the testing performed on the AIC described in Example 3 in vitro characterization of AIC in HGS and PBS was performed. Specifically, the allergenicity of these compositions were tested using in vitro histamine release assay. The allergenicity of AIC in PBS and HGS was compared to Amb a 1 using an in vitro histamine release assay. In this assay, leukocytes were prepared from blood of ragweed allergic patients. These cells were incubated for 45 minutes with concentrations of Amb a 1 or AIC ranging from 0.0001 to 1.0 μg/ml. The cells were then pelleted by centrifugation and the supernatants were analyzed for histamine content by automated fluorometry. 100% histamine release is determined by lysing cells with 2% $HClO_4$. The results are shown in Table 8. The results are expressed in terms of $HR_{40}$, which is defined as the concentration of sample (Amb a 1 or AIC in μg/ml) required to induce a 40% histamine release from the human cells. The results show that AIC in both compositions have comparably reduced ability to induce histamine release with $HR_{40}$ values for the two compositions ranging from 59 to 46-fold higher than Amb a 1 (59 to 46-fold more AIC is required to induce histamine release). Both compositions are considerably less allergenic than unconjugated Amb a 1.

TABLE 8

Histamine release ($HR_{40}$)[a] from human leukocytes induced by Amb a 1 and AIC

| | Concentration of Test Material (μg/ml) | | |
|---|---|---|---|
| Patient | Amb a 1 Control | AIC (HGS) | AIC (PBS) |
| 1 | 0.00025 | 0.0035 | 0.006 |
| 2 | 0.000175 | 0.0035 | 0.0035 |
| 3 | 0.00027 | 0.02 | 0.027 |

TABLE 8-continued

| Histamine release ($HR_{40}$)[a] from human leukocytes induced by Amb a 1 and AIC | | | |
|---|---|---|---|
| | Concentration of Test Material (μg/ml) | | |
| Patient | Amb a 1 Control | AIC (HGS) | AIC (PBS) |
| 4 | 0.00035 | 0.0045 | 0.009 |
| 5 | 0.00055 | 0.1 | 0.05 |
| 6 | 0.001 | 0.03 | 0.03 |
| Mean | 0.00046 | 0.027 | 0.021 |
| Std dev | ±0.00030 | ±0.037 | ±0.018 |
| Ratio AIC:Amb a 1 | — | 59 | 46 |

[a]$HR_{40}$ - Concentration of Amb a 1 or AIC required to induce 40% histamine release

Example 5

Stability Studies of AIC in PBS and HGS

The inventors discovered that the structural stability of a conjugate molecule is dependent upon temperature, salt and pH conditions. The present inventors have found that a conjugate molecule comprising an antigen undergoes aggregation with time when stored liquid at 2-8 degrees C. in compositions comprising sodium phosphate and sodium chloride. Without being bound by theory, it is believed that due to the negative charge of the conjugate molecule, by virtue of the presence of an ISS, compositions comprising non-negatively charged components or components having a neutral charge or non-polar components are desired to maintain the structural stability of the conjugate molecule present in the composition. The structural stability of a conjugate molecule comprising the allergen Amb a 1 within various composition was characterized using, IF, EF, RALS, HPLC-SEC, SDS PAGE as described herein.

Materials and Methods

IF, EF and RALS Methods

Intrinsic Fluorescence (IF) measures possible changes in the Tryptophan environment arising from stress-induced conformational changes. While the effects of stress-related structural changes can be very subtle and are detected by examining possible changes in Tryptophan (Trp) and/or Tyrosine (Tyr) and Phenylalanine (Phe) intrinsic fluorescence (IF), in most conjugate molecules, the polarity-sensitive Trp fluorescence dominates all intrinsic fluorophores. This polarity-dependent fluorescence sensitivity can be used to monitor changes in conformation as a molecule is subjected to stressful environmental changes. The environmentally sensitive residue is susceptible to solvent accessibility, pH, and the proximity of neighboring side-chains, etc. Thus, pure Tryptophan has an emission max of 355 nm in a polar environment and 305 nm in a non-polar environment. Therefore, a ratio of intensities (high/low) can yield information about the unfolding/structural response to external stimuli. Further, by using a ratio, inaccuracies caused by differences in AIC concentration and changes in instrumentation are eliminated. In IF, the higher the ratio, the more unfolded the molecule (the Trp residues are exposed to a more polar environment).

Extrinsic Fluorescence (EF) utilizes an external, non-covalent, polarity-sensitive fluorescent probe, such as for example, ANS (8-anilino-naphthalene sulphonic acid), to probe a conjugate molecule's apparent exposure of hydrophobic domains and to monitor possible changes in this parameter as a function of various environmental stresses and conditions. Fluorescent probes that have an affinity for hydrophobic domains on conjugate molecules can complement intrinsic fluorescence. Changes in AIC or other conjugate molecules induced by various solution stresses can result in changes in the hydrophobic domains to which such probes bind, which in turn can affect the spectral characteristics of the non-covalently bound probe fluorescence. Thus, the binding of ANS to hydrophobic clefts in AIC, or other conjugate molecules, could be affected by changes in pH, ionic strength, polarity, aggregation, etc. ANS fluorescence in the absence of AIC is independent of pH and temperature. ANS has an emission max of 520 nm in a polar environment and 490 nm in a non-polar environment. Therefore, a ratio of fluorescent emissions at 520 nm and 490 nm (520/490) is indicative of the apparent exposure of hydrophobic domains on AIC or other conjugate molecules examined, with a lower ratio indicating increasing hydrophobic cleft availability to the probe, and therefore more unfolding of the molecule.

Right Angle Light Scatter (RALS) can be employed to detect and monitor the subtle changes in associative behavior of stressed conjugate molecules in otherwise visually clear formulations. Conformational changes in conjugate molecules can result in an association between molecules to possibly exclude polar water. This associative behavior can be subtle or can be easily detected as soluble and insoluble aggregates or even visible precipitation. RALS monitors macroscopic changes in an otherwise soluble molecule transitioning to insoluble aggregates. On a scale of 0-10 (instrument scale of minimum/maximum intensity), 10 could suggest self-association in otherwise visually clear formulations.

Temperature Stress

AIC samples were heated at 2° C./minute, from 20-90° C. using a circulating, programmable water bath. At 1-minute intervals, sample temperatures and either EF or RALS and IF data were recorded to determine possible conformational changes at different stress temperatures.

Shear Stress

AIC samples were agitated rapidly (300 rpm, which avoids cavitation) in a conical glass vial using a triangular stir bar. At pre-determined time intervals, solution clarity was noted and an aliquot removed to assess aggregation by RALS, and recoveries and aggregate content by SEC.

pH Profiles

The structural stability of most conjugates is influenced by pH. AIC was probed for possible pH-induced conformational changes during pH-transitions using RALS, IF, and EF. This was performed by dialyzing AIC into the Base Buffer (as described below) that allows for easy pH transitions and then titrating with HCl and NaOH while observing RALS. In addition, product stability was examined using a range of pH conditions, using IF and RALS or EF.

Experimental Procedures

For all experiments, both RALS and IF data were recorded at the same time in a fluorimeter. Due to the inclusion of an external probe, the EF measurements were recorded in separate experiments.

Determination of Monochrometer Settings

A 30 pg/mL AIC solution was prepared in 10 mM Sodium Phosphate, 141.7 mM NaCl at pH 7.2 (PBS). An absorbance scan was run on this sample using a UV spectrophotometer. The wavelength of maximum absorbance was found to be 258 nm. The sample was then examined using excitation and emission scans. Although AIC exhibited a maximal absorbance at 258 run (that is, 258 nm), the IF excitation was chosen at 295 nm because the excitation of Trp overlaps that of Phe and Tyr. The IF excitation wavelength was therefore chosen 10 nm above the maximum. A ratio of emissions wavelength is used to assess changes in conformation. The emission wavelengths of 295 nm were chosen based on an emissions scan, with the wavelengths that yield a half-maximal emission value being selected. For AIC, these wavelengths were 323 nm and 363 nm.

RALS and EF do not require wavelength determinations. However, RALS does require a voltage determination, and the voltage used varies according to AIC concentration. RALS is best monitored by setting excitation and emission wavelengths at 320 nm. The extrinsic probe ANS is excited at 380 nm and the emissions observed at 490 nm and 520 nm. ANS has an emission max of 520 nm in a polar environment and 490 nm in a non-polar environment. Therefore, a ratio of fluorescent emissions at 520 nm and 490 nm (520/490) is indicative of the apparent exposure of hydrophobic domains on AIC examined, with a lower ratio indicating increasing hydrophobic cleft availability to the probe.

For extrinsic fluorescence measurements, ANS (8-anilinonaphthalene sulphonic acid) is added to the sample as an external probe. To determine the amount of ANS needed to follow changes in AIC conformation, ANS was titrated into a 400 pL-sample of drug (30 μg/mL) in its current formulation. By monitoring the fluorescence intensities during this titration, a final concentration for ANS of 0.175 mM, obtained by adding 7 AL of a 10 mM stock to 400 gL of 30 pg/mL sample, was determined as most appropriate for tests.

Guanidine titration was used to determine the maximum possible IF intensity changes resulting from changes in the Trp environment due to conformational changes. Samples were prepared containing Guanidine ranging from 0 M to 6 M (incubated at room temperature for 30 minutes), and fluorescence emission scans were performed. The scans were obtained using 295 nm Excitation. Three ratios using emission wavelengths at the maximum emission wavelength (343) and at +20 nm and −20 nm from the peak.

These scans suggest that AIC was denatured in concentrations greater than 5 M Guanidine and the Trp residues present are now emitting fluorescent light at a higher wavelength due to the conformational change. Since the ratio of 323/363 gave the greatest range of ratios over the Guanidine titration, this ratio was chosen for all studies.

To investigate the Shear sensitivity of AIC, a preliminary study was performed using 425 μL of 30 μg/mL AIC. These samples in PBS buffer were agitated rapidly (without cavitation) in conical glass vials (one vial per time point) using a triangular stir bar rotated at 350 rpm. At pre-determined time intervals (0, 0.5, 1, 2, 3, 4, 8, and 24 hrs), one vial from each condition was removed from the magnetic stirrer. All samples were kept at room temperature until the study was completed. Solution clarity was then noted and aggregation was assessed by RALS, and recovery and degradation was assessed by HPLC.

AIC appeared to be moderately shear stress sensitive. The RALS increased substantially at 3 hours, after which no further increase in RALS was observed. Thus, at the concentrations used in this study, short-term shearing should have minimal or no effect. Note that at higher concentrations this sensitivity could become a substantial issue.

Although recovery was inconsistent, the % non-aggregation demonstrated a modest but steady decline (that is % aggregate increased) throughout the Shear Stress test.

Slow Freeze-Thaw in PBS

To characterize AIC in PBS, the molecules' sensitivity to repeated freeze-thaw cycles was determined. This data was also used to determine how samples should be stored prior to additional analysis. Samples were stored at −80° C. at 460 μg/mL in PBS. Five Eppendorf tubes were prepared with 1 mL sample at 30 μg/mL in PBS, and one 200 μL sample was prepared that was not frozen as a control. All samples were frozen slowly at −80° C. by placing them in a box in the freezer. After freezing was complete, all five 1 mL aliquots were thawed on the bench top (room temperature). One aliquot was then analyzed by IF and RALS (which are examined simultaneously) and EF (total 800 μL), while the remaining four were refrozen at −80° C. for at least 2 hours. The analyzed 200 μL of sample remaining was labeled and refrozen for future analysis by HPLC. This process was repeated until five freeze-thaw cycles had been completed and examined. Variability in RALS was observed in the first freeze-thaw sample, resulting in altering the RALS procedure to include a degassing step just prior to analysis in all subsequent experiments.

The RALS data indicates that AIC in PBS (10 Mm Sodium Phosphate, 141.7 mM NaCl, pH 7.2) does not undergo aggregation and precipitation in response to increasing temperature. Repeated cycles of freeze-thaw do not appear to alter the molecule's response to a temperature ramp, since there was no increase in RALS as the sample were heated.

The process of freezing and thawing by itself may alter the aggregation of AIC. Thus, the RALS values were analyzed.

Examining the initial RALS of each sample immediately after thawing indicates that there is some aggregation of AIC in response to freeze-thawing. A single cycle of freeze-thaw is sufficient to increase RALS. The maximum increase occurred after 3 freeze-thaws.

IF measures Trp fluorescence. Since Trp has an emission max of 355 nm in a polar environment and 305 nm in a non-polar environment, the lower the ratio, the more polar the environment the Trp residues are exposed to, and the more unfolded the molecule. The effect of freeze-thaw on AIC conformation as measured by IF.

The IF ratio initially decreased as the temperature increased, suggesting conformational changes associated as a function of temperature, resulting in increasing the Trp residues' exposure to the buffer. At approximately 55° C. the molecule undergoes a substantial conformational change, suggested by the increase in IF ratio. This conformational change is not accompanied by a detectable aggregation, either visually in the fluorimeter cuvette or by RALS measurement.

Other than the most difference between FTI and the other samples examined by IF, repeated freeze-thawing does not affect AIC. These data support the data obtained by RALS.

The external, non-covalent, polarity-sensitive fluorescent probe, ANS has an emission max of 520 nm in a polar environment and 490 nm in a non-polar environment. Therefore, a ratio of 520/490 is indicative of the apparent hydrophobicity of AIC solution examined. A higher ratio indicates that the molecule is more hydrophilic and a lower ratio indicates that it is exposing hydrophobic domains for ANS binding.

Since the EF ratio increases up to approximately 40° C., the molecule is undergoing continuous conformational changes resulting in exposing less hydrophobic domains. The shifts at −40° C., −60° C. and −85° C. reflect conformational changes of AIC at those temperatures.

The freeze-thawed samples that were stored at −80° C. after the fluorimetry experiments were thawed and injected on a SEC-HPLC column.

The HPLC results suggested some slight degradation in response to repeated freeze-thawing.

Slow Freeze-Thaw Study Conclusions

The temperature at which the molecule begins to expose more hydrophobic residues by EF (Tm about 40° C.) is slightly lower than the temperature at which Trp residues begin to experience a more polar environment as shown by its IF profile (Tm about 50° C.). Thus, these two methods support each other and suggest that AIC begins to unfold between 40° C. and 50° C.

The conformational changes AIC experienced as a result of elevated temperature result in some aggregation. All three assays exhibited similar profiles among the different freeze-thaw samples, suggesting that AIC is relatively stable to repeated slow freeze-thawing.

Examination of Free Sulfhydryl Content in AIC: PyMal Assay.

PyMal [N-(1-pyrene) maleimide] solubilized in DMSO (Dimethyl Sulfoxide) is an extrinsic —SH specific probe used to detect the possible presence of free —SH groups in the molecule. When PyMal reacts with a free sulfhydryl group, it becomes fluorescent, with peak fluorescence at 374 nm and 394 nm. A 20-fold molar excess of PyMal was added to a sample of AIC at 30 μg/mL and samples incubated for 30 minutes in the presence of either 6M Guanidine or 10% SDS to unfold the molecule. The data has buffer samples subtracted from the fluorescent values. Data suggest that there are no free sulthydryls groups concealed within the molecule in its native state, since the PyMal fluorescence was identical when comparing the native PBS and SDS-pretreated samples. Guanidine appeared to suppress the reaction of PyMal with AIC. Since the PyMal fluorescence increased over time, the data also suggested that the molecule potentially has free sulfhydryl groups exposed even in its native state that could potentially result in aggregation. The data do not provide quantifiable measurements of free sulfhydryls.

Effect of Ionic Strength on AIC over Time and Temperature

Different ionic strengths were examined on AIC as a function of time and temperature followed by pH studies. To maintain consistency and allow comparison between such studies, they are all performed in a common buffer system referred to herein Base Buffer (BB). BB is a multi-buffer system designed to facilitate easy pH transitions while using a minimal concentration of buffer to reduce stability affects from the buffer itself. Typically, a 10×-strength solution is prepared as follows:

Preparation of 10X BB

| Chemical | 10x concentration | g/L for 10x |
|---|---|---|
| Glycine | 20 mM | 1.50 |
| Citric Acid | 20 mM | 4.20 |
| Hepes | 20 mM | 4.76 |
| MES | 20 mM | 4.26 |
| Tris | 20 mM | 2.43 |

Preparation of AIC in BB at Various Ionic Strengths

For use, the 10× BB is diluted to 1× (resulting in a final concentration of 2 mM for each buffer component), desired components added, and pH is adjusted as required. For the ionic strength studies presented in this report, each BB buffer was prepared with varying concentrations of NaCl (0 mM, 10 mM, 100 mM, 500 mM) and the solution adjusted to pH 7.2 in order to match the PBS composition. AIC (about 300 μg/condition) was dialyzed in Slide-A-Lyzer dialysis cassettes against BB with varying NaCl concentrations. The dialysis buffer was changed three times, with the second incubation occurring overnight. After recovery, samples were diluted and then examined by UV Spectrophotometry to determine the concentration. Subsequently, the samples were further diluted to yield the final desired concentration of 30 μg/mL. In a biosafety hood, samples were sterilized using 0.2 gm PES filters into 15 mL sterile tubes, and then aliquoted into 1.5 mL sterile cryovials (polypropylene, Corning cat. no. 430659). These samples were stored at 4° C. until the next morning, where they were placed in storage boxes in incubators. For Stability Studies, two sets of about 1.1 mL samples were placed at 30° C., and one set was placed at 40° C. The remaining sample set was stored at 4° C. until the samples were analyzed by EF, IF; RALS and by pH Titration (see below).

UV Spectrometry Analysis of Dialyzed AIC Before Final Dilution

| Condition | Ave. $A_{280}$ | Concentrationm (mg/mL) | % Recovery |
|---|---|---|---|
| CF | 0.510 | 39.8 | 102.9 |
| 0 mM NaCl | 0.585 | 45.5 | 105.5 |
| 10 mM NaCl | 0.543 | 42.5 | 98.6 |
| 100 mM NaCl | 0.515 | 40.0 | 92.8 |
| 500 mM NaCl | 0.454 | 35.2 | 81.7 |

AIC Formulations with Different Ionic Strengths Monitored by RALS Samples prepared as described above and after filtering were examined by UV Spectrophotometry to confirm the final concentration. They were examined during a temperature ramp by IF, RALS, and EF. Aliquots from these samples were frozen for later examination by SEC-HPLC.

The increase in RALS in the 500 mM condition indicates that the molecule forms aggregates when placed in high ionic strength conditions at higher temperatures. All other conditions do not exhibit detectable aggregation by this assay.

In order to accelerate instabilities in AIC, the ionic strength samples presented here were also incubated at 30° C. and 40° C. for 7 days ($t_7$) and analyzed by RALS, IF, and EF. Aliquots from these samples were frozen for later examination by SEC-HPLC.

The 40° C. 7 day incubation looks nearly identical to the results obtained from the 30° C. incubation. The only difference is a small increase in RALS in the 100 mM and 500 mM NaCl conditions in samples incubated at 40° C. (FIG. 1). This suggests that this higher temperature may reveal subtle differences in AIC behavior as examined with RALS. Similar results were obtained in the same formulations incubated for 14 days at 30° C. As shown in FIG. 1, the 500 mM NaCl formulation exhibited a substantial increase in aggregation as determined by RALS.

AIC Formulations with Different Ionic Strengths Monitored by IF

In the ionic strength RALS study, samples were simultaneously examined for IF changes during the RALS Temperature Profile.

As the low/high IF emission wavelength ratio increases, the molecule is changing conformation in such a way that Tryptophans (Trp) are being sequestered in a more hydrophobic environment. A lower ratio indicates the Trp residues are in a polar environment, and this change in ratio correlates with the molecule's unfolding.

As the temperature increases, AIC exhibits a conformational change with a Tm of about 50° C., which is the same for all compositions. However, the 500 mM NaCl sample exhibits the greatest conformational change, followed by the 100 mM sample. The composition, which contains 141 mM NaCl, exhibits a conformational change equivalent to that observed for the 100 mM sample, as judged by the IF ratio. These data suggest high ionic strength may be detrimental to the stability of the AIC molecule.

The Stability of AIC was Examined by IF Using the t7 Samples.

The t7 samples indicate that at lower ionic strength conditions, the AIC molecule exhibits conformation changes indicative of unfolding (based on the Guanidine Titration). All formulations display the same conformational changes (IF ratio changes at the same Tm) as the temperature increases, but the lower IF ratios in the lower ionic strength conditions indicate that AIC's Trp residues are more exposed to a polar environment.

The samples incubated for 7 days at 40° C. did not exhibit the dramatic conformational changes at elevated temperatures observed in samples incubated at 30° C. However, the IF ratio at room temperature followed the same pattern as the 30° C. samples. The 500 mM NaCl formulation exhibited a substantial change in conformation as determined by IF.

AIC Formulations with Different Ionic Strengths Monitored by EF

Ionic strength samples were temperature-ramped and examined using extrinsic fluorescence.

The results from a 7-day 40° C. incubation are similar to the 30° C. incubation results. A decrease in the EF ratio in the high ionic strength composition suggests that AIC changes conformation to expose more hydrophobic domains in this condition at room temperature. This increased exposure of hydrophobic domains may lead to increased aggregation as these hydrophobic domains bind. As the temperature is increased, the high ionic strength samples undergo a greater conformational change. These EF data support the results from the RALS and IF experiments, and suggest that high ionic strength is not a desirable condition for AIC.

AIC Formulations in Different Ionic Strengths Examined by SEC-HPLC

Samples from the ionic strength fluorimetry studies were frozen and stored at −80° C. until analysis by SEC-HPLC.

After ramping the temperature to 90° C., samples were cooled, then transferred to Eppendorf tubes and stored at −80° C. until analysis by SEC-HPLC. An additional NaCl to untreated sample set was also kept at −80° C. The NaCl to demonstrated high % non-aggregation.

The Temperature Ramped samples from $t_7$-30° C. and $t_{14}$-30° C. Studies Were Examined.

There were no substantial differences in results obtained in samples incubated at 30° C. versus 40° C. for 7 days, except in the 500 mM NaCl condition. Overall, the % non-aggregation was higher in samples not subjected to a Temperature Ramp, and Percent Total Recovery (measured by the peak area from chromatography) was lower after the Temperature Ramp.

Figure 2A:
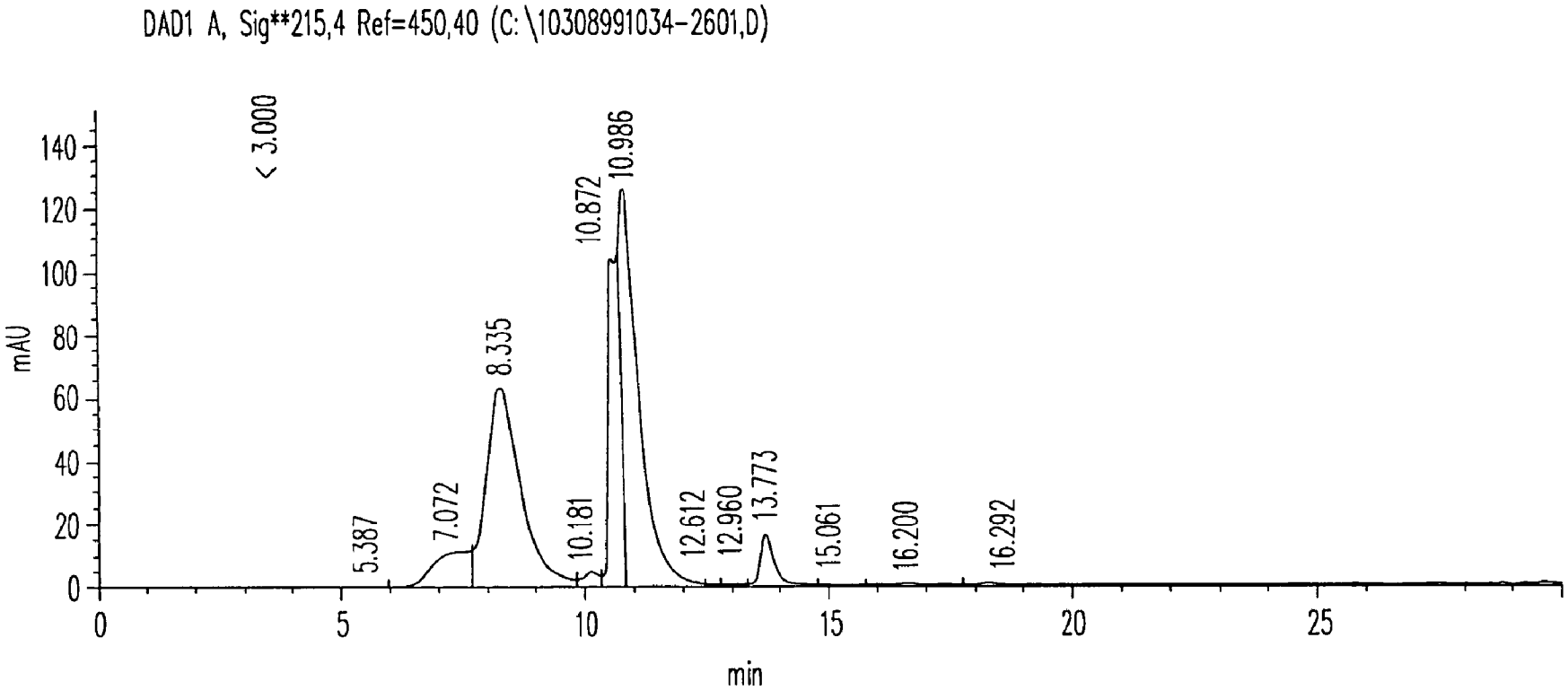
FIGS. 2A-2C show SEC-HPLC Chromatograms of AIC in 0.1M NaCl Base Buffer (BB) at $t_7$ (30 degrees C.) as discussed in Example 5.
Figure 2B:
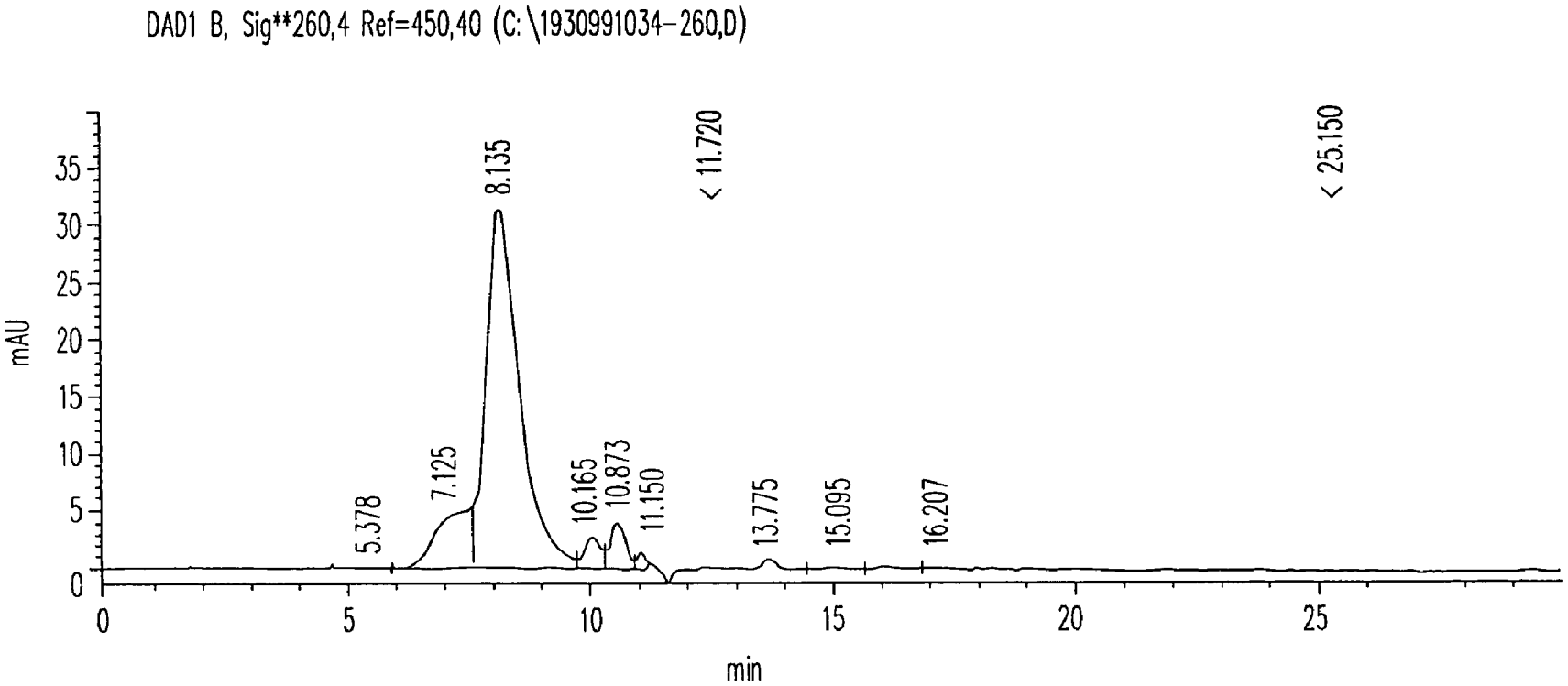
Figure 2C:
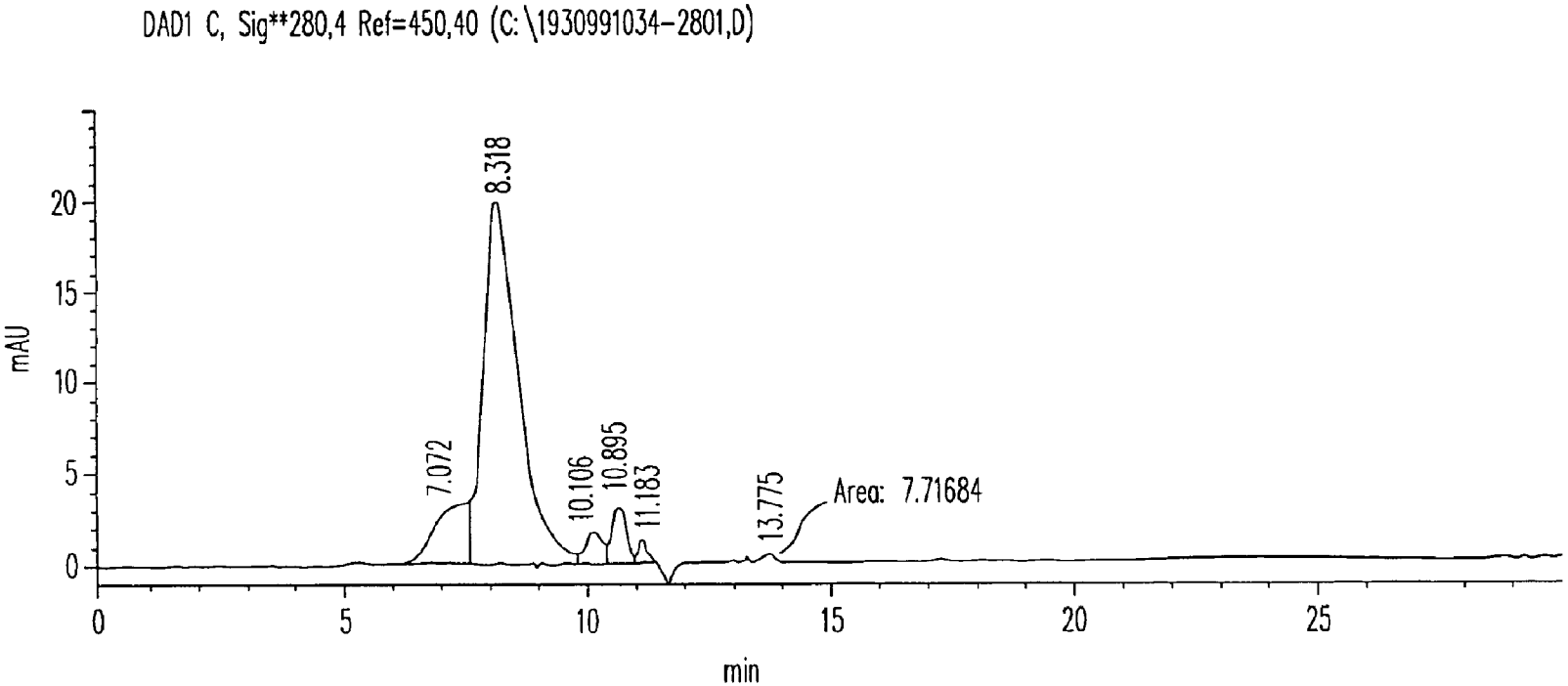

Incubating AIC for an additional 7 days (total of 14 days) at 30° C. resulted in modest decreases in Percent Recovery (measured by the peak area from chromatography) for all samples, and decreased % non-aggregation (that is, increased % aggregation) for the 100 MM and 500 mM NaCl conditions. The chromatograms of AIC formulated in BB containing 0.1 M NaCl and incubated at 30° C. for 7 days are shown in FIGS. 2A-2C for 215-, 260- and 280 nm. This shows the degradation of AIC as shown by SEC-HPLC. It displays the retention times of the degradant products (7, 10, 11, 13, 15, 16, 18 minutes). All assays demonstrate that AIC is less stable in higher ionic strength formulations.

Effect of pH as a Function of Ionic Strength on AIC in BB pH Titrations were performed at different ionic strengths. To examine the stability of AIC during pH changes, AIC prepared in BB at different NaCl concentrations was used. A 2.7 mL (2.4 mL for the 500 mM NaCl) sample preparation was placed in a fluorimeter cuvette and a pH probe was lowered into the solution. This permitted real time pH determination while obtaining RALS and IF data. The sample was then titrated with 5 μL of a 1N HCl or NaOH solution, resulting in a pH change of approximately 1 unit. After each addition, a 3 min period allowed the pH to equilibrate. Thereafter, the pH, RALS, and IF values were recorded. This entire process was performed over a 2-hour time course. For each condition, the sample's pH was adjusted from pH 7.2 to pH 3 to pH 11 and back to pH 7.2 (3>11) or from pH 7.2 to 11 to 3 and back to pH 7.2 (11->3). Low pH caused AIC to aggregate reversibly under conditions of low ionic strength.

As pH is decreased, AIC undergoes a reversible conformational change that results in Trp residues being exposed to a more hydrophobic environment. At 0 mM NaCl, the changes in the RALS and IF of AIC resulting from pH change are reversible.

As pH is decreased in the presence of 500 MM NaCl, AIC undergoes an irreversible conformational change that results in Trp residues being exposed to a more hydrophobic environment. If the pH is initially raised to 11, without first being lowered, the effect is less pronounced, although still not reversible.

pH titration at 10 mM and 100 mM demonstrated a NaCl concentration effect where high NaCl concentrations are detrimental to AIC.

Effect of Ionic Strength and pH Titration on AIC: SEC-HPLC Analysis

The NaCl samples were stored at 4° C. After 1-2 weeks, these samples were used in pH titration experiments. After titration, the samples were frozen and stored at −80° C. until analyzed by SEC-HPLC.

% non-aggregation was substantially reduced (that is, % aggregation increased) at high NaCl concentration (500 mm). The 100 MM NaCl sample exhibited a slight decrease in % non-aggregation when the pH was first raised to 11, then lowered to 3. Adjusting the pH to 3 and then 11 did not reduce % non-aggregation for the 100 mM NaCl composition.

Monomer Recovery was calculated relative to a control sample thawed and prepared prior to injection on the HPLC. Monomer Recovery was reduced at 500 mM NaCl. In these 500 MM samples, a new peak appeared at approximately a retention time of 10 minutes that was not as large in any other HPLC chromatogram presented in this report. This peak substantially increased the apparent Percent Total Recovery for the 500 mM NaCl samples. These data support the fluorimetry data that suggested a high NaCl concentration destabilizes AIC.

Effect of pH as a Function of Time and Temperature on AIC in BB

For the initial pH study, a series of BB buffers (0 mM NaCl) was prepared at pH ranges from pH 3 to pH 11. AIC (about 150 μg/formulation diluted in BB pH 7 to 75 μg/mL) was dialyzed in Slide-A-Lyzer dialysis cassettes against BB with varying pH at 4° C. using freshly thawed AIC material. The dialysis buffer was changed three times, with the third buffer exchange dialyzing overnight. After recovery, samples were examined by UV spectrophotometry to determine the concentration, and then diluted to yield the final desired concentration of 30 μg/mL. In a biosafety hood, samples were sterilized using 0.2 μm PES filters into 15 mL sterile tubes, and then aliquoted into 1.5 mL sterile cryovials (polypropylene, Corning cat. no. 430659). These samples were placed in storage boxes in humidity-controlled incubators. Three sets of about 1.0 mL samples were placed in 30° C. conditions, and one set was placed in 40° C. The remaining sample was stored at 4° C. until all samples were analyzed by EF, IF, RALS. Remaining material was frozen for subsequent analysis by HPLC.

Prior to using any samples, AIC concentration was determined. The summary of these results is presented in Table 9. AIC concentration was measured using absorbance at 280 nm. Results from the recovery of AIC after dialysis into BB is presented with the to sample concentrations. The pH 3, pH 4, and pH 5 samples had anomalously high readings (as indicated by Percent Recovery) and so were diluted using volumes based on the results from the other samples.

Note that all recoveries are greater than 100%. This is likely due to the fact that AIC determination was done without diluting the sample. Thus, the UV spectrophotometer readings were well above 1, where accuracy and linearity are reduced. This could also have affected the dilution calculations, resulting in the more varied concentrations.

TABLE 9 pH Samples: AIC concentration based on $A_{280}$ of AIC at $t_0$-$t_{14}$

| Sample | % Dialysis Recovery | $t_0$ (μg/mL) | $t_7$ 30° C. (μg/mL) | % of $t_0$ | $T_7$ 40° C. (μg/mL) | % of $t_0$ | $T_{14}$ 30° C. (μg/mL) | % of $t_0$ |
|---|---|---|---|---|---|---|---|---|
| *PBS C. | 102.1 | 27.53 | 26.49 | 96.2 | 28.46 | 103.4 | 27.19 | 98.8 |
| pH 3 | 148.6 | 31.31 | 27.80 | 109.1 | 21.25 | 83.4 | 21.83 | 85.6 |
| pH 4 | 131.6 | 25.49 | 34.81 | 100.8 | 25.11 | 72.7 | 38.05 | 110.2 |
| pH 5 | 129.1 | 34.54 | 33.16 | 100.8 | 34.20 | 104.0 | 33.23 | 101.0 |
| pH 6 | 114.3 | 32.89 | 30.23 | 105.0 | 30.85 | 107.1 | 30.04 | 104.3 |
| pH 7 | 110.0 | 28.80 | 29.84 | 104.0 | 30.69 | 107.0 | 30.04 | 104.7 |
| pH 8 | 111.9 | 28.69 | 28.61 | 99.4 | 29.57 | 102.8 | 29.19 | 101.5 |
| pH 9 | 111.9 | 28.77 | 30.81 | 100.4 | 31.62 | 103.0 | 30.15 | 98.2 |
| pH 10 | 112.0 | 30.69 | 29.69 | 101.6 | 31.12 | 106.5 | 31.35 | 107.2 |
| pH 11 | 111.3 | 29.23 | 29.96 | 102.9 | 31.66 | 108.7 | 30.11 | 103.4 |

*PBS Control = 10 mM Sodium phosphate, 141.7 mM NaCl at pH 7.2

AIC concentration was also determined using A260, and the results were similar but not identical to the results obtained at A280. The stability incubations did not alter the concentrations substantially from the $t_0$ values.

AIC Formulations at Different pH Monitored by RALS

For the pH study, the pH samples were monitored using RALS during a temperature ramp from 20° C. to 90° C. over 30 minutes. In order to accelerate instabilities in the molecule and to differentiate between the stability of different formulations, AIC was incubated at 30 and 40° C. for 7 and 14 days ($t_7$ and $t_{14}$). Samples prepared in BB with different pH were examined by RALS in a temperature profile.

Only the low pH formulations (pH 3 and pH 4) exhibited differences from the rest of the samples at $t_0$. These two formulations exhibited substantial aggregation as measured by RALS. All samples were clear prior to applying the temperature ramp. After reaching 90° C., only the pH 3 sample became cloudy. The rest remained clear. Samples prepared in BB with different pH values were again examined in temperature profiles after incubating them for 7 days at 30° C.

Based on RALS, after incubation at 30° C. for 7 days low pH (3-5) induced AIC to aggregate as judged by RALS readings. After incubation at 40° C. for 7 days, formulations at extreme pH (3-4, and 10-11) demonstrated less stability resulting in the formation of aggregates. Increasing temperature induced the formation of additional aggregates at low pH (pH 4) while disaggregating AIC at high pH (both pH 10 and pH 11). Temperature had no apparent affect on aggregation at pHs between pH 6 and pH 9.

Incubating at 30° C. for 14 days resulted in an increase in aggregation at pH 4. All other formulations were similar to the $t_0$ and $t_7$ data.

The RALS values also provide insight into the stability of AIC at different pH.

Acidic pH (3-5) resulted in increased aggregation, which increased with incubation over time at 30° C. or 40° C. At alkaline pH (10 and 11), only incubation at 40° C. resulted in aggregation.

AIC Formulations at Different pH Monitored by IF

The pH samples were also examined using IF during temperature ramps before and after incubation at 30° C. and 40° C.

The formulation at pH 3 exhibited a much higher IF ratio. All formulations exhibited a temperature transition, with Tm being lower for lower pH samples. These results indicate that a low pH caused a substantial change in conformation in AIC, since the overall IF ratio was substantially higher at pH 3-pH 6. pH 3 exhibited an even higher IF ratio. At the 30° C. incubation it started at 1.55 and steadily increased over the temperature profile, ending at about 2.3 at 90° C. At pH 7 and above, the molecule shows no conformational changes at elevated temperatures. After the 40° C. incubation both pH 3 and pH 4 were off scale (high) for the entire length of the profile. The initial IF ratios confirm the results obtained by the temperature profiles.

These results indicate that a low pH caused a substantial change in conformation in AIC, since the overall IF ratio was substantially higher at pH 3-pH 6.

AIC Formulations at Different pH Monitored by EF

The pH samples were also examined using EF during a temperature ramp and with long-term incubation at 30° C. Both the $t_0$ and $t_7$ samples are presented below.

Figure 3:
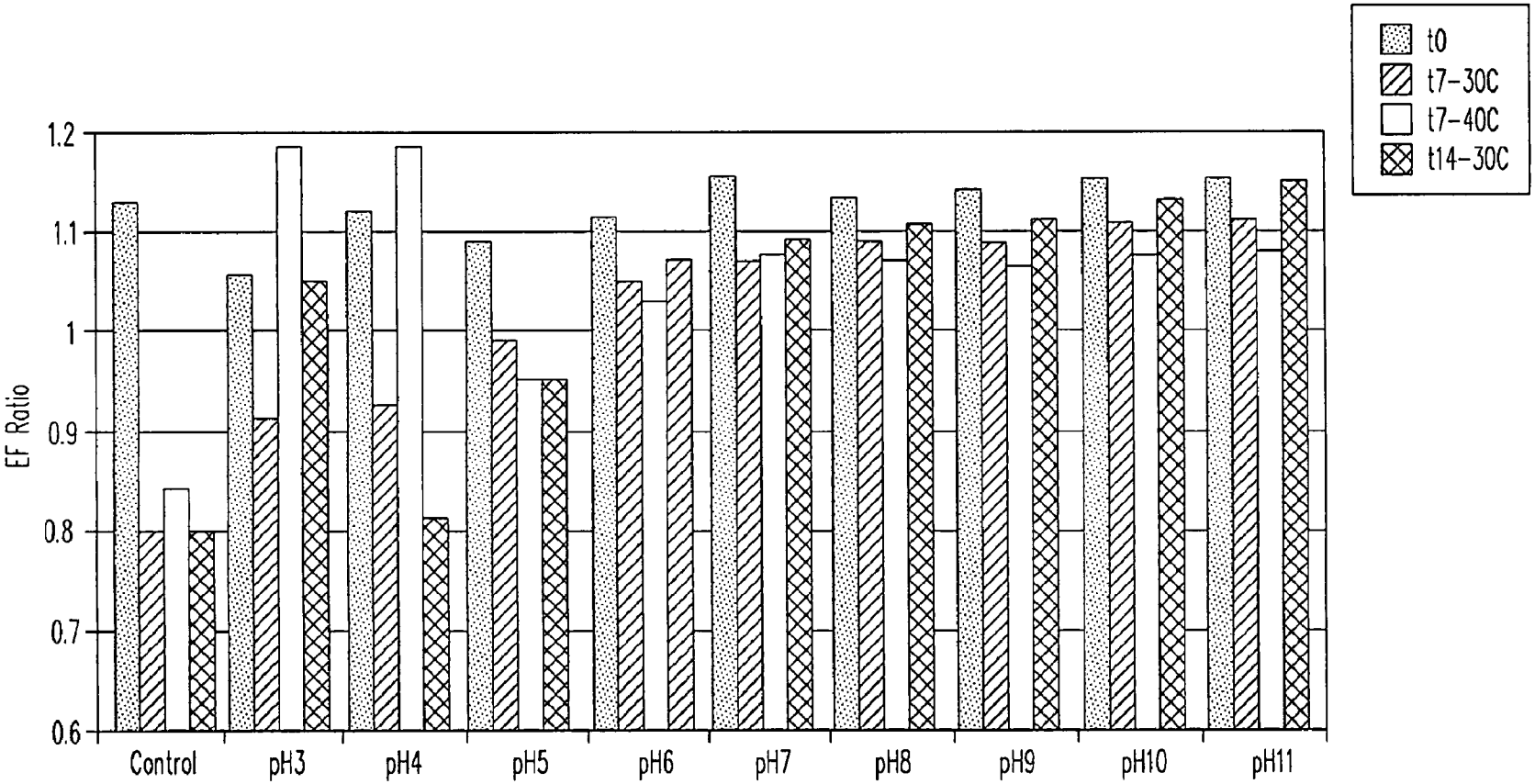
FIG. 3 shows the effect of pH, time and temperature on AIC as measured by Extrinsic Fluorescence as discussed in Example 5. Control is 10 mM Sodium Phosphate, 141.7 mM NaCl, pH 7.2. (The bars are from left to right, t0, t7-30, t7-40, t14-30, for each pH value).

With the exception of pH 3, the acidic samples exhibited a substantial decline in EF ratio over the 14 day stability study, indicating that the molecule has more hydrophobic domains exposed at these pH formulations. This supports the previous results at $t_0$ and $t_7$. See FIG. 3.

The lower the EF ratio, the more hydrophobic regions are exposed for the external probe ANS to bind. The data suggest that the formulations with pH 3 through pH 6 induced substantial conformational changes causing increased hydrophobicity, which could lead to aggregation. These data are supported by the RALS data as well as the pH titration data. The increase in EF ratio at pH 3 after extended incubation may be the result of complete degradation of the molecule.

AIC Formulations Containing Different Buffers Examined by SEC-HPLC

Figure 4A:
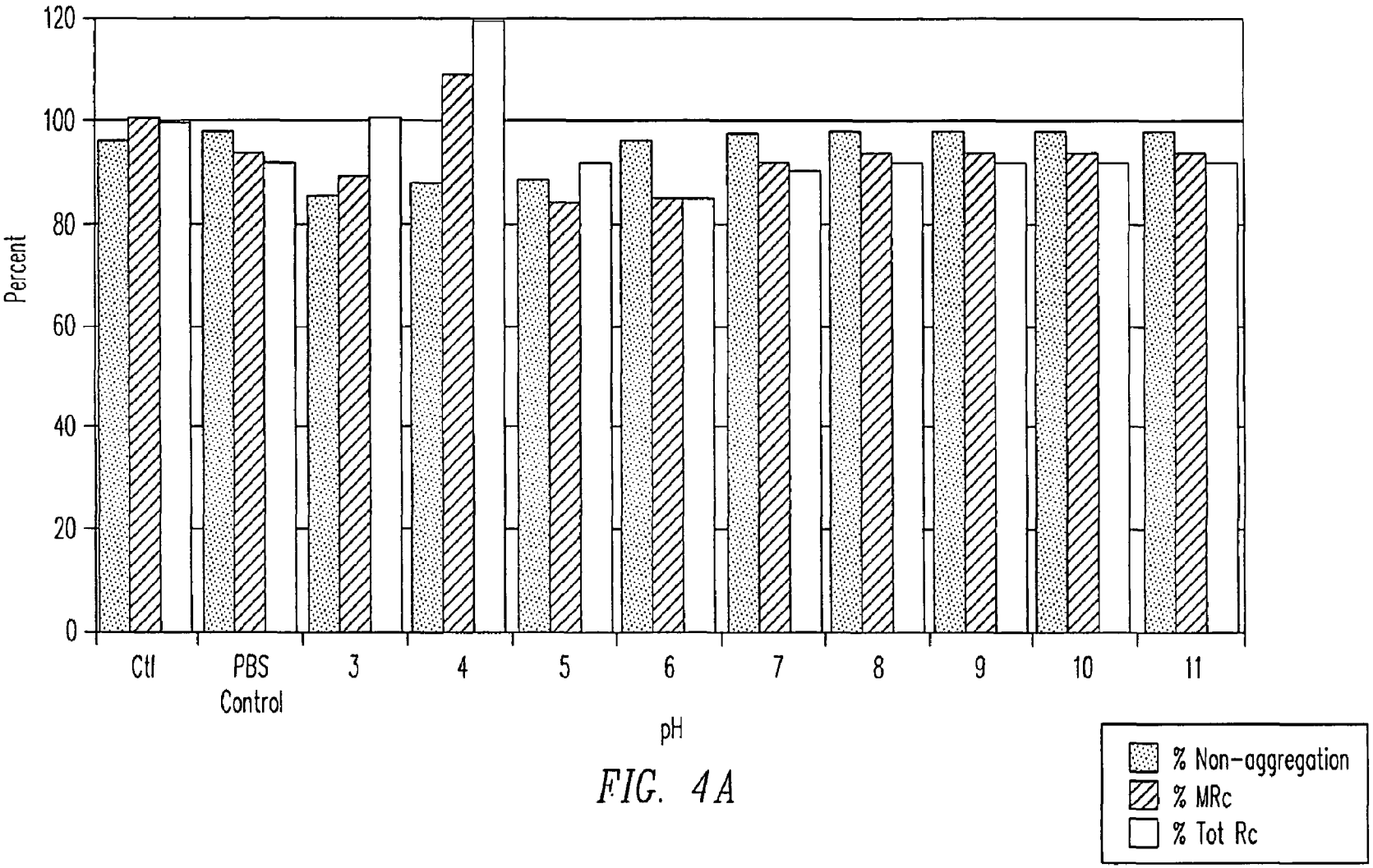
FIGS. 4A-4C.
Figure 4B:
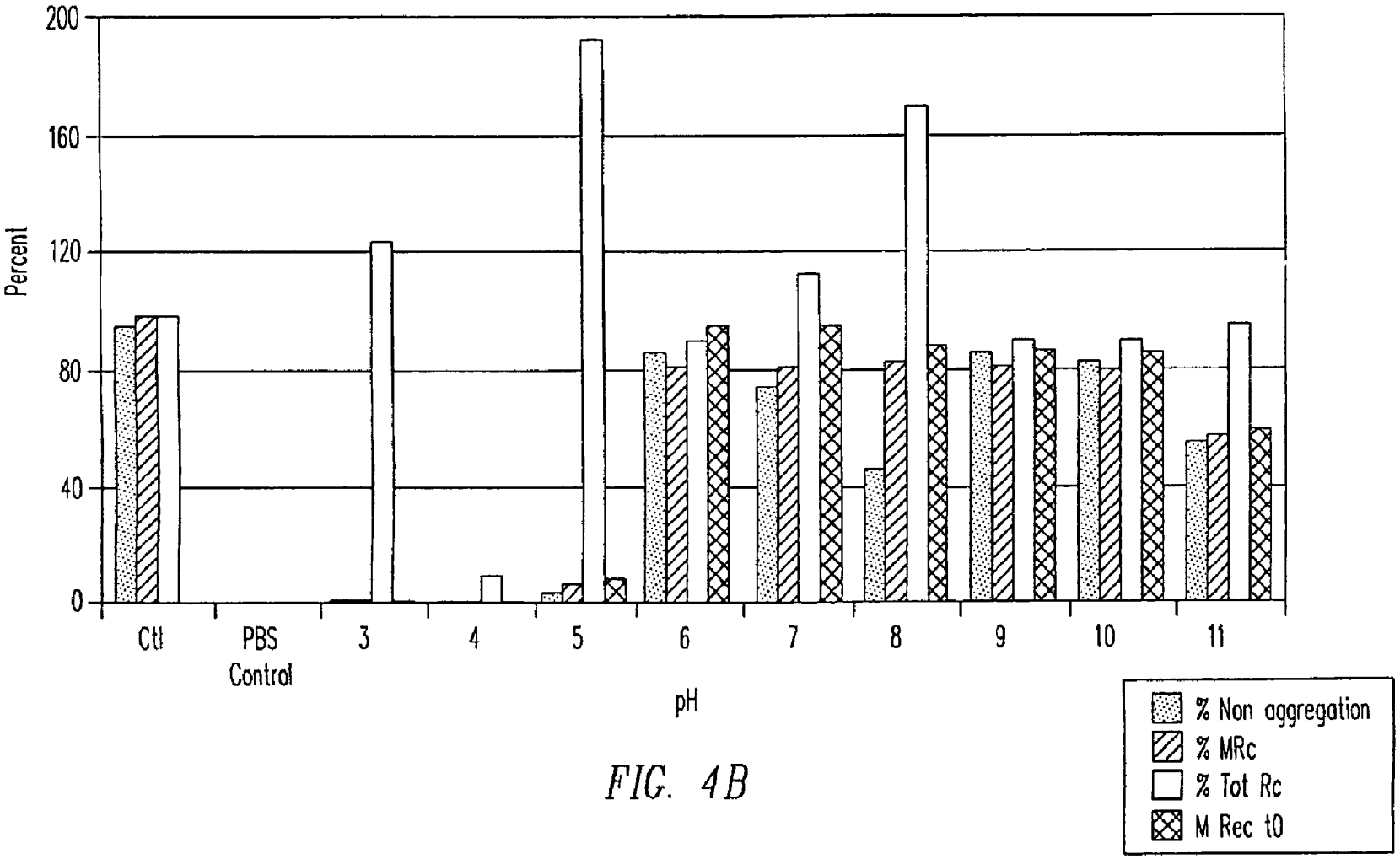
Figure 4C:
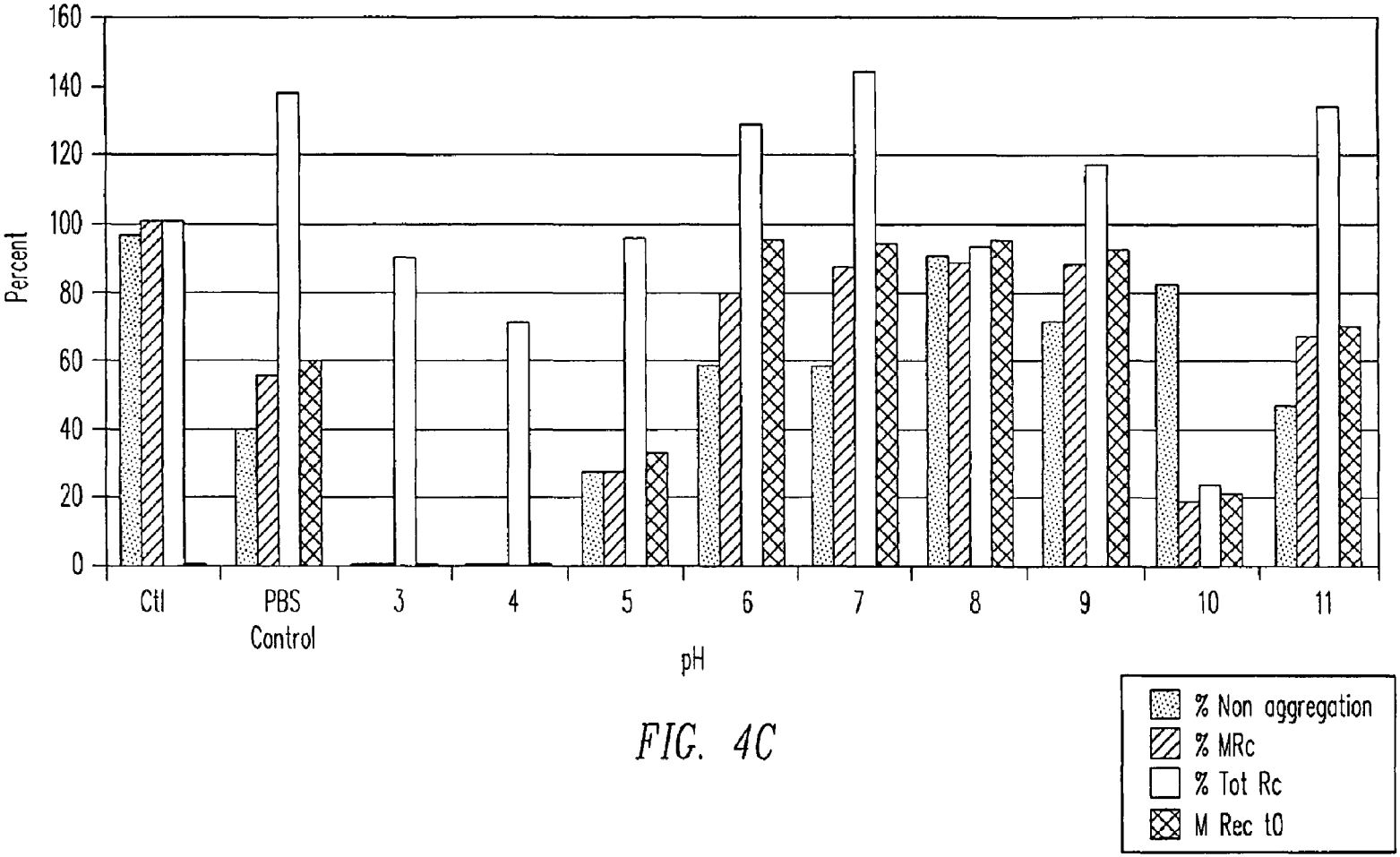

Samples prepared for the pH study were frozen and stored at −80° C. until analyzed by HPLC. See FIGS. 4A-4C. % non-aggregation and Monomer Recovery (MRc) are higher at alkaline pH (pH 7 to pH 11). MRec t0 is monomer recovery at time 0.

Incubation at 30° C. for seven days resulted in a higher % non-aggregation and Percent Recovery than incubation at 40° C. Incubation at 40° C. degraded AIC to the extent where a complete loss of the molecule at pH 3-5 and a reduced Percent Recovery at pH above 5 were observed. Incubation at 30° C. for 14 days caused a decrease in % non-aggregation (that is, increase in aggregation) for all samples except at pH 8.

Incubation for 14 days at 30° C. had a substantial effect on the pH 5, pH 10 and pH 11 samples compared to incubation for 7 days. There was only a modest effect on the samples at pH 6 through 9 compared to the effect of a 7-day incubation at 30° C. Based on the complete destruction of AIC at low pH during the stability studies, AIC was shown to have the greatest stability at pH 7-9.

The assays as described herein have been shown to be good indicators for AIC stability and are predicted to be good indicators for the structural stability of any conjugate molecule: RALS, IF, EF and SEC-HPLC. Based on the results of the above experiments, the following parameters were followed for design of compositions that provide for structurally stable conjugate molecules. The study will be designed to test components with pK values between 7 and 9. No salt will be used (the ionic strength study did suggest that low concentrations may be viable for adjusting osmolarity in the final formulation, since 10 mM NaCl did not substantially impact the molecule's stability).

Tables 10, 11 and 12 were prepared based on preparation of a decision matrix for evaluation of components as tested by RALS, EF, IF and HPLC-SEC. The effects of time and temperature on AIC in various compositions was analyzed by fluorimetric assays and the results were scored by qualitative and comparative analysis in one of two ways. In some studies, compositions were numbered from best to worst (such as, 1 to 10, with 1 being the best) as judged by each assay at each time point. Each assay was scored for initial values, for changes in an acute temperature ramp, and for changes over time when incubated at 40 degrees C. ($t_0$ (0 time) vs $t_7$ (7 days), $t_{14}$ (14 days) and $t_{28}$ (28 days); smaller changes were given higher scores). The number was then converted to a score from 0 to 100, with 100 being the best. Other studies used the actual value from each assay rather then ranking the compositions. All these scores were averaged and reported in Tables 10, 11, 12. The HPLC results were scored by mathematically spreading the actual % non-aggregation and Recovery values for each incubation time point, that is 0, 7 days, 14 days and 28 days, over a range from 0-100. The results from all three wavelengths were averaged for the score. The $t_7$, $t_{14}$, and $t_{28}$ HPLC data were assessed separately in order to give a greater weight to these data.

The thermal stress studies on AIC indicated that 40 degrees C. would be useful in accelerated structural stability studies, as at this temperature the AIC is 10 degrees C. below its thermal unfolding transition of about 50 to about 60 degrees C. (as assessed by IF and EF studies). RALS experiments demonstrate that AIC aggregates and precipitates at about 75 to about 80 degrees C. The temperature appropriate for accelerated structural stability studies on other conjugate molecules can be determined by measuring the thermal unfolding transition temperature of the conjugate molecule to be analyzed and maintaining the temperature of the studies below about 10 degrees less than the unfolding transition temperatore. Such determinations can be made by methods known by the skilled artisan and by IF and EF methods disclosed herein. IF and EF of AIC was examined with and without an acute temperature ramp (30 minutes, from 20 degrees C. to 90 degrees C.).

Results from the pH study demonstrated that AIC is substantially more stable in formulations above pH 6.0. Based on these results, a study investigating compositions containing different components with pKa values ranging from pH 6.0 to pH 8.0 was initiated. Results are shown in Table 10. For Table 10 results, the components were prepared as follows. Samples were prepared by dialyzing about 145 μg AIC against each composition listed in Table 10. Each composition was pH adjusted to the desired value, and filtered using 0.2 μm Nalgene filters. Dialysis was performed at 4 degrees C. in Slide-A-Lyzer cassettes while stirring at 60 rpm in a 300 mL beaker, with 3 changes of dialysis buffer. Sterile buffer was aliquoted and stored at 4 degrees C. for use as controls in AIC determination and for injection on HPLC. After dialysis, the samples were filter-sterilized using 0.2 μm PES filters in a biosafety hood and aliquoted into 4 sterile cryovials. Three sets of each composition were prepared at 30 [μg·mL] *μg/mL* and placed in a 40 degree C. incubator. One set was used immediately for $t_0$ studies. Control composition is *10 mM* sodium [dibasic] phosphate [20 mM], *141.7 mM NaCl* at pH 7.2 (JT Baker); Benzoate (Ben) is sodium benzoate 20 mM (Sigma); Citrate (Cit) is sodium citrate at 20 mM (JT Baker); Histidine (His) is 20 mM (Sigma); Phosphate (Phos) is sodium dibasic phosphate 20 mM (JT Baker); and Succinate (Suc) is Succinic Acid at 20 mM, all at the indicated pH.

TABLE 10

Matrix for selection of component for maintaining pH conditions of AIC.

| | % Dialysis | | Base RALS | | Base EF | | IF Profile | | HPLC | | | |
|---|---|---|---|---|---|---|---|---|---|---|---|---|
| Carbo | Recovery | $t_7$ | $t_0$ | $t_7$ | $t_0$ | $t_7$ | $t_0$ | $t_7$ | MP | Rc | Deg | Score |
| *PBS C. | 100 | 100 | 70 | 70 | 70 | 50 | 75 | 40 | 50 | 50 | 50 | 65.9 |
| Ben6.5 | 70 | 100 | 70 | 90 | 75 | 60 | 85 | 60 | 95 | 90 | 90 | 80.5 |
| Ben7.0 | 80 | 100 | 50 | 50 | 80 | 70 | 90 | 65 | 95 | 95 | 95 | 79.1 |
| Cit6.5 | 80 | 60 | 75 | 90 | 70 | 70 | 90 | 40 | 50 | 40 | 50 | 65.0 |
| His6.5 | 100 | 100 | 60 | 85 | 85 | 80 | 75 | 60 | 95 | 95 | 95 | 84.5 |
| His7.0 | 100 | 100 | 70 | 75 | 90 | 85 | 80 | 90 | 95 | 100 | 90 | 88.6 |
| His7.5 | 100 | 100 | 75 | 80 | 100 | 100 | 100 | 95 | 100 | 100 | 100 | 95.5 |
| His8.0 | 100 | 100 | 65 | 95 | 100 | 80 | 100 | 100 | 95 | 100 | 85 | 92.7 |
| Phos7.0 | 95 | 100 | 75 | 90 | 85 | 80 | 95 | 80 | 95 | 95 | 90 | 89.1 |
| Phos7.5 | 100 | 100 | 100 | 100 | 85 | 60 | 95 | 80 | 95 | 95 | 95 | 91.4 |
| Phos 8.0 | 100 | 100 | 95 | 95 | 85 | 90 | 95 | 85 | 90 | 95 | 75 | 91.4 |
| Suc6.5 | 90 | 75 | 95 | 95 | 75 | 75 | 90 | 50 | 55 | 55 | 50 | 73.2 |

Key: Deg = Degradation products formed;
*10 mm Sodium Phosphate, 141.7 mM NaCl, pH 7.2

The results are shown above. From the decision matrix table, Histidine at pH 7.5; Histidine at pH 8.0; Phosphate at pH 7.5, pH 8.0, pH 7.0; and Histidine at pH 7.0 and pH 6.5 are selected for use in compositions.

In some examples Histidine at pH 7.5 is used in compositions comprising a conjugate molecule. The affects of various amino acid stabilizers on AIC were assessed. The set selected below were chosen based on their use as injectable parenteral agents in license drug products. The compositions comprising amino acids to be tested were prepared for dialysis with 20 mM Histidine and 50 mM of the amino acid and pH was adjusted to 7.5. The compositions were filtered using 0.2 μm Nalgene filters. As controls, the compositions containing Histidine alone were also prepared at 5 mM, 20 mM and 50 mM. All amino acids tested were obtained from Sigma. The results of amino acids are shown in Table 11.

TABLE 11

Matrix for Selecting the Amino Acid Stabilizers for AIC

| | | | | $t_7$ | | $t_{14}$ | | $t_{28}$ | | |
|---|---|---|---|---|---|---|---|---|---|---|
| | RALS | IF | EF | MP | Rc | MP | Rc | MP | Rc | Avg. |
| PBS C. | 53 | 14 | 28 | 40 | 31 | 29 | 9 | 49 | 40 | 33 |
| Ala | 45 | 57 | 79 | 99 | 74 | 98 | 61 | 96 | 62 | 74 |
| Arg | 30 | 44 | 52 | 65 | 39 | 68 | 31 | 66 | 40 | 48 |
| Asp | 65 | 47 | 38 | 73 | 1 | 84 | 32 | 79 | 43 | 51 |
| Cre | 51 | 45 | 65 | 0 | 31 | 1 | 3 | 0 | 2 | 22 |
| Glu | 68 | 46 | 51 | 77 | 20 | 79 | 41 | 75 | 40 | 55 |
| Gly | 59 | 50 | 79 | 59 | 100 | 95 | 73 | 100 | 69 | 76 |
| 5His | 54 | 55 | 88 | 96 | 84 | 95 | 75 | 99 | 65 | 79 |
| 20His | 43 | 53 | 74 | 95 | 80 | 90 | 66 | 96 | 61 | 73 |
| 50His | 45 | 56 | 73 | 86 | 80 | 95 | 72 | 97 | 63 | 74 |

TABLE 11-continued

Matrix for Selecting the Amino Acid Stabilizers for AIC

| | | | | $t_7$ | | $t_{14}$ | | $t_{28}$ | | |
|---|---|---|---|---|---|---|---|---|---|---|
| | RALS | IF | EF | MP | Rc | MP | Rc | MP | Rc | Avg. |
| Ile | 65 | 56 | 66 | 93 | 82 | 94 | 73 | 96 | 62 | 76 |
| Leu | 53 | 63 | 63 | 93 | 81 | 87 | 76 | 98 | 65 | 75 |
| Lys | 30 | 64 | 38 | 71 | 73 | 37 | 72 | 57 | 43 | 54 |
| Phe | 34 | 58 | 34 | 82 | 84 | 36 | 97 | 83 | 74 | 65 |

TABLE 11-continued

Matrix for Selecting the Amino Acid Stabilizers for AIC

| | | | | $t_7$ | | $t_{14}$ | | $t_{28}$ | | |
|---|---|---|---|---|---|---|---|---|---|---|
| | RALS | IF | EF | MP | Rc | MP | Rc | MP | Rc | Avg. |
| Pro | 58 | 66 | 75 | 93 | 72 | 99 | 66 | 92 | 58 | 75 |
| Trp | 28 | 66 | 43 | 59 | 92 | 24 | 72 | 23 | 52 | 51 |

Six Amino Acids were selected for use in developing Compositions. The six amino acids selected had similar stabilizing effects. They are: 5 mM Histidine, Glycine, Isoleucine, Leucine, Proline, and Alanine. For combination studies, Glycine was the primary selected Amino Acid.

To investigate other components that could potentially stabilize AIC, various Carbohydrates and surfactants were investigated. These components can be used as bulking agents if lyophilization developments is pursued. The study presented below assessed 10 carbohydrates and 4 surfactants as stabilizers. They were selected for the study based on their use as injectable parenteral agents. All compositions were prepared with the components listed in Table 12 using 20 mM Histidine at pH 7.5. As controls AIC in sodium dibasic phosphate 20 mM at pH 7.2 was used and compositions containing 20 mM Histidine. Fructose (Fru) at 3% (Sigma); Glucose (Glu) at 3% (Sigma); Lactose (Lac) at 3% (Sigma); Maltose (Mal) at 3% (all of Fru, Glu, Lac, and Mal are reducing sugars responsible for Maillard reactions in lyophilized and liquid formulations); Mannose (Man) at 3% (Sigma); Mannitol (Mtol) at 3% (Sigma); Sorbitol (Sor) at 3% (Sigma); Sucrose (Suc) at 3% (Sigma); Trehalose (Tre) at 3% (Sigma); Xylitol (Xyl) at 3% (Sigma); PEG 3350 (P3350 or P3) at 0.1% (Sigma); PEG 4000 (P4000 or P4) at 0.1% (Mallinckrodt); Tween20 (T20) at 0.1% (JT Baker); and Tween80 (T80) at 0.1% (JT Baker).

TABLE 12

Matrix for Selecting the Carbohydrate or Surfactant Components for AIC

| | | | | HPLC $t_0$ | | HPLC $t_7$ | | HPLC $t_{14}$ | | HPLC $t_{28}$ | | |
|---|---|---|---|---|---|---|---|---|---|---|---|---|
| | RALS | IF | EF | *MP | *Rc | MP | Rc | MP | Rc | MP | Rc | Avg. |
| PBS | 23 | 47 | 51 | 88 | 60 | 17 | 24 | 0 | 0 | 29 | 13 | 32.0 |
| Fru | 68 | 38 | 18 | 89 | 78 | 96 | 68 | 74 | 72 | 28 | 54 | 62.1 |
| Glc | 51 | 65 | 48 | 95 | 64 | 85 | 57 | 87 | 55 | 85 | 39 | 66.4 |
| His | 57 | 62 | 85 | 79 | 76 | 84 | 72 | 70 | 71 | 81 | 27 | 69.5 |
| Lac | 78 | 53 | 53 | 87 | 99 | 97 | 94 | 87 | 89 | 87 | 77 | 82.0 |
| Mal | 61 | 48 | 44 | 83 | 82 | 91 | 75 | 96 | 68 | 100 | 32 | 70.8 |
| Man | 74 | 36 | 36 | 94 | 97 | 95 | 87 | 76 | 92 | 62 | 44 | 72.0 |
| Mtol | 53 | 43 | 63 | 60 | 55 | 74 | 53 | 70 | 53 | 20 | 44 | 53.3 |
| Sor | 56 | 73 | 42 | 95 | 64 | 93 | 59 | 94 | 62 | 91 | 20 | 68.2 |
| Sue | 77 | 65 | 70 | 100 | 80 | 88 | 72 | 73 | 80 | 44 | 62 | 73.7 |
| Tre | 73 | 65 | 62 | 94 | 69 | 79 | 62 | 65 | 75 | 56 | 32 | 66.6 |
| Xyl | 41 | 69 | 48 | 90 | 68 | 90 | 66 | 89 | 67 | 49 | 42 | 65.5 |
| P3 | 43 | 53 | | 83 | 76 | 86 | 71 | 67 | 84 | 67 | 38 | 66.7 |
| P4 | 18 | 31 | | 83 | 80 | 88 | 74 | 59 | 89 | 75 | 37 | 63.2 |
| T20 | 46 | 60 | | 75 | 78 | 84 | 78 | 43 | 87 | 27 | 76 | 65.4 |
| T80 | 49 | 33 | | 71 | 84 | 88 | 84 | 56 | 94 | 30 | 61 | 65.0 |

*monomer %

**total recovery

The selection of four components from this study are: Lactose, Sucrose, and Mannose and Maltose. However, while Sucrose showed the best overall score, it had a poor response to incubation at 40° C. as assessed by % non-aggregation of AIC at $t_{28}$. The effects of the stability incubation were assessed with HPLC-SEC at $t_{28}$ for sucrose and sorbitol. The results demonstrate that the Sucrose containing composition had greater degradation products at 260 nm and 280 nm compared to the Sorbitol formulation. Because Lactose and Maltose are reducing sugars, and Mannose had poor HPLC results at $t_{14}$ and $t_{28}$, combination studies focused on Sucrose and Sorbitol.

Example 6

Combination Composition Studies

Preparation of Compositions for Combination Studies

Study 1

To investigate the effect of combining Components identified as good stabilizers (that is, that for provide for structural stability of conjugate molecules) for AIC, the study presented below assessed compositions containing combinations, including of 2 buffers, 2 Amino Acids, and 2 Carbohydrates. These Components were chosen for the study based on data obtained through 28 days of stability studies, except Carbohydrate, which was chosen from data through 14 days of studies. Compositions were designed to simplify comparison between changes in single Components while reducing the number of compositions required for assessment. Compositions were prepared with the Components listed in Table 13 (pH 7.5) using the combinations shown and the procedures as described herein. One set was used immediately for to studies.

TABLE 13

Compositions with Combined Components

| Composition | Histidine | Phosphate | Glycine | Isoleucine | Sucrose | Mannose | mOsm |
|---|---|---|---|---|---|---|---|
| 1 | 20 mM | — | 50 mM | — | — | — | 61 |
| 2 | 20 mM | — | — | — | 3% | — | 100 |
| 3 | 20 mM | — | 270 mM | — | | — | 289 |
| 4 | 20 mM | — | 50 mM | — | 7% | — | 297 |
| 5 | 20 mM | — | 175 mM | — | 3% | — | 287 |
| 6 | 20 mM | — | 115 mM | — | 5.15% | — | 300 |
| 7 | 50 mM | — | 20 mM | — | 7% | — | 298 |
| 8 | 5 mM | — | 115 mM | — | 5% | — | 281 |
| 9 | 20 mM | — | 50 mM | — | — | 4.5% | 334 |
| 10 | 20 mM | — | 50 mM | 50 mM | 5.3% | — | 291 |
| 11 | — | 20 mM | 50 mM | — | — | — | 93 |
| 12 | — | 50 mM | — | | 4.6% | — | 261 |
| 13 | — | 20 mM | 50 mM | | 6.2% | — | 305 |
| 14 | — | 50 mM | 50 mM | | 4.6% | — | 311 |
| | | | PBS control | | | | 483 |

Note:
Compositions were analyzed for osmolarity after final dilution and filtering (to compositions).

The A1C concentrations and recoveries at each time point were determined using absorbance at 280 nM, and are presented in Table 14.

Compositions were further analyzed by RALS, IF, EF and SEC-HPLC by methods as described herein.

To select compositions, a decision matrix table, Table 14 was constructed.

TABLE 14

Decision Table for Selecting the Components for Composition

| | RALS | IF | EF | $t_7$ *MP | *Rc | $t_{14}$ MP | Rc | $t_{28}$ MP | Rc | Avg. |
|---|---|---|---|---|---|---|---|---|---|---|
| PBS control | 32 | 36 | 62 | 25 | 52 | 0 | 34 | 1 | 10 | 37.0 |
| 1 | 75 | 79 | 71 | 90 | 100 | 94 | 95 | 90 | 68 | 85.8 |
| 2 | 76 | 70 | 68 | 84 | 91 | 84 | 100 | 79 | 76 | 81.8 |
| 3 | 45 | 78 | 63 | 95 | 87 | 88 | 91 | 95 | 77 | 80.3 |
| 4 | 88 | 73 | 56 | 96 | 91 | 92 | 91 | 83 | 79 | 84.1 |
| 5 | 70 | 76 | 58 | 88 | 83 | 87 | 90 | 89 | 73 | 78.1 |
| 6 | 84 | 73 | 60 | 89 | 90 | 86 | 95 | 86 | 82 | 81.4 |
| 7 | 92 | 64 | 47 | 81 | 72 | 24 | 83 | 55 | 75 | 67.9 |
| 8 | 87 | 78 | 66 | 90 | 82 | 92 | 90 | 82 | 83 | 80.4 |

TABLE 14-continued

Decision Table for Selecting the Components for Composition

| | RALS | IF | EF | $t_7$ *MP | *Rc | $t_{14}$ MP | Rc | $t_{28}$ MP | Rc | Avg. |
|---|---|---|---|---|---|---|---|---|---|---|
| 9 | 85 | 39 | 35 | 70 | 69 | 13 | 79 | 1 | 75 | 56.7 |
| 10 | 55 | 72 | 68 | 76 | 87 | 60 | 93 | 78 | 79 | 75.9 |
| 11 | 81 | 69 | 88 | 100 | 59 | 100 | 64 | 99 | 16 | 76.2 |
| 12 | 74 | 65 | 80 | 60 | 23 | 80 | 7 | 91 | 43 | 59.5 |
| 13 | 80 | 74 | 76 | 80 | 55 | 91 | 46 | 97 | 66 | 74.7 |
| 14 | 80 | 76 | 71 | 69 | 58 | 79 | 29 | 90 | 61 | 71.0 |
| PBS C. | 32 | 36 | 62 | 25 | 52 | 0 | 34 | 1 | 10 | 37.0 |

*monomer %
**total recovery

Based on the results of Table 14, compositions 3, 4, 6, and 8 were selected (all had similar results). Compositions 1 and 2 are control compositions and do not have sufficient osmolarity to be chosen as the final composition.

Comparing the various compositions, the following conclusions were drawn:

Increasing Glycine concentration and decreasing Sucrose concentration (Compositions 4-6) caused a decrease in stability. Inclusion of Mannose (Composition 9) in the place of Sucrose (Composition 4) resulted in a composition causing a considerable drop in stability. Adding Isoleucine (Composition 10) and reducing Sucrose (Composition 4) concentration resulted in a drop in stability. Phosphate buffered compositions (11-14) did not perform as well as Histidine buffered compositions overall. However, in the HPLC data alone, the Phosphate buffered compositions performed almost as well as the Histidine buffered compositions. Little difference was observed between compositions containing 5 mM (Composition 8) and 20 mM (Composition 6) Histidine, but 50 mM Hisitidine (Composition 7) caused a considerable decrease in stability.

Study 2

Preparation of Compositions for Combination Study 2

To further investigate the effect of combining components identified as good stabilizers, the study presented here assessed compositions containing 1 buffer, 2 Amino Acids, and 3 Carbohydrates as stabilizers. They were chosen for the study based on data obtained through 28 days of stability studies. Compositions were designed to explore the use of Sorbitol since the data from the 28-day incubation of AIC indicated that Sorbitol stabilizes AIC better than Sucrose.

Compositions were prepared with the components listed in Table 15. The pH of each composition was adjusted to 7.5, and then each composition was prepared as described herein.

TABLE 15

Compositions with Combined Components

| Composition | His | Phosphate | Gly | Leu | Sorb | Mal | Suc | mOsm* |
|---|---|---|---|---|---|---|---|---|
| 1 | 20 mM | | 50 mM | — | — | — | — | 68 |
| 2 | 20 mM | — | — | — | 3% | — | — | 182 |
| 3 | 20 mM | — | — | — | 4.6% | — | — | 273 |
| 4 | 20 mM | — | — | — | — | 8% | — | 251 |
| 5 | — | 20 mM | — | — | 4.3% | — | — | 306 |
| 6 | — | 20 mM | 50 mM | — | 3.5% | — | — | 332 |
| 7 | 20 mM | — | 50 mM | — | 3.80% | — | — | 280 |
| 8 | 20 mM | — | 50 mM | — | — | 7% | — | 270 |
| 9 | 20 mM | — | — | 50 mM | 3.80% | — | — | 282 |
| 10 | 20 mM | — | 50 mM | — | — | — | 7% | 290 |
| | | | PBS control | | | | | 476 |

*Actual osmolarity measured

The AIC concentrations and recoveries after dialysis and filtration (to), and after 7, 14 and 29-day incubation at 40° C. were determined using absorbance at 280 nm.

Compositions were further analyzed by RALS, IF, EF and SEC-HPLC by methods as described herein.

To select composition, a decision matrix table, Table 16 was constructed.

TABLE 16

| | RALS | IF | EF | $t_7$ MP | Rc | $t_{14}$ MP | Rc | $t_{28}$ MP | Rc | Avg. |
|---|---|---|---|---|---|---|---|---|---|---|
| PBS | 7 | 26 | 47 | 25 | 49 | 0 | 20 | 0 | 34 | 31.9 |
| C. | | | | | | | | | | |
| 1 | 78 | 79 | 75 | 96 | 65 | 89 | 58 | 86 | 73 | 76.4 |
| 2 | 84 | 70 | 73 | 96 | 60 | 95 | 55 | 91 | 60 | 76.5 |
| 3 | 75 | 79 | 62 | 88 | 97 | 94 | 96 | 91 | 97 | 86.9 |
| 4 | 52 | 34 | 40 | 100 | 84 | 99 | 84 | 97 | 41 | 71.1 |
| 5 | 68 | 52 | 59 | 99 | 58 | 93 | 29 | 88 | 60 | 71.5 |
| 6 | 67 | 62 | 42 | 93 | 45 | 79 | 44 | 79 | 54 | 62.0 |
| 7 | 69 | 84 | 41 | 94 | 87 | 95 | 81 | 97 | 77 | 81.1 |
| 8 | 55 | 45 | 45 | 98 | 91 | 98 | 81 | 99 | 81 | 77.7 |
| 9 | 53 | 80 | 57 | 98 | 97 | 92 | 88 | 91 | 87 | 83.2 |
| 10 | 76 | 68 | 47 | 99 | 96 | 97 | 96 | 95 | 54 | 80.2 |

Compositions 3, 7, 9 and 10 were selected. The four all had similar results

Comparing the various compositions, the following conclusions were drawn. Composition 10 was selected for use. Increasing Sorbitol concentration increased stability as demonstrated with Composition 2 vs. 3 and Composition 6 vs. 7. Replacing Leucine (Composition 9) with Glycine (Composition 7) caused a slight decrease in stability. Composition 3, which contained Sorbitol without Glycine or Leucine, proved to be a better stabilizer than compositions using Sorbitol combined with Glycine or Leucine. Compositions containing Histidine rather than Phosphate exhibited higher stability based on their overall score (Compositions 5 and 6), although Phosphate combined with Sorbitol stabilized AIC almost as well as a composition containing Histidine and Sorbitol when considering HPLC data alone (Composition 3 vs. 5).

Study 3: Component Combinations

Preparation of Compositions for Combination Study 3

After reviewing the 2 combination studies above, a combination study was prepared comparing the interactions of Glycine, Proline and Leucine with 3% Sorbitol and 20 mM Histidine. In addition, since AIC may not need carbohydrate for stability, various salts were investigated as an isotonic adjuster in AIC compositions. In the previous ionic strength studies, NaCl was used as a model compound. Although the data suggested that higher ionic strength is detrimental to AIC, in absence of stabilizer, this composition iteration was carried out with different salts or isotonic adjusters in the presence of Histidine as a stabilizer.

Compositions were prepared with the Components listed in Table 17 using the combinations shown. The pH of each composition was adjusted to 7.5, and the compositions prepared as described herein.

TABLE 17

Compositions with Combined Components

| Compositions | Histidine | Sorbitol | Glycine | Leucine | Proline | NaCl | mOsm* |
|---|---|---|---|---|---|---|---|
| 1 | 20 mM | 3% | — | — | — | — | 178 |
| 2 | 20 mM | 3% | 110 mM | — | — | — | 301 |
| 3 | 20 mM | 3% | — | 110 mM | — | — | 312 |
| 4 | 20 mM | 3% | — | — | 110 mM | — | 304 |
| 5 | 20 mM | — | 270 mM | — | — | — | 286 |
| 6 | 20 mM | 3% | — | — | — | 570 mM** | 1266 |
| | Histidine | KCI | Na Acetate | Na—$SO_4$ | $KH_2PO_4$ | | |
| 7 | 20 mM | 145 mM | — | — | — | — | 278 |
| 8 | 20 mM | — | 140 mM | — | — | — | 299 |
| 9 | 20 mM | — | — | 115 mM | — | — | 292 |
| 10 | 20 mM | — | — | — | 115 mM | — | 301 |

TABLE 17-continued

| Compositions with Combined Components | | | | | | | |
|---|---|---|---|---|---|---|---|
| 11 | 20 mM | — | — | — | — | 155 mM | 413 |
| 12 | 20 mM | — | — | — | — | — | 21 |
| | | | PBS control | | | | 480 |

*Actual osmolarity measured at $t_0$

**There was an error in the preparation of this composition. The composition was intended to be 57 mM NaCl.

The AIC concentrations and recoveries after dialysis and filtration ($t_0$), and after 7-, 14-, and 28-day incubation at 40° C. were determined using absorbance at 280 nm. Compositions were further analyzed by RALS, IF, EF and SEC-HPLC by methods as described herein.

Table 18 provides a matrix for selecting combinations of compositions.

TABLE 18

| Matrix for Selecting Combinations | | | | | | | | | | |
|---|---|---|---|---|---|---|---|---|---|---|
| | RALS | IF | EF | $t_7$ MP | Rc | $t_{14}$ MP | Rc | $t_{28}$ MP | Rc | Avg. |
| PBS | 47 | 87 | 49 | 57 | 64 | 33 | 33 | 0 | 1 | 49.1 |
| 1 | 76 | 91 | 68 | 99 | 95 | 97 | 81 | 99 | 68 | 87.5 |
| 2 | 89 | 91 | 47 | 99 | 84 | 95 | 78 | 93 | 73 | 85.0 |
| 3 | 85 | 91 | 46 | 99 | 93 | 98 | 91 | 95 | 85 | 88.6 |
| 4 | 85 | 90 | 47 | 100 | 97 | 100 | 98 | 98 | 82 | 90.2 |
| 5 | 87 | 92 | 55 | 97 | 96 | 95 | 97 | 82 | 97 | 90.4 |
| 6 | 25 | 87 | 42 | 25 | 53 | 0 | 28 | | | 45.1 |
| 7 | 83 | 90 | 50 | | | 67 | 71 | | | 75.5 |
| 8 | 87 | 90 | 41 | 76 | 77 | 64 | 56 | | | 70.8 |
| 9 | 77 | 89 | 47 | 59 | 43 | 30 | 16 | | | 56.8 |
| 10 | 85 | 89 | 38 | 65 | 38 | 46 | 25 | | | 59.3 |
| 11 | 81 | 90 | 44 | 43 | 49 | 22 | 11 | | | 55.0 |
| 12 | 81 | 90 | 57 | 99 | 90 | 96 | 87 | | | 87.9 |

Comparing the various compositions, the following conclusions were drawn. Salt cannot be used as an isotonic adjuster consistent with earlier observations that AIC is unstable in the presence of salt (Compositions 6-11). Composition 1 scored better in this round of composition than it had in the previous round, but it does not have sufficient osmolarity. Compositions containing Leucine or Proline with Histidine and Sorbitol (Compositions 3 and 4) provided better stabilization than compositions without Leucine or Proline (Composition 1). For stabilization, Leucine and Proline are better components than Glycine when they are combined with Sorbitol (Composition 3 and 4 vs. 2), but Glycine is a better stabilizer without Sorbitol (Composition 5) than either Composition 3 or 4.

Study 4

After reviewing the 3 combination studies, a final combination study was prepared to study the effects of components capable of maintaining the pH as desired. Since a composition containing 270 mM Glycine in 20 mM Histidine pH 7.5 performed well in previous studies, the compositions outlined in Table 19 were examined.

Compositions were prepared with the Components listed in Table 19 using the combinations shown. The pH of each composition was adjusted to 7.5, and the compositions were prepared according to the method described herein.

TABLE 19

| Compositions with Combined Components | | | | |
|---|---|---|---|---|
| Composition | Histidine | Glycine | Phosphate, monobasic | mOsm |
| 1 | 20 mM | 270 mM | — | 300 |
| 2 | — | 230 mM | 20 mM | 268 |
| 3 | 5 mM | 285 mM | — | 330 |
| PBS control | | | | 512 |

Compositions were prepared such that the use of Histidine versus Phosphate could be confirmed. The AIC concentrations and recoveries after dialysis and after filtration ($t_0$) after all time points were determined using absorbance at 280 run, and are shown in Table 20.

TABLE 20

| Compositions with Combined Components: AIC Concentration of AIC at $A_{280}$ | | | | | | |
|---|---|---|---|---|---|---|
| Sample | % Dialysis Recovery | $t_0$ (μg/mL) | % of $t_0$ | $t_7$ 40° C. (μg/mL) | % of $t_0$ | $t_{14}$ 40° C. (μg/mL) |
| PBS C. | 103.5 | 27.11 | 103.02 | 27.76 | 105.94 | 28.54 |
| 1 | 119.6 | 26.99 | 98.75 | 26.01 | 96.34 | 25.38 |
| 2 | 111.3 | 26.30 | 46.05 | 12.15 | 91.37 | 24.10 |
| 3 | 112.3 | 28.77 | 98.85 | 28.98 | 92.56 | 27.14 |

Protein concentrations for $t_{28}$ were not acquired.

Figure 5:
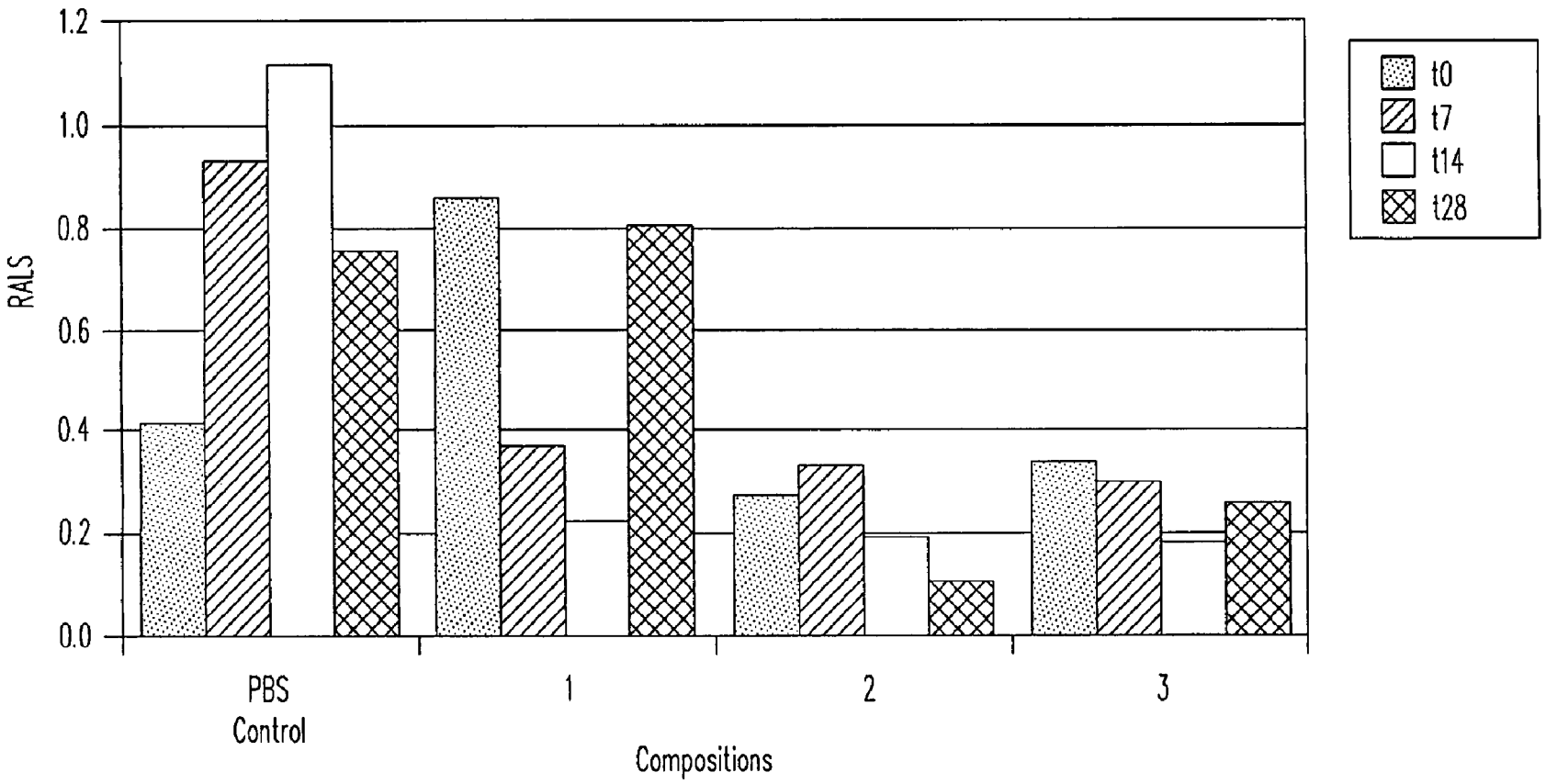
FIG. 5 shows the effect of combinations of components, time and temperature on AIC as measured by RALS as shown in the Examples. PBS Control is 10 mM Sodium Phosphate, 141.7 mM NaCl, pH 7.2. (The bars are from left to right, t0, t7, t14 and t28, for each composition).

Compositions were further analyzed by RALS, IF, EF and SEC-HPLC by methods as described herein. The results of RAL measurements are shown in FIG. 5.

To select composition(s) from this study, a decision matrix table (Table 21) was constructed.

TABLE 21

| Matrix for Selecting Combinaion 3 Components for AIC | | | | | | | | | | |
|---|---|---|---|---|---|---|---|---|---|---|
| | RALS | IF | EF | $t_7$ MP | Rc | $t_{14}$ MP | Rc | $t_{28}$ MP | Rc | Avg. |
| PBS Control | 33 | 80 | 31 | 25 | 58 | 0 | 44 | 0 | 12 | 42.6 |
| 1 | 79 | 87 | 54 | 100 | 55 | 97 | 79 | 97 | 66 | 80.0 |
| 2 | 82 | 83 | 47 | 95 | 24 | 85 | 11 | 72 | 80 | 66.6 |
| 3 | 83 | 87 | 68 | 99 | 97 | 100 | 93 | 100 | 95 | 92.6 |

Comparing the various compositions, the following conclusions were drawn. Compositions containing Histidine (1 and 3) provided better stability than those containing Phosphate (2). A composition with low Histidine concentration and high Glycine concentration (Composition 3) provided better stability than a composition with high Histidine concentration and a low Glycine concentration (Composition 1). The data suggest that AIC is most stable in the absence of NaCl. The best pH for AIC is 7.5 (range 7-9). AIC is not substantially shear sensitive. Temperatures above 40° C.

result in degraded AIC. Temperature and pH stresses both produce insoluble and aggregated species. The best component for maintaining pH for an AIC composition is Histidine at pH 7.5, followed by Histidine at pH 8.0, and Phosphate at pH 7.5 and pH 8.0. The most desirable Amino Acids for a stable AIC composition are: 5 mM Histidine alone, Glycine, Isoleucine, Leucine, Proline, and Alanine. Overall, the best Carbohydrates for a stable AIC composition are: Lactose, Sucrose, and Mannose and Maltose. Maltose and Lactose are reducing sugars. Looking at HPLC results alone, Sorbitol and Glucose provided improved stability over all carbohydrates except the reducing sugars. In some examples, the following compositions can be used for liquid composition of structurally stable AIC at temperatures between about 2° degrees and about 8° degrees C.: 5 mM Histidine, 285 mM Glycine; 20 mM Histidine, 270 mM Glycine; and 20 mM Histidine, 50 mM Glycine, and 3.8% Sorbitol.

The present invention has been detailed by direct description and by example. Equivalents and modifications of the present invention will be apparent to those skilled in the art, and are encompassed within the scope of the invention.

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Synthetic construct

<400> SEQUENCE: 1

tgactgtgaa cgttcgagat ga                                              22


<210> SEQ ID NO 2
<211> LENGTH: 22
<212> TYPE: DNA
<213> ORGANISM: Artificial Sequence
<220> FEATURE:
<223> OTHER INFORMATION: Synthetic construct

<400> SEQUENCE: 2

tgaccgtgaa cgttcgagat ga                                              22


<210> SEQ ID NO 3
<211> LENGTH: 23
<212> TYPE: DNA
<213> ORGANISM: Artificial Sequence
<220> FEATURE:
<223> OTHER INFORMATION: Synthetic construct

<400> SEQUENCE: 3

tcatctcgaa cgttccacag tca                                             23


<210> SEQ ID NO 4
<211> LENGTH: 22
<212> TYPE: DNA
<213> ORGANISM: Artificial Sequence
<220> FEATURE:
<223> OTHER INFORMATION: Synthetic construct

<400> SEQUENCE: 4

tgactgtgaa cgttccagat ga                                              22


<210> SEQ ID NO 5
<211> LENGTH: 26
<212> TYPE: DNA
<213> ORGANISM: Artificial Sequence
<220> FEATURE:
<223> OTHER INFORMATION: Synthetic construct

<400> SEQUENCE: 5

tccataacgt tcgcctaacg ttcgtc                                          26


<210> SEQ ID NO 6
<211> LENGTH: 22
```

-continued

```
<212> TYPE: DNA
<213> ORGANISM: Artificial Sequence
<220> FEATURE:
<223> OTHER INFORMATION: Synthetic construct
<221> NAME/KEY: misc_feature
<222> LOCATION: 11
<223> OTHER INFORMATION: n = 5-bromocytosine

<400> SEQUENCE: 6

tgactgtgaa ngttccagat ga                                              22


<210> SEQ ID NO 7
<211> LENGTH: 22
<212> TYPE: DNA
<213> ORGANISM: Artificial Sequence
<220> FEATURE:
<223> OTHER INFORMATION: Synthetic construct
<221> NAME/KEY: misc_feature
<222> LOCATION: 11
<223> OTHER INFORMATION: n = 5-bromocytosine

<400> SEQUENCE: 7

tgactgtgaa ngttcgagat ga                                              22


<210> SEQ ID NO 8
<211> LENGTH: 22
<212> TYPE: DNA
<213> ORGANISM: Artificial Sequence
<220> FEATURE:
<223> OTHER INFORMATION: Synthetic construct
<221> NAME/KEY: misc_feature
<222> LOCATION: 11, 15
<223> OTHER INFORMATION: n = 5-bromocytosine

<400> SEQUENCE: 8

tgactgtgaa ngttngagat ga                                              22
```

What is claimed as new and desired to be protected by Letters Patent of the United States is:

1. A composition comprising a structurally stable conjugate molecule, wherein the conjugate molecule comprises a conjugate partner and a polynucleotide comprising an immunostimulatory sequence (ISS), wherein the ISS comprises a 5'-CG-3' sequence, is greater than about 6 *bases or* base pairs in length, and is less than about 200 *bases or* base pairs in length, and wherein the composition further comprises a component capable of maintaining the pH of the composition in the range of about 6.0 to about 9.0, wherein the component is Histidine or Phosphate, and wherein the Phosphate, if present, is present in the composition at a concentration of between about 20 mM and about 50 mM.

2. The composition of claim 1 wherein the composition comprises more than about 70% of said conjugate molecule in non-aggregate form at a temperature of between about 2 degrees C. and about 8 degrees C. as measured by Right Angle Light Scatter (RALS).

3. The composition of claim 1 wherein the component capable of maintaining the pH is Histidine.

4. The composition of claim 3 wherein Histidine is present in the composition at a concentration of between about 1 mM and about 50 mM.

5. The composition of claim 4 wherein Histidine is present in the composition at a concentration of between about 5 mM and about 20 mM.

6. The composition of claim 1 wherein the component capable of maintaining the pH is Phosphate.

7. The composition of claim 1 wherein the pH of the composition is in the range of about 7.0 to about 8.0.

8. The composition of claim 1 wherein the pH of the composition is in the range of about 7.5 to about 8.0.

9. The composition of claim 1 wherein the ISS comprises the hexamer motif AACGTT.

10. The composition of claim 1 wherein the ISS comprises the motif

GACGCTCC;

GACGTCCC;

GACGTTCC;

GACGCCCC;

AGCGTTCC;

AGCGCTCC;

AGCGTCCC;

AGCGCCCC;

AACGTCCC;

AACGCCCC;

AACGTTCC;

AACGCTCC;

GGCGTTCC;

GGCGCTCC;

GGCGTCCC;

GGCGCCCC;

GACGCTCG;

GACGTCCG;

GACGCCCG;

GACGTTCG;

AGCGCTCG;

AGCGTTCG;

AGCGTCCG;

AGCGCCCG;

AACGTCCG;

AACGCCCG;

AACGTTCG;

AACGCTCG;

GGCGTTCG;

GGCGCTCG;

GGCGTCCG;

GGCGCCCG;

GACGCT;

GACGTC;

GACGTT;

GACGCC;

GACGCU;

GACGUC;

GACGUU;

GACGUT;

GACGTU;

AGCGTT;

AGCGCT;

AGCGTC;

AGCGCC;

AGCGUU;

AGCGCU;

AGCGUC;

AGCGUT;

AGCGTU;

AACGTC;

AACGCC;

AACGTT;

AACGCT;

AACGUC;

AACGUU;

AACGCU;

AACGUT;

AACGTU;

GGCGTT;

GGCGCT;

GGCGTC;

GGCGCC;

GGCGUU;

GGCGCU;

GGCGUC;

GGCGUT;

or

GGCGTU.

11. The composition of claim 1 wherein the ISS comprises the sequence

```
5'-TGACTGTGAACGTTCGAGATGA-3';          (SEQ ID NO: 1)
5'-TGACCGTGAACGTTCGAGATGA-3';          (SEQ ID NO: 2)
5'-TCATCTCGAACGTTCCACAGTCA-3';         (SEQ ID NO: 3)
5'-TGACTGTGAACGTTCCAGATGA-3';          (SEQ ID NO: 4)
5'-TCCATAACGTTCGCCTAACGTTCGTC-3';      (SEQ ID NO: 5)
5'-TGACTGTGAABGTTCCAGATGA-3';          (SEQ ID NO: 6)
5'-TGACTGTGAABGTTCGAGATGA-3';          (SEQ ID NO: 7)
or
5'-TGACTGTGAABGTTBGAGATGA-3',          (SEQ ID NO: 8)
```

where B is 5-bromocytosine.

12. The composition of claim 9 wherein the ISS comprises

5'-TGACTGTGAACGTTCGAGATGA-3'. (SEQ ID NO:1)

13. The composition of claim 1 wherein the conjugate partner is an antigen.

14. The composition of claim 13 wherein the antigen is an allergen.

15. The composition of claim [13] *14* wherein the allergen is selected from the group consisting of Crustacea allergens, insect allergens, mammalian allergens, mollusks allergens, plant allergens, and fungal allergens.

16. The composition of claim 15 wherein the allergen is the plant allergen Ragweed antigen Amb a 1.

17. The composition of claim 1 further comprising an amino acid selected from the group consisting of Histidine, Glycine, Isoleucine, Leucine, Proline and Alanine.

18. The composition of claim 17 wherein the amino acid is Glycine.

19. The composition of claim 18 wherein the Glycine is present in the composition at a concentration of between about 230 mM and about 285 mM.

20. The composition of claim 1 further comprising a carbohydrate selected from the group consisting of Lactose, Sucrose, Mannose, Maltose, Sorbitol, and Glucose.

21. The composition of claim 20 wherein the carbohydrate is Sucrose.

22. The composition of claim 21 wherein the Sucrose is present in the composition at a concentration of between about 1% and 10%.

23. The composition of claim 20 wherein the carbohydrate is Sorbitol.

24. The composition of claim 23 wherein the Sorbitol is present in the composition at a concentration of between about 3% and about 5%.

25. A composition comprising a conjugate molecule, wherein the conjugate molecule comprises a conjugate partner and a polynucleotide comprising an immunostimulatory sequence (ISS), wherein the ISS comprises a 5'-CG-3' sequence, is greater than about 6 *bases or* base pairs in length, and is less than about 200 *bases or* base pairs in length, and wherein the composition further comprises Histidine at a concentration in the range of about 1 mM to about 50 mM; and Glycine at a concentration in the range of about 50 mM to about 300 mM, wherein said composition has a pH in the range of about 6.0 to about 9.0.

26. The composition of claim 25 further comprising Sorbitol in the range of about 1 to 10%.

27. The composition of claim 25 further comprising Sucrose at a concentration of about 200 mM to about 250 mM.

28. The composition of claim 25 wherein said composition has a pH in the range of about 7.0 to about 8.0.

29. The composition of claim 28 comprising 5 mM Histidine and 285 mM Glycine.

30. The composition of claim 28 comprising 20 mM Histidine and 270 mM Glycine.

31. The composition of claim 28 comprising 20 mM Histidine, 50 mM Glycine, and 3.8% Sorbitol.

32. The composition of claim 28 comprising 20 mM Histidine, 50 mM Glycine, and 210 mM Sucrose.

33. The composition of claim 25 wherein the conjugate partner is an allergen.

34. The composition of claim 33 wherein the allergen is a plant allergen.

35. The composition of claim 34 wherein the plant allergen is Ragweed antigen Amb a1.

36. A lyophilized composition produced by lyophilizing the composition of claim 20 under suitable conditions.

37. A lyophilized composition comprising the composition of claim 26 or 27.

*38. The composition of claim 1 or claim 25, wherein the polynucleotide is single-stranded DNA.*

* * * * *